United States Patent
Kia et al.

(10) Patent No.: US 12,089,835 B2
(45) Date of Patent: Sep. 17, 2024

(54) DEVICE AND SYSTEM FOR HERNIA REPAIR

(71) Applicants: Atropos Limited, Bray (IE); Michael Amirfarzad Kia, Grand Blanc, MI (US)

(72) Inventors: Michael Amirfarzad Kia, Grand Blanc, MI (US); Frank Bonadio, Bray (IE); Lucy Dolores Halpin, Rathfarnham (IE); Shane Joseph Macnally, Delgany (IE); Ronan Bernard Mcmanus, Bray (IE); Stephen Williams, Blackrock (IE)

(73) Assignee: Atropos Limited, Bray (IE)

( * ) Notice: Subject to any disclaimer, the term of this patent is extended or adjusted under 35 U.S.C. 154(b) by 633 days.

(21) Appl. No.: 17/260,696

(22) PCT Filed: Jul. 12, 2019

(86) PCT No.: PCT/EP2019/068801
§ 371 (c)(1),
(2) Date: Jan. 15, 2021

(87) PCT Pub. No.: WO2020/016125
PCT Pub. Date: Jan. 23, 2020

(65) Prior Publication Data
US 2021/0298743 A1    Sep. 30, 2021

Related U.S. Application Data

(60) Provisional application No. 62/853,375, filed on May 28, 2019, provisional application No. 62/699,937, filed on Jul. 18, 2018.

(51) Int. Cl.
*A61B 17/04*    (2006.01)
*A61B 17/06*    (2006.01)
(Continued)

(52) U.S. Cl.
CPC .... *A61B 17/0482* (2013.01); *A61B 17/06128* (2013.01); *A61B 17/06166* (2013.01);
(Continued)

(58) Field of Classification Search
CPC .......... A61B 17/0482; A61B 17/06128; A61B 17/06166; A61B 17/062;
(Continued)

(56) References Cited

U.S. PATENT DOCUMENTS 5,439,469 A * 8/1995 Heaven .............. A61B 17/0469
  223/102
10,939,909 B2 * 3/2021 Zeiner .............. A61B 17/06114
(Continued)

FOREIGN PATENT DOCUMENTS

WO    WO 2014/040369 A1    3/2014
WO       2020/016125 A1    1/2020

OTHER PUBLICATIONS

Written Opinion issued on Nov. 16, 2021 in International Patent Application No. PCT/US2020/034655 (12 pages, in English).

*Primary Examiner* — Phong Son H Dang
(74) *Attorney, Agent, or Firm* — Bookoff McAndrews, PLLC

(57) ABSTRACT

A suture device comprises a needle (5) which is movable between a retracted configuration and an extended configuration and a drive for rotating the needle between the retracted and extended configurations. The drive comprises an axle (18) which is rotated by a rack (12) and pinion (10) system.

13 Claims, 68 Drawing Sheets

(51) Int. Cl.
*A61B 17/062* (2006.01)
*A61B 17/00* (2006.01)

(52) U.S. Cl.
CPC .. *A61B 17/062* (2013.01); *A61B 2017/00398* (2013.01); *A61B 2017/00526* (2013.01); *A61B 2017/0608* (2013.01); *A61B 2017/0619* (2013.01)

(58) Field of Classification Search
CPC A61B 2017/00398; A61B 2017/00526; A61B 2017/0619
See application file for complete search history.

(56) References Cited

U.S. PATENT DOCUMENTS

| | | |
|---|---|---|
| 2002/0116011 A1 | 8/2002 | Sheung et al. |
| 2003/0208100 A1 | 6/2003 | Gil |
| 2004/0236374 A1* | 11/2004 | Bonutti ............ A61B 17/0487 606/232 |
| 2006/0069396 A1* | 3/2006 | Meade ............... A61B 17/0482 606/144 |
| 2009/0182353 A1* | 7/2009 | Snell ....................... H05B 3/06 606/139 |
| 2011/0015654 A1 | 1/2011 | Yang-Hwei et al. |
| 2013/0158568 A1 | 6/2013 | Kia et al. |
| 2016/0242763 A1* | 8/2016 | Kia .................... A61B 17/0469 |
| 2019/0298331 A1* | 10/2019 | Bonutti ............ A61B 17/0487 |

* cited by examiner

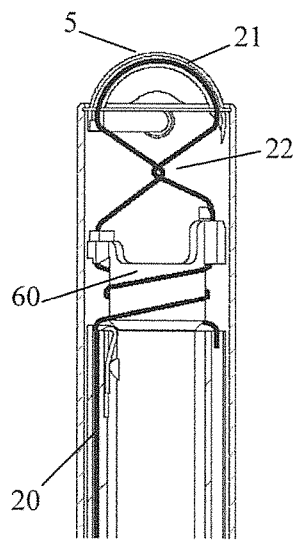 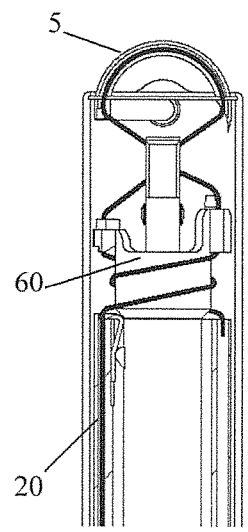 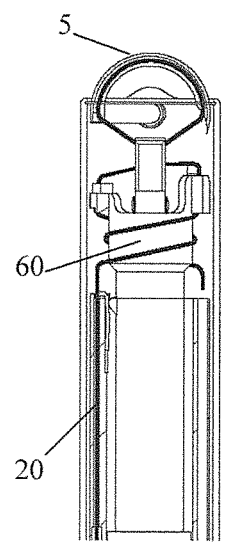 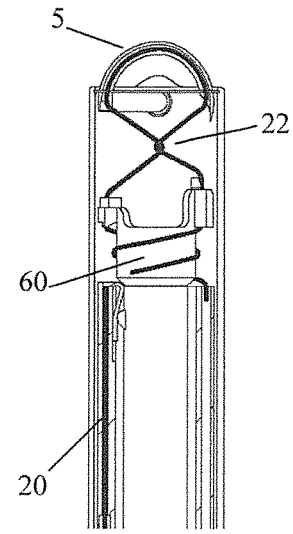
Fig. 5i     Fig. 5j     Fig. 5k     Fig. 5l
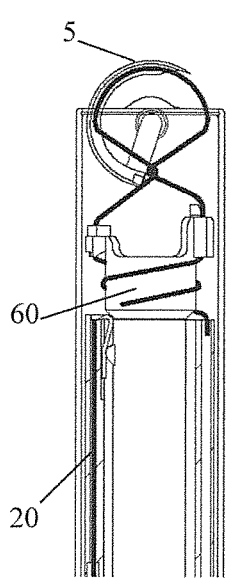 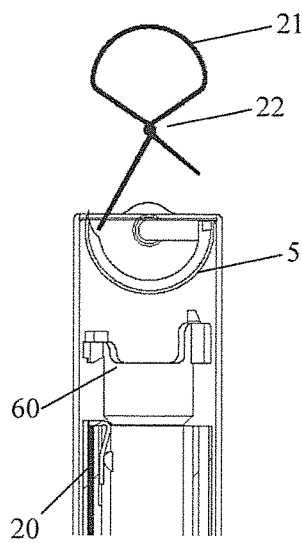 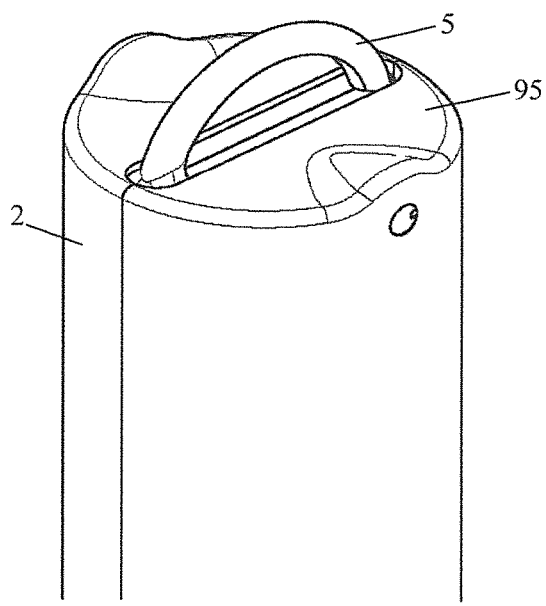
Fig. 5m     Fig. 5n     Fig. 6a

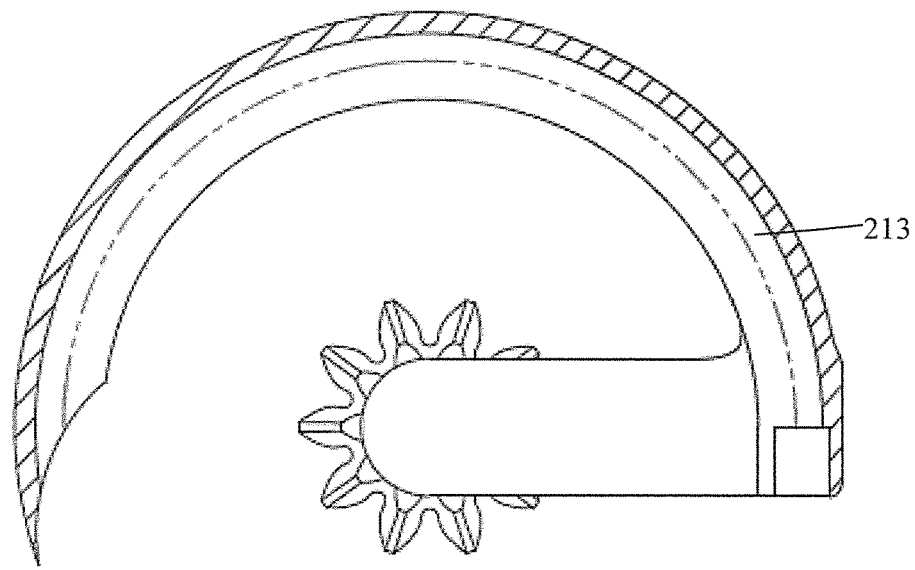
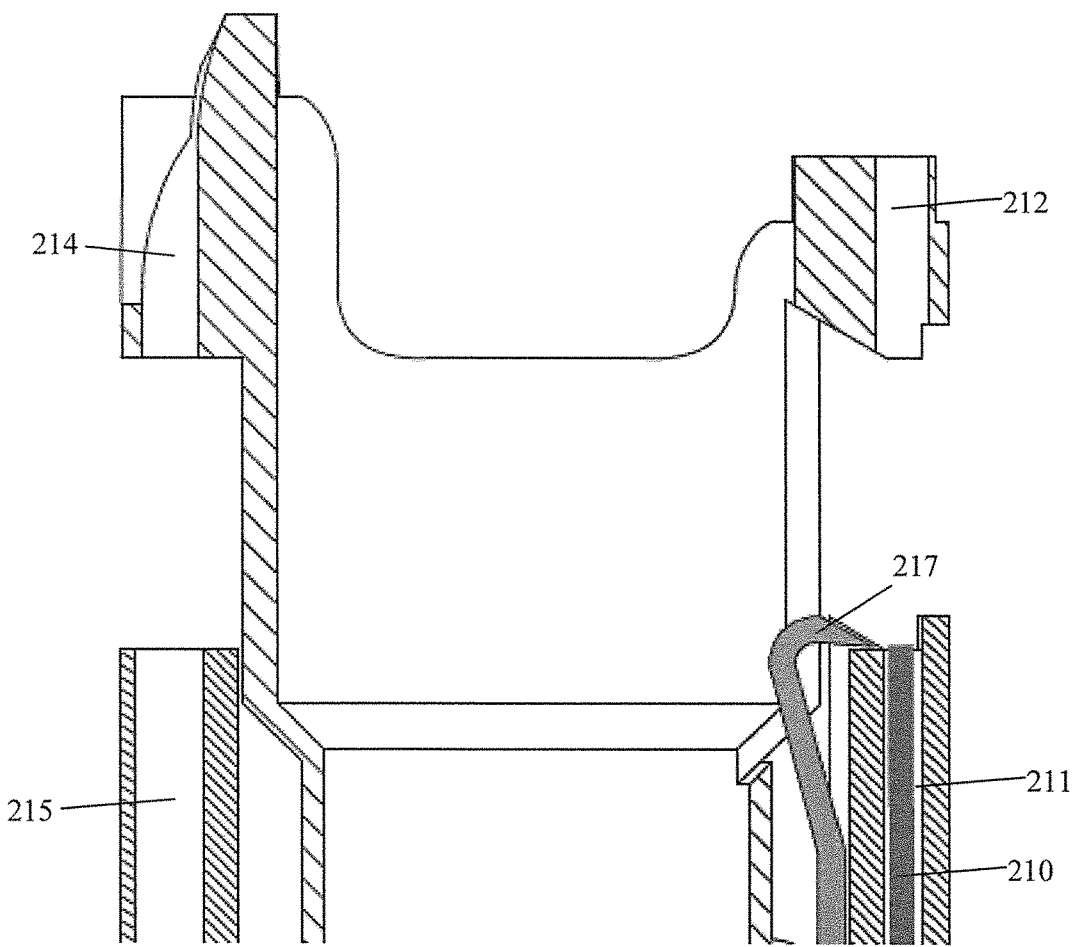
Fig. 30

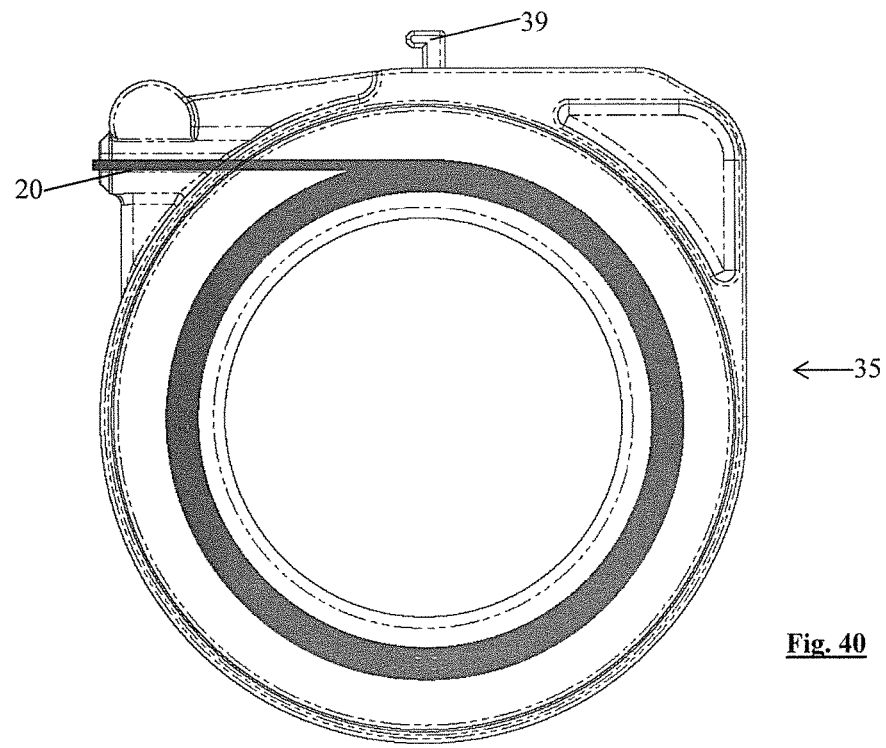
Fig. 40
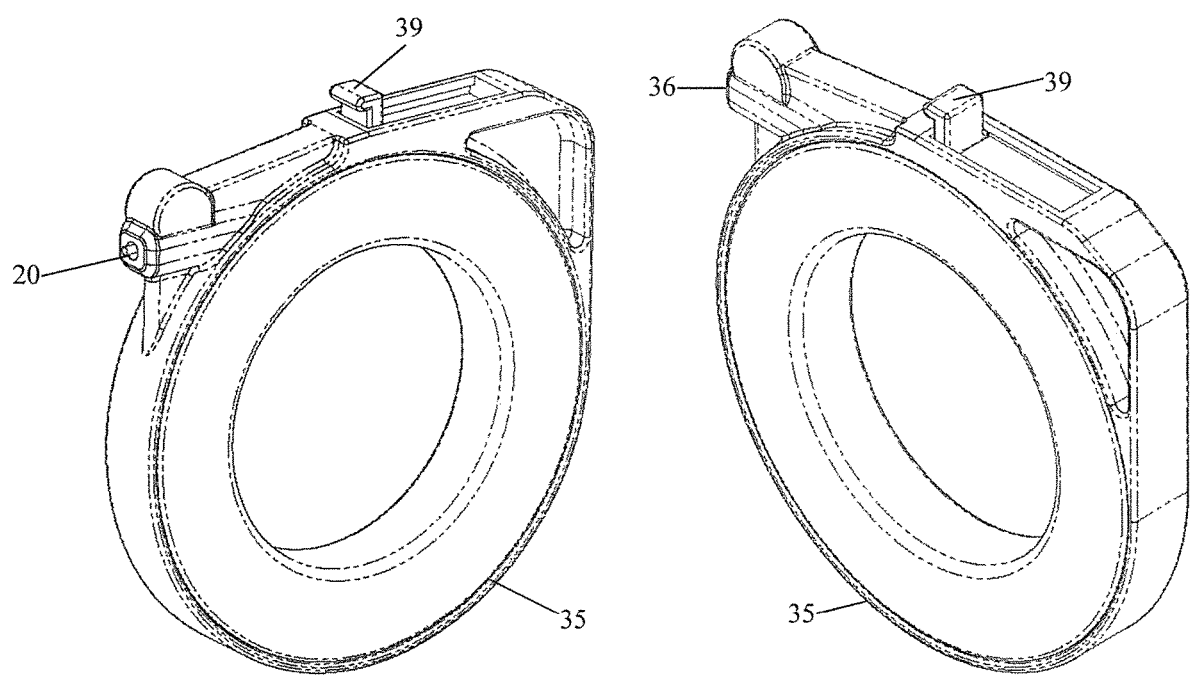
Fig. 41
Fig. 42

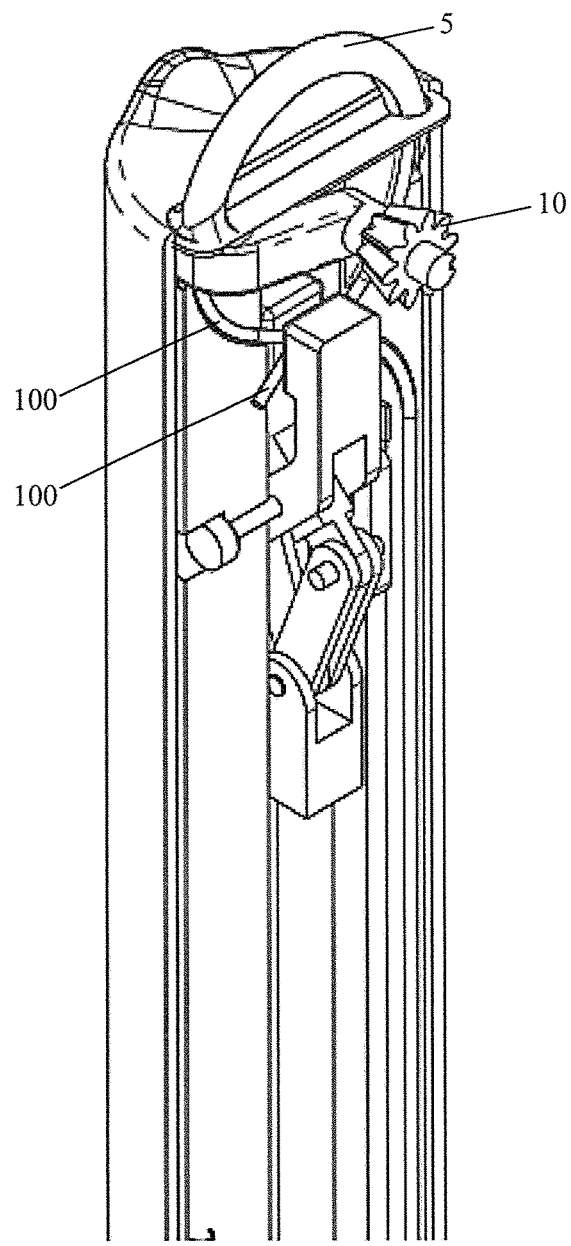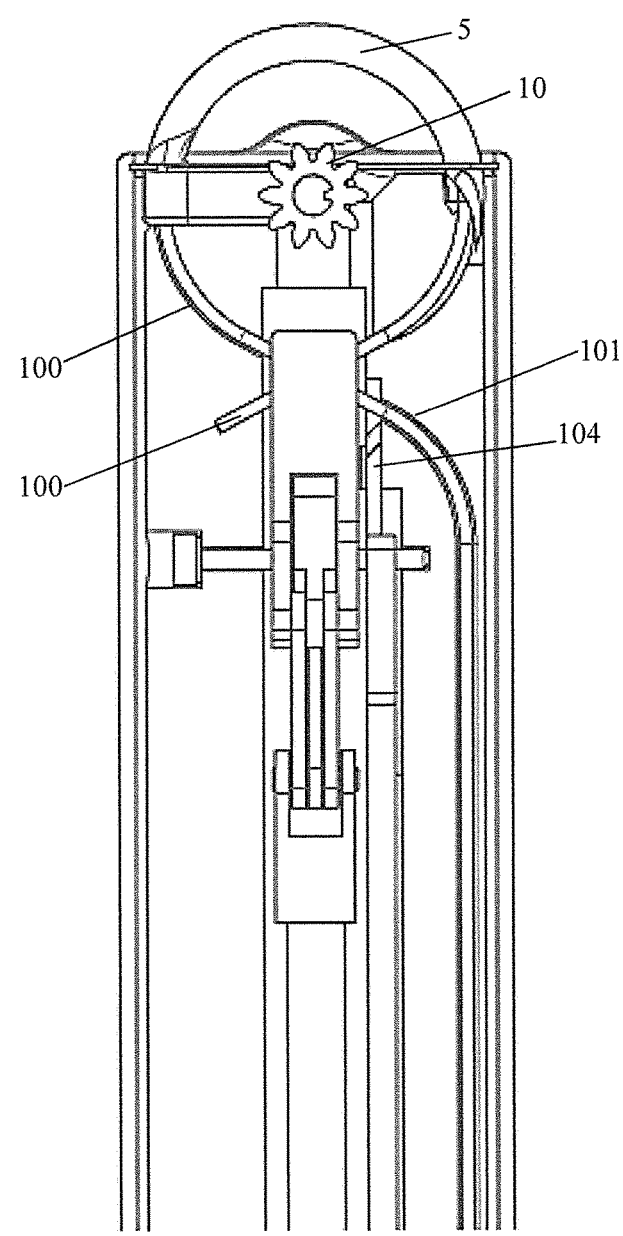
Fig. 57                     Fig. 58

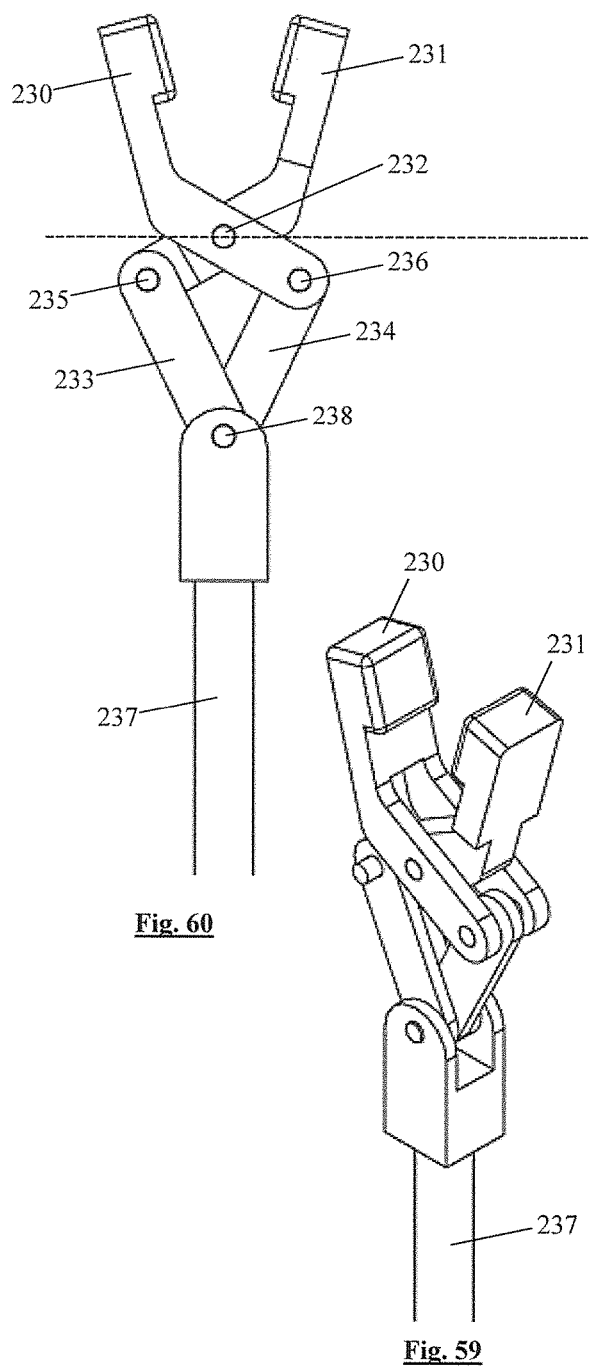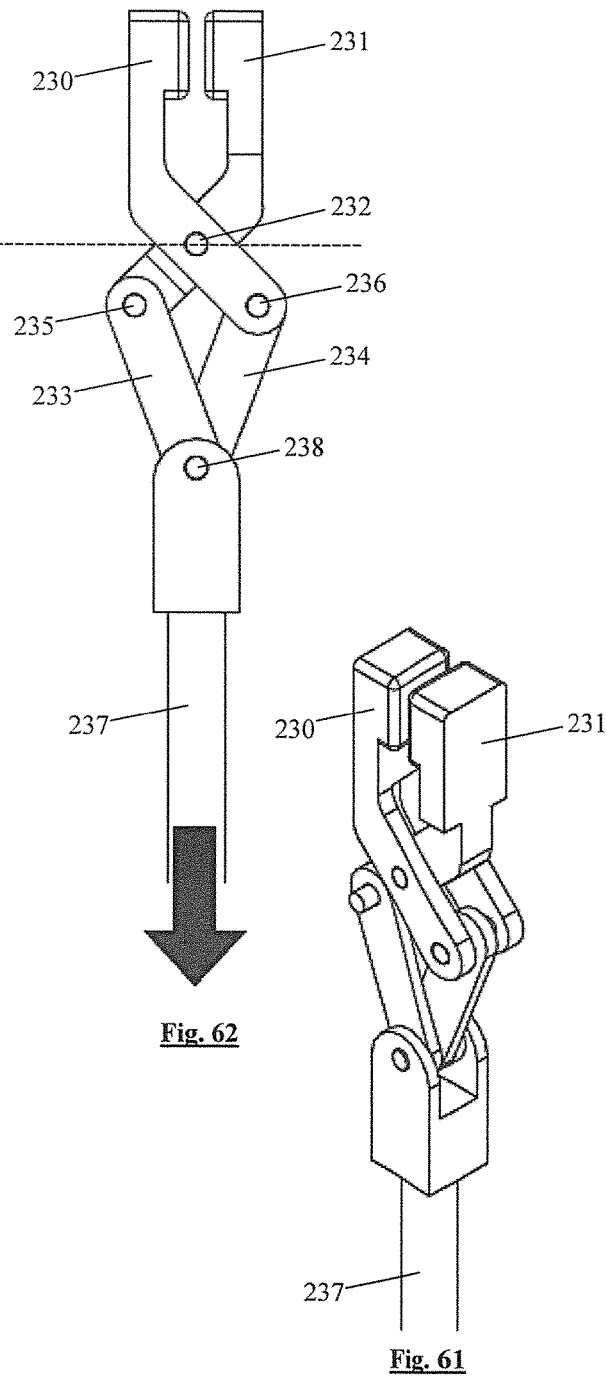
Fig. 60
Fig. 59
Fig. 62
Fig. 61

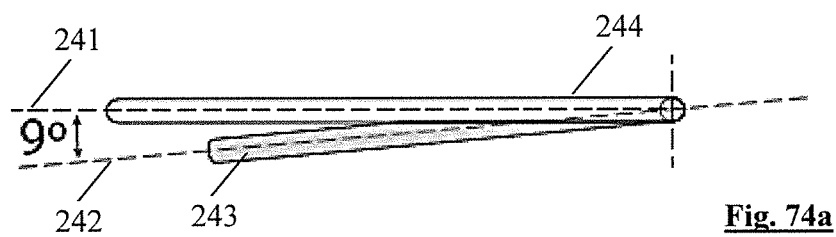
Fig. 74a
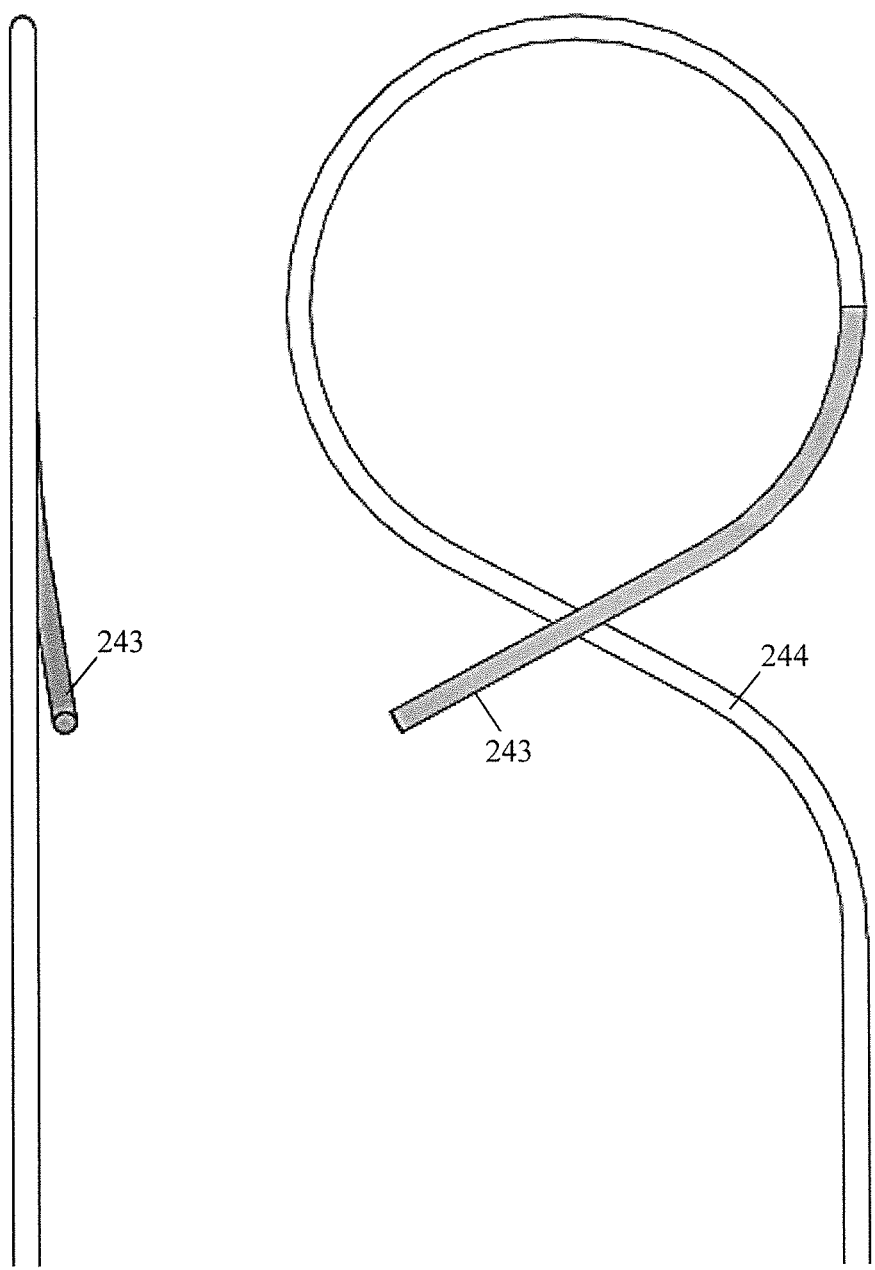
Fig. 74b
Fig. 74c

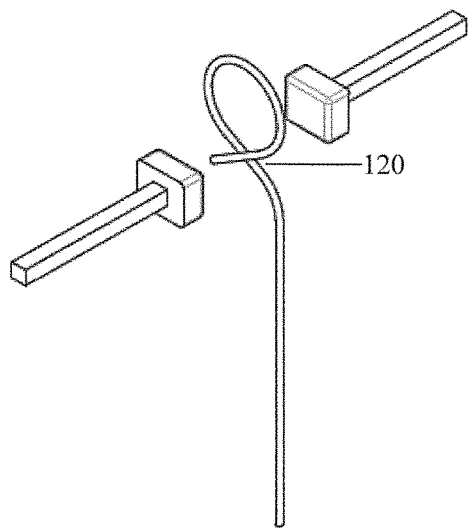
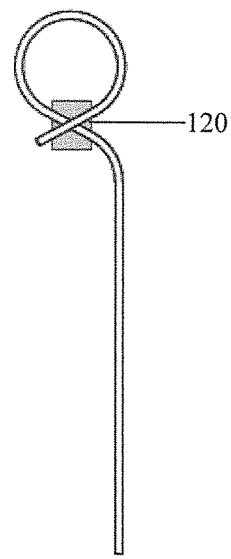
Fig. 77  Fig. 78
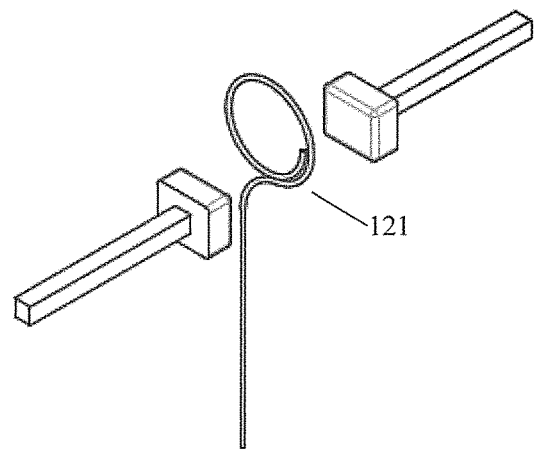
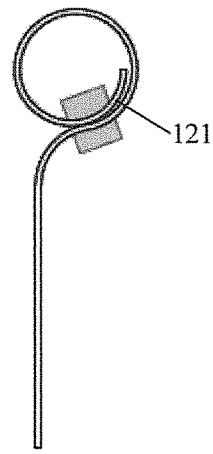
Fig. 79  Fig. 80

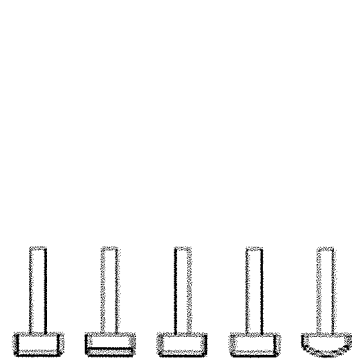
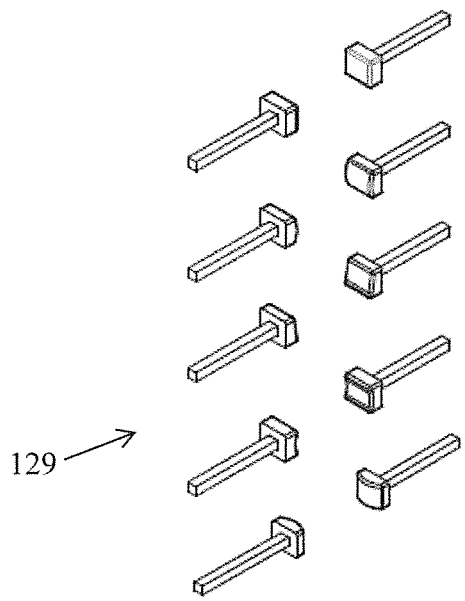
←—129
129—→
Fig. 86
Fig. 87
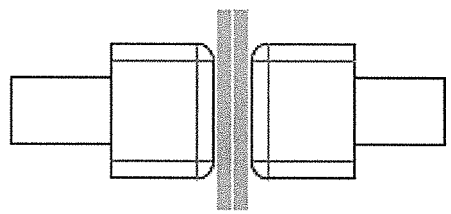
Fig. 88
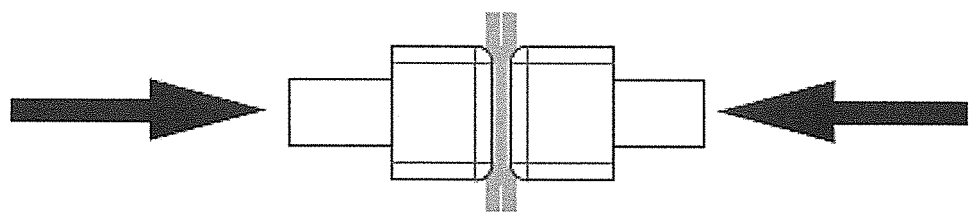
Fig. 89

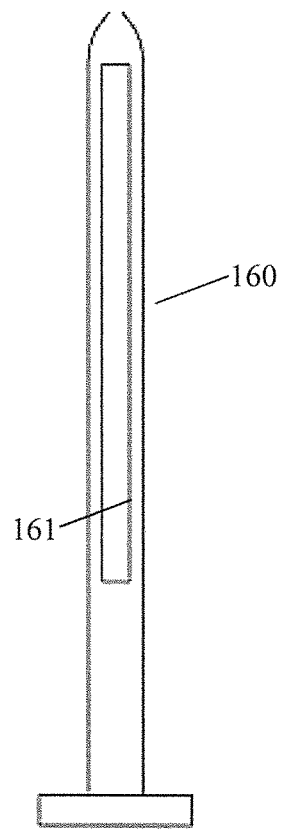
Fig. 119
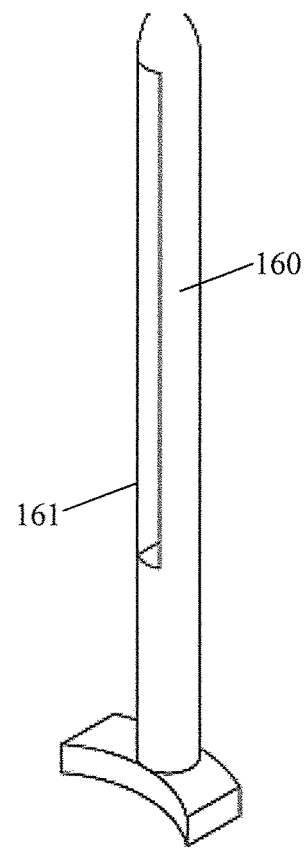
Fig. 120
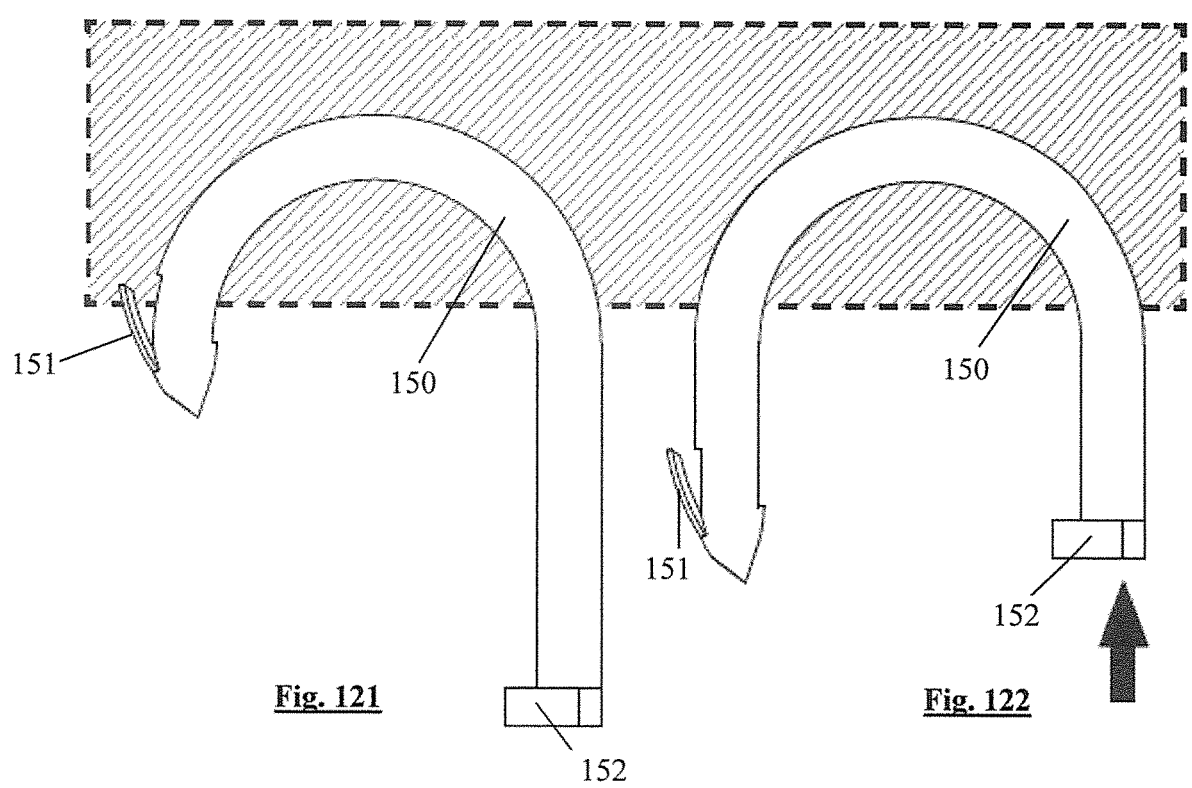
Fig. 121
Fig. 122

DEVICE AND SYSTEM FOR HERNIA REPAIR

CROSS-REFERENCE TO RELATED APPLICATION(S)

This application is the U.S. national phase entry under 35 U.S.C. § 371 of International Application No. PCT/EP2019/068801, filed on Jul. 12, 2019, which claims priority to U.S. Provisional Application No. 62/699,937, filed Jul. 18, 2018, and U.S. Provisional Application No. 62/853,375, filed May 28, 2019, the contents of each of which is incorporated herein in its entirety.

The invention relates to a device and a system for hernia repair.

INTRODUCTION

A hernia is a development of a gap in the connective tissue of the abdominal wall. One type of hernia is a ventral hernia that can form in the linea alba region of the body. In such hernias often a weakness develops in the abdominal wall that contains the intestine. Part of the intestine pushes into the weakened area and can become restricted leading to digestive complications and pain.

To repair such hernias usually a mesh is used to bridge the weakened area in the abdominal wall. Such ventrical hernia repair procedures can be carried out either using open surgery or closed laparoscopic surgery.

In open surgery procedures an open incision is made and a synthetic or biological mesh is used to bridge the gap. The mesh is secured in position using standard suturing techniques. Generally in such open surgical procedures the mesh is sewn with sutures which are not biologically absorbable.

In conventional laparoscopic hernia repair procedures a mesh is secured in position using tacks which are delivered laparoscopically and/or transfascial sutures are used which are delivered transabdominally. Such transabdominal suturing techniques are however time consuming and can be technically challenging. The sutures and the associated tacks can cause significant patient discomfort and pain. The rate of subsequent infection after laparoscopic hernia repair is substantially less than in open surgery. The recovery time is also much faster than for open surgery hernia repair.

US2013/0158568A describes a suture device comprising a hollow shaft, a pair of jaws at one end of the hollow shaft, a locking device, a cutting device and a heating device.

WO2015/050999A describes a suture device comprising a shaft and a rotatable needle which creates a curved pathway for delivery of a suture. The device also comprises a rotatable twisting element and a heating element to heat meld the twist formed in the surface.

An object of the invention is to provide devices and systems for improved laparoscopic hernia repair.

STATEMENTS OF INVENTION

According to the invention there is provided a suture or tack device comprising a needle which is movable between a retracted configuration and an extended configuration and a drive for rotating the needle between the retracted and extended configuration.

In one case the needle comprises a driven element which is rotated by the drive.

The driven element may comprise an axle and a wheel for turning the axle. In one case the driven element comprises a gear wheel. The gear wheel may be integral with the needle. The needle and the gear wheel may be monolithic.

In one case the needle and the gear wheel are formed by 3D printing. The needle and the gear wheel may be of metal such as titanium or steel such as stainless steel.

In one case the driver comprises a rotatable shaft and a shaft gear which is adapted to engage with the needle gear wheel. The shaft gear may comprise a sector gear and the needle gear wheel comprises a bevelled gear which is engaged by the sector gear.

The suture device in some cases comprises a motor for driving the shaft in one direction, for moving the needle between the retracted configuration and the extended configuration, and a second direction opposite to the first direction for moving the needle between the extended and retracted configurations. Rotation of the shaft through an angle of from 30° to 180°, typically 30° to 90° (such as 60°) may be adapted to rotate the needle through 180°.

The suture device may comprise a motor for rotating the shaft.

In one case the suture device further comprises a twisting component for twisting a suture to form a loop. The twisting component may be adapted to twist the suture between 180° and 540°.

The twisting component in some cases is movable from a retracted configuration to an extended configuration, the extended configuration providing a pathway for delivery of a suture to the needle.

The suture device may further comprise a fusing component for fusing the looped suture.

The fusing component may comprise a clamp. Alternatively or additionally, the fusing component comprises a heater.

In one case, the fusing component comprises heated plates which are clamped around portion of the looped suture to fuse the suture into the loop.

The suture device may comprise a housing for the needle in the retracted configuration. The housing may have a distal end through which the needle extends in the extended configuration and the device comprises a sealing flap at the distal end which is adapted to facilitate passage of the needle and to substantially prevent ingress of material into the housing.

In some cases the suture device further comprises a cutting component for cutting the suture after a suture loop is formed.

In one case the suture device comprises a receiver for a replaceable suture cartridge.

The device may comprise an activator for activating the device on insertion of a cartridge. The activator may be a mechanical activator and/or an electronic activator.

In one case the activator comprises a reader, such as a RFID reader, for reading a tag such as an RFID tag on the cartridge. The device may comprise a control system for controlling the operation of the device dependent on suture parameters, for example, as read from the RFID tag.

The cartridge may comprise a housing for a length of suture, the housing having an outlet through which the suture is led.

There may be a suture advancer for advancing the suture through the suture outlet. The suture advancer may comprise an advancing element and a trigger for activating the advancing element.

The invention also provides a suture cartridge which is adapted for mounting to a suture device.

The suture cartridge may comprise a housing for a length of suture, the housing having an outlet through which the suture is led.

The suture cartridge may further comprise a suture advancer for advancing the suture through the suture outlet. The suture advancer in some cases comprise an advancing element and a trigger for activating the advancing element.

The invention further provides a system comprising a suture device of the invention and a cartridge of the invention. The cartridge may comprise a suture advancer and the suture device comprises an activator for activating the suture advancer when the cartridge is mounted to the suture device.

Also described is a suture device comprising a shaft, a needle at the distal end of the shaft to create a curved pathway for delivery of a suture through portion of an internal body wall and a closure device for closing the suture to form a loop.

In one case the needle is movable from a retracted configuration at least partially within the shaft to an extended configuration for passing through portion of an internal body wall. In one case the needle is rotatably movable between the retracted and the extended configuration. In one case the needle has a distal tip which projects from the distal end of the shaft. The device may comprise a retractable shroud for the projecting distal tip of the needle. In one case the needle is of arcuate shape. In one case the needle comprises an open suture-receiving channel. The suture-receiving channel may be of generally U-shaped in transverse cross section.

In one case the device comprises a proximal handle for controlling movement of the needle. There may be operating elements extending between the proximal handle and the needle. The suture device may comprise a rotary device for twisting the suture to form a loop. The suture device may comprise a heating device for fusing the suture. The suture device may comprise a cutting device for cutting the suture.

In one case the device comprises a suture feed channel for delivering a suture to the needle. The device may also comprise a suture return channel for receiving a suture delivered through the needle.

In one case the suture device comprises a rotary device for twisting the suture to form a loop, the twisting device having a suture receiving hole and a suture return hole, the rotary device being rotatable from a receiving configuration in which the suture receiving hole and the suture return hole are in alignment with the suture feed channel and the suture return channel respectively to a twisted configuration in which the suture receiving hole and the suture return hole are in alignment with the suture return channel and the suture feed channel respectively. In one case the suture return channel has an opening at the distal end which is larger than an opening at the distal end of the suture feed channel.

In one case the suture device further comprises a fusing element for fusing a twist in a suture. The device may also comprise a suture cutting element for cutting the twisted suture. The fusing element may be movable from a retracted to an advanced configuration. In one case the cutting element is activated on movement of the fusing element from the retracted to the advanced configuration.

In one case the needle is mounted to an arm which is rotatably mounted to the shaft. The device may comprise an operating system for the needle arm. The operation system comprises operating elements extending from the needle arm to the proximal end of the shaft. The device may comprise a proximal handle for controlling the movement of the needle from the proximal end of the shaft.

In one case the suture device comprises a retainer or bridge for stabilising the suture during cutting and/or fusing.

In some cases at least a portion of the shaft is adjustable. For example, at least a portion of the shaft may be flexible and/or malleable. In one case at least a portion of the shaft is rotatable. In one embodiment the shaft comprises at least one bend.

In the invention an automated suturing mechanism involves passing a suture through a hollow curved needle to secure a mesh to the abdominal wall. The suture will be welded/fused to form a bond, for example, using a grooved heating element.

In one case the device will contain a rotational heating shaft that will be used to create an overlap of suture. The rotational heating element will function to capture the two strands of the suture and create an overlap to allow for suture welding. The rotational element may have wing(s) that can capture the suture strands within the shaft of the device. The wing may be offset from a center channel of the heating element.

In one case the heating element may press the suture against the mesh to serve as an endplate for welding the mesh.

In one case the device will have an outer shaft and inner shaft that will be able to move independently. The inner shaft may contain the suture strands within closed or partially open channels. Movement of the inner shaft may be used to expose the suture for the rotational element. In one case the inner shaft may rotate to create a crossing of the suture strands. In another case the inner shaft may move to a position to carry the distal ends of the suture loop to a point perpendicular to the heating element to allow for suture welding. In another case the retraction of the inner shaft may be used to facilitate locking of the distal tail of the suture.

In one case the end effector on the outer or inner shaft will have bridges to limit collapse of the suture loop. This will ensure that every loop is of the same diameter independent of the material within the loop. In one case the bridges will cause predictable alignment of the suture strands in front of the heating element (for example, perpendicularly). In another case the bridge on the end effector will limit the tension on the tissue caught in the suture loop. In another case the suture used in the device may comprise three layers of progressively increasing melting temperature from the outside to the inside.

In one case the mesh that may be used with the device of the invention will have precut perforations in the edges to allow for penetrance of the needle. These precut perforations will be marked for identification. The perforations may be linear, circular, or other shape and may be located at variable distances to allow for proper function for fixation.

A hernia repair mesh may have a plurality of holes provided therein to receive a suture. In one case the suture receiving holes are provided around at least a portion of the periphery of the mesh.

A hernia repair mesh may have a main mesh body and a peripheral portion surrounding the main mesh body, the peripheral portion being adapted for reception of sutures. In one case the peripheral portion is softer with respect to the main mesh body. Alternatively or additionally the peripheral portion is of reduced thickness with respect to the main mesh body. In one case the hernia repair mesh comprises a plurality of holes to receive individual sutures.

In another aspect the invention provides a hernia repair system and a mesh as described.

In yet another aspect of the invention provides a method for repairing a hernia comprising the steps of:— providing a suture device as defined;
providing a mesh;
laparoscopically delivering the mesh to the site of the hernia;
delivering the suture device to the site of the hernia; and
laparoscopically suturing the mesh to an internal body wall at the site of the hernia.

In one case the step of suturing the mesh comprises suturing a plurality of individual sutures to an internal body wall at the site of the hernia.

In one case the suture comprises a closed loop which extends through the mesh, into the body wall and out of the body wall. In one case the loop is adapted to facilitate movement of the mesh relative to the body wall.

The invention also provides a tack which is adapted for loosely engaging with a mesh or the like. The tack may comprise a live hinge barb adjacent the distal tip of the tack to enhance fixation. There may be a flange at the proximal end. The tack may be bent into a curved shape by a tack insertion device.

BRIEF DESCRIPTION OF THE DRAWINGS

The invention will be more clearly understood from the following description thereof, given by way of example only, in which:

FIGS. 6a to 6l illustrate details and operation of a distal end of the suture device;

FIGS. 30 to 35 are cross sectional views illustrating a sequence of operation of the suture device;

FIGS. 40 to 44 are views of a suture cartridge according to the invention;

FIGS. 50 to 58 are a series of images of another suture device of the invention in various configurations of use;

FIGS. 59 to 61 are views of a clamping system of the suture device, in use;

FIGS. 62 to 72 are a series of images of the suture device of FIGS. 58 to 61 in further configurations;

FIGS. 73 and 74a to 74c illustrate the overlapping of a suture in operation of the suture device;

FIGS. 77 to 85 illustrate various suture bonding configurations;

FIGS. 86 and 87 are images of various heating plates used for suture bonding;

FIGS. 88 to 97 illustrate various heating plates, in use;

FIGS. 119 and 120 are illustrations of a blank used to form a tack;

FIGS. 121 and 122 illustrate shaping of the tack;

DETAILED DESCRIPTION

Figure 1:
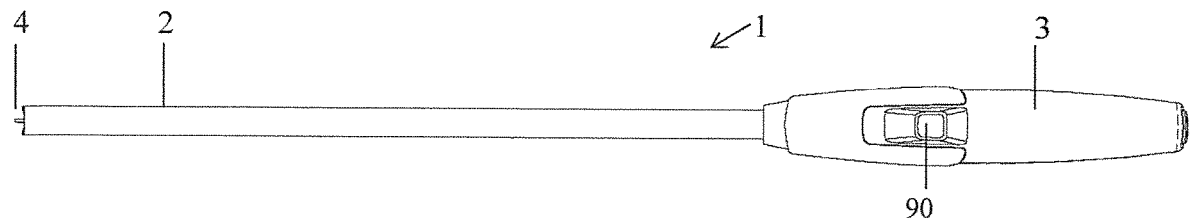
FIGS. 1 and 2 are views of a suture device according to the invention.
Figure 2:
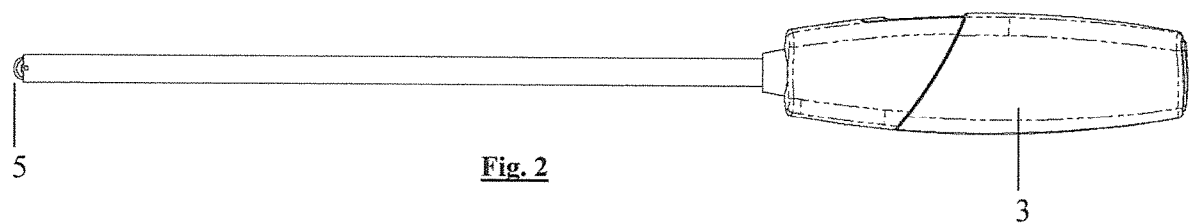
Figure 3:
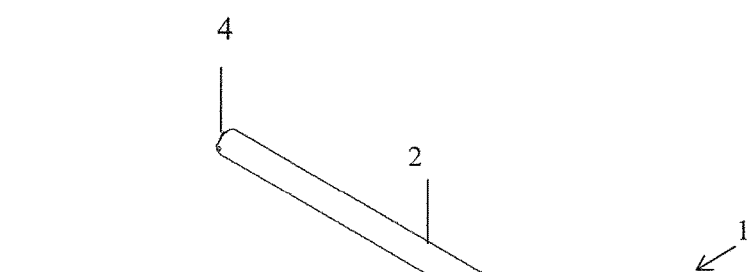
FIGS. 3 and 4 are views of a suture device with a replaceable suture cartridge.
Figure 4:
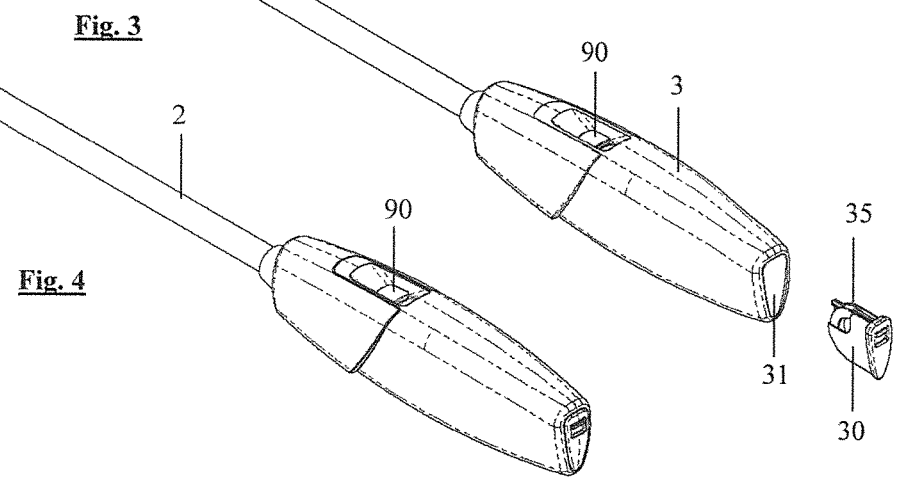

U.S. patent application Ser. No. 13/714,540 (published as US2013/0158568A) describes an automated suture device. U.S. patent application Ser. No. 15/026,028 (published as US2016/0242763A) describes a suture device. The entire disclosure of these applications is incorporated herein by reference.

Referring to the drawings and initially to FIGS. 1 to 49 there is illustrated a suture device 1 comprising a housing or a shaft 2 and a handle 3. A curved needle 5 is movable between a retracted configuration at a distal end 4 of the housing 2, to an extended configuration in which the needle 5 extends from the distal end of the housing 2.

The needle comprises a driven element which in this case is a gear wheel such as a bevelled gear wheel 10 which is rotated by a drive. The drive in this case comprises a shaft 11 within the housing 2. The shaft 11 has a shaft gear, such as a sector gear 12, at the distal end which engages with the bevelled gear wheel 10 of the needle. The shaft 11 is rotated by a motor which drives the shaft to move the sector gear 12 and hence the needle 5. The shaft 11 is driven in one direction to move the needle from the retracted to the extended configuration and is driven in an opposite direction to move the needle from the extended to the retracted configuration.

The needle includes an axle 18. The needle part, the axle 18 and the gear wheel 10 may be a single 3D printed part which is cost effective and provides a high level of accuracy which is important in efficient and effective movement of the needle.

A length of suture 20 is delivered through the needle 5, twisted to form a loop 21 and an overlap region 22 of the suture is fused.

The suture may be of a non-bioabsorbable material such as propylene. One such suture is available from Ethicon under the name PROLENE®.

Depending on the application requirements, the suture may also be of a suitable bioabsorbable material such as a polydioxanone. One such suture is PDS II (polydioxanone) suture available from Ethicon.

In the invention, the suture may be provided in a pre-loaded cartridge 35 which is removably and replaceably mounted to the handle 3 of the suture device. For example, the suture cartridge 35 may be loaded into a drawer 30 which is mounted to the handle 3. The cartridge 35 comprises a housing having an outlet 36 through which the suture 20 is led. The cartridge may comprise a suture advancer for advancing the suture 21 through the suture outlet 36. The suture advancer may comprise an advancing element such as a wheel 37 on a wire 38 and a trigger 39 for activating the advancing element 37. The suture device may comprise an activator for activating the trigger 39 when the cartridge 35 is mounted to the suture device.

The length 20 of suture may be advanced through the device using a wheel 40 which may be coated with or comprise a suitable flexible material such as rubber which engages the suture 20 and drives it forwardly.

In one case, the suture 21 is advanced through the needle 5 and is then twisted by a twisting component 60 to form a loop 21. The overlapped region 22 of the suture is then fused using a fusing component 70. When fused, the suture may be cut by a cutting component 80.

The twisting component 60 is movable from a retracted inactivated configuration in which the twisting component 60 is engaged with the suture and twisted to form the suture loop 21 with overlap 22.

The fusing component 70 in this case comprises clamping plates 71, 72 which are movable from a release configuration to receive the suture overlap region, to an engaged configuration in which the overlap region of the suture is clamped and heated.

FIGS. 1 to 4 illustrate a suture device 1 for fixing a mesh in place. The device may be sized for use in laparoscopic procedures and may consist of a 360 mm long shaft with a 13.8 mm diameter. Typically the shaft diameter is in the range 8 to 15 mm, typically 10 to 15 mm, preferably 12 mm or less. The outer housing shaft 2 may be of metal to provide strength. The handle 3 may house all the necessary motors and batteries. In this case, the device is operated by a single button 90 and has a suture drawer 30 that opens to facilitate insertion of a removable and replaceable suture cartridge 35.

The use of a separate suture cartridge allows the suture to be stored outside of the device and its packaging. This is particularly advantageous as sutures (especially bioabsorbable sutures) have a shorter shelf life than the shelf life of the suture applicator device.

The cartridge system also facilitates use of a range of sutures having different properties with the device—for example absorbable/non-absorbable sutures and/or sutures with differing dimensions. There may be a system to adjust the operation of the device to align with the suture in the cartridge loaded into the device. The activator system may be automatically operated before or on insertion of the suture cartridge. For example, the suture cartridge may have an electronic tag (such as an RFID tag) and the device may have a tag reader. The operation of the device may thereby be automatically set dependent on the suture loaded into the device. For example the device heating temperature or heating time may be altered to suit a particular suture. Alternatively, the re-set may be triggered mechanically, for example, by activation of a switch on insertion of the cartridge.

Figure 5A:
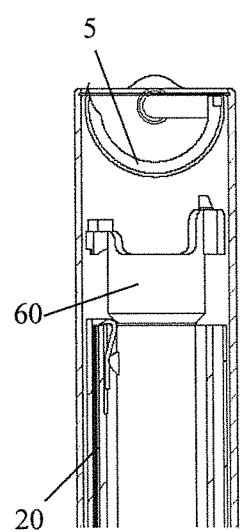
FIGS. 5a to 5n illustrate various steps in use of the suture device.
Figure 5B:
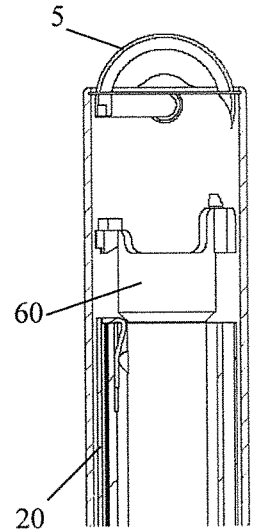
Figure 5C:
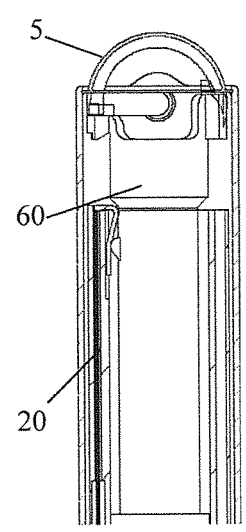
Figure 5D:
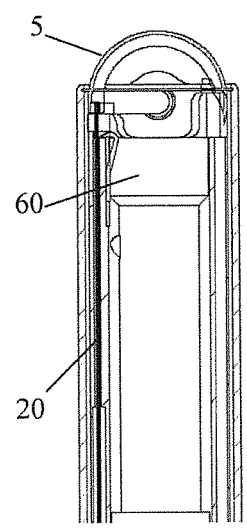
Figure 5E:
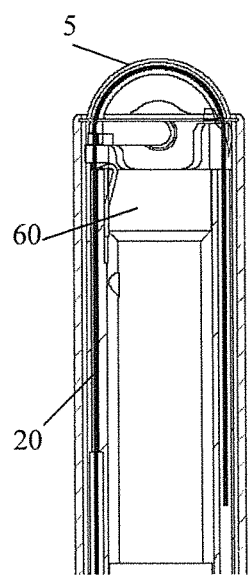
Figure 5F:
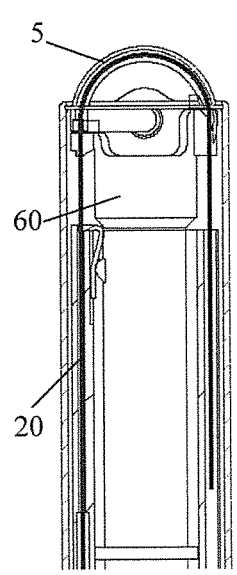
Figure 5G:
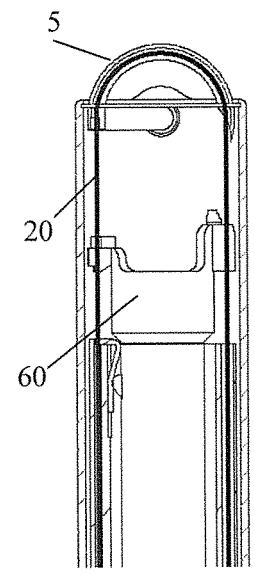
Figure 5H:
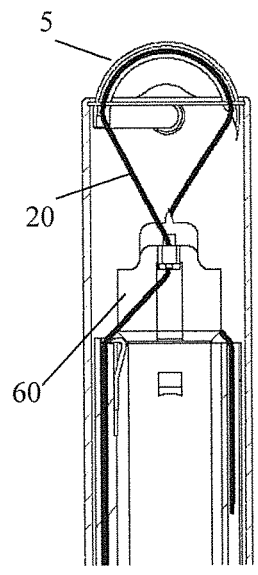

FIGS. 5a to 5n illustrate various steps in the use of the device. FIG. 5a shows the needle 5 in a retracted configuration. FIG. 5b shows the needle 5 rotated into the extended configuration. FIG. 5c shows the suture 20 advancing along a path to push against the needle 5. FIG. 5d shows the suture 20 advanced along the path. FIGS. 5e and 5f show the suture 20 advanced along a return path. FIG. 5g shows the path re-set. FIG. 5h shows suture twist. FIG. 5i shows suture weld. FIG. 5k shows the suture twister 60 moved forward to activate a suture cutting blade 80. FIG. 5l shows suture twister 60 moved back to allow the cutting blade 80 to retract. FIG. 5m shows the needle 5 rotated back to the retracted configuration leaving the suture loop 21 in place.

FIG. 6a illustrates the needle 5 in the extended configuration rotated out at the distal end of the housing. The distal opening of the housing 2 is covered in with a flap 95.

Figure 6B:
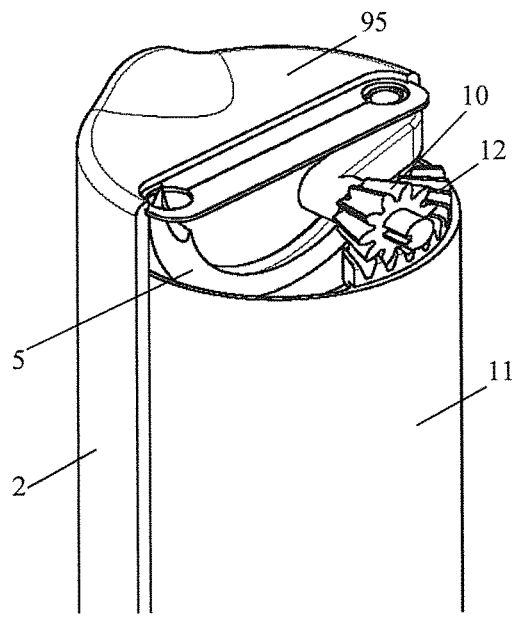
Figure 6C:
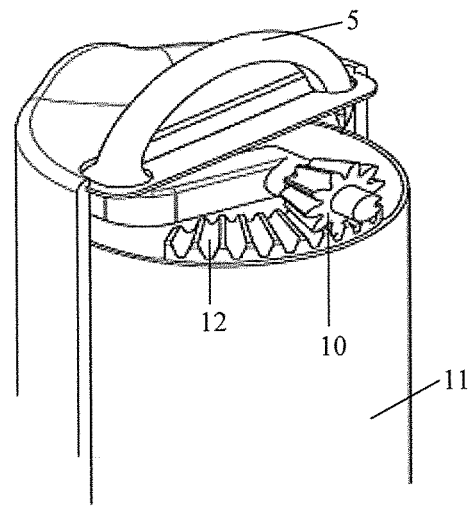

FIGS. 6b and 6c illustrate the needle 5 with a cog 10 which is driven by a gear 12 on the internal shaft 11 which turns to drive the needle 5.

Figure 6D:
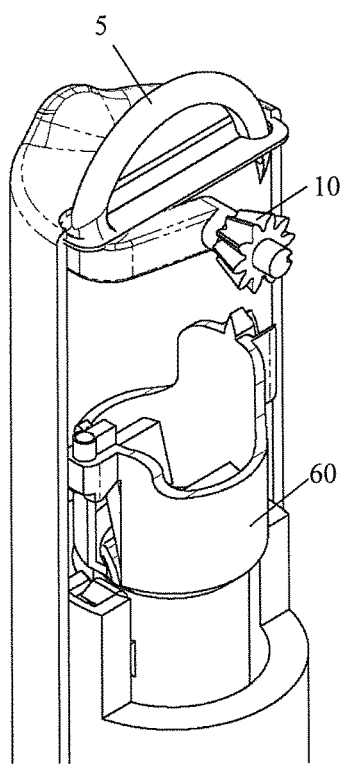
Figure 6E:
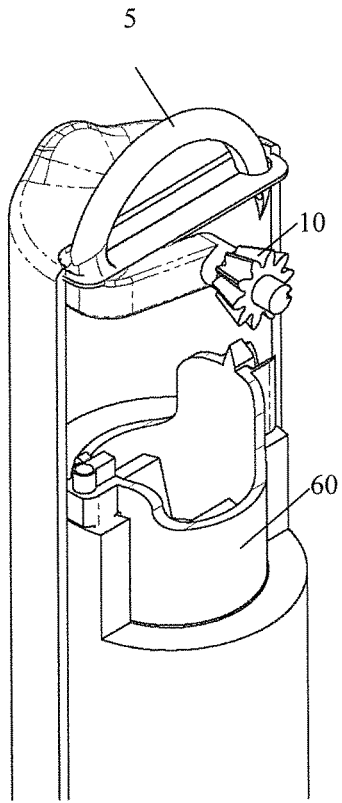
Figure 6F:
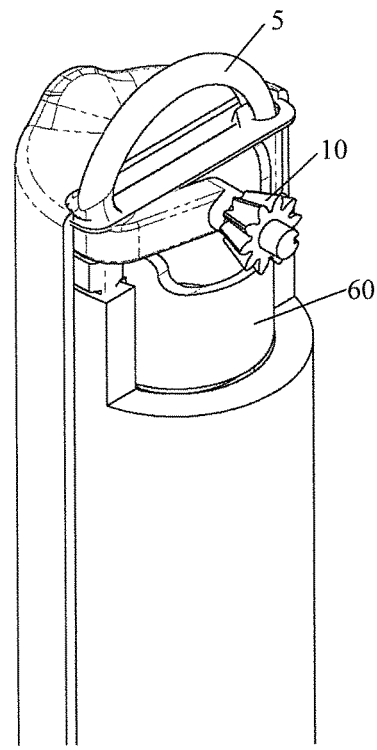

FIGS. 6d, 6e and 6f show the suture guide advancing to capture the suture twist component 60, and proceeds until the twist component 60 meets the needle 5. The suture 20 will then advance up and around the needle 5.

Figure 6G:
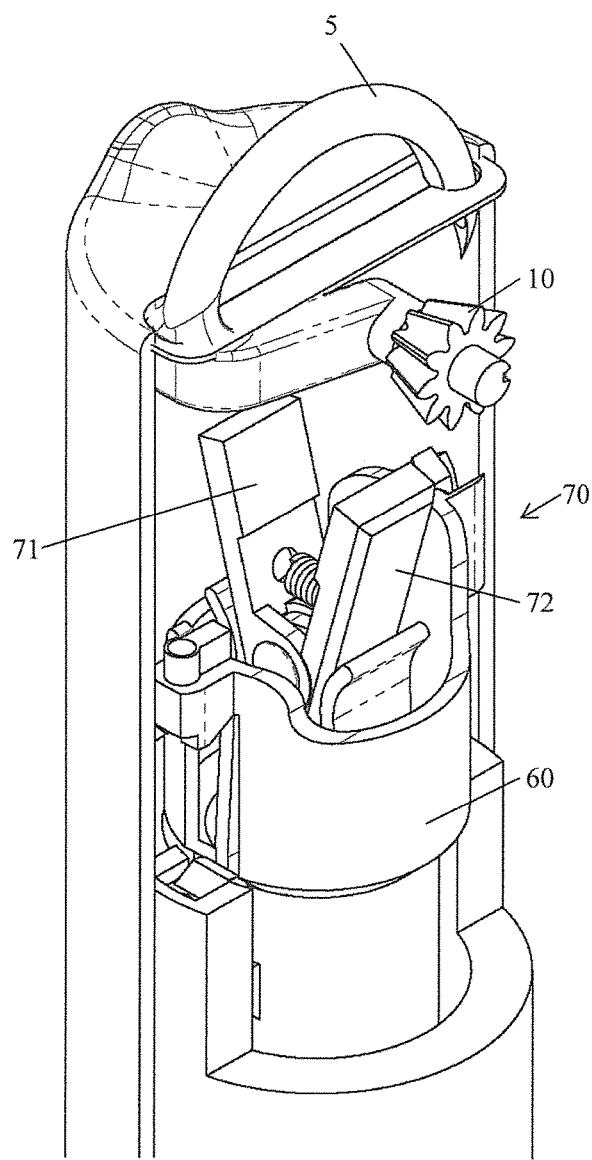

FIG. 6g shows the twist component 60 twisting the suture 20 before melting. The twists may be between 180 degrees to 540 degrees. Once twisted, the melting element 70 advances. Heat may be generated in any suitable manner. For example, a current may be passed through a metal shim that acts as a resistor. An ultrasonic system could also be used.

Figure 6H:
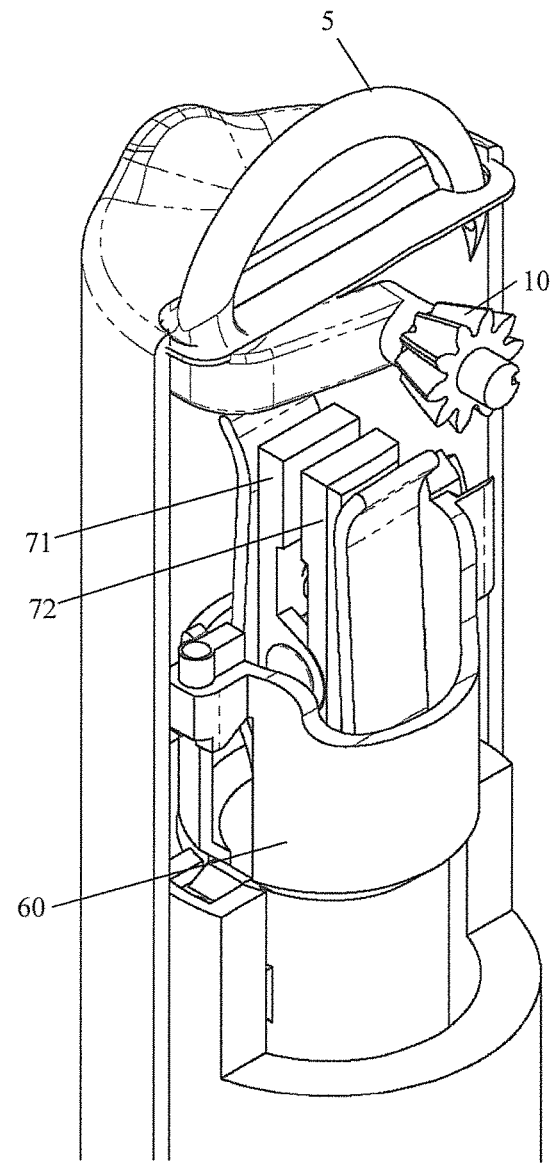
Figure 6I:
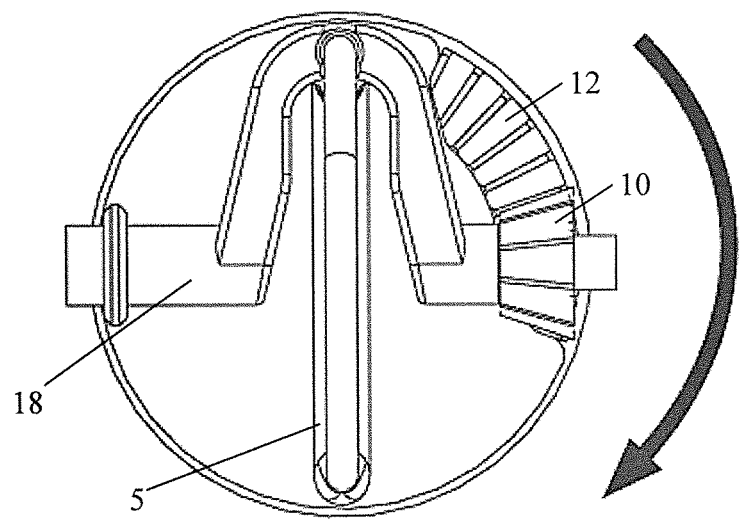
Figure 6J:
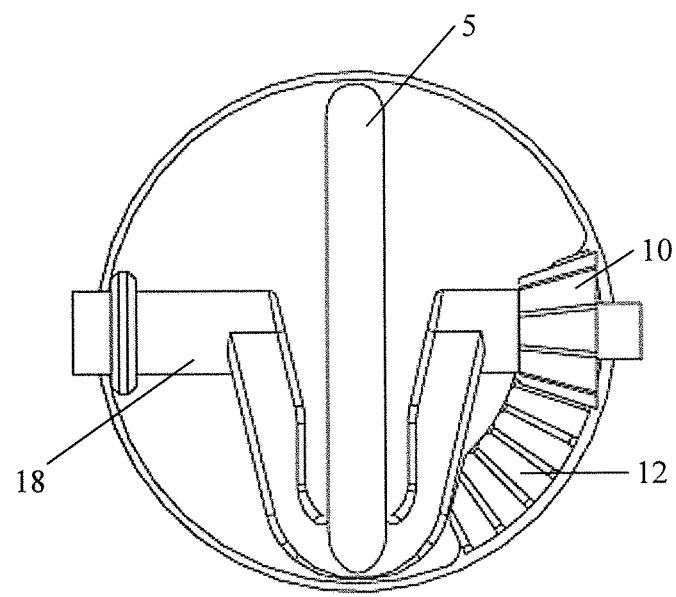

FIGS. 6i and 6j are plan views which illustrate the needle in a retracted (FIG. 6i) and advanced (FIG. 6j) positions.

Figure 6K:
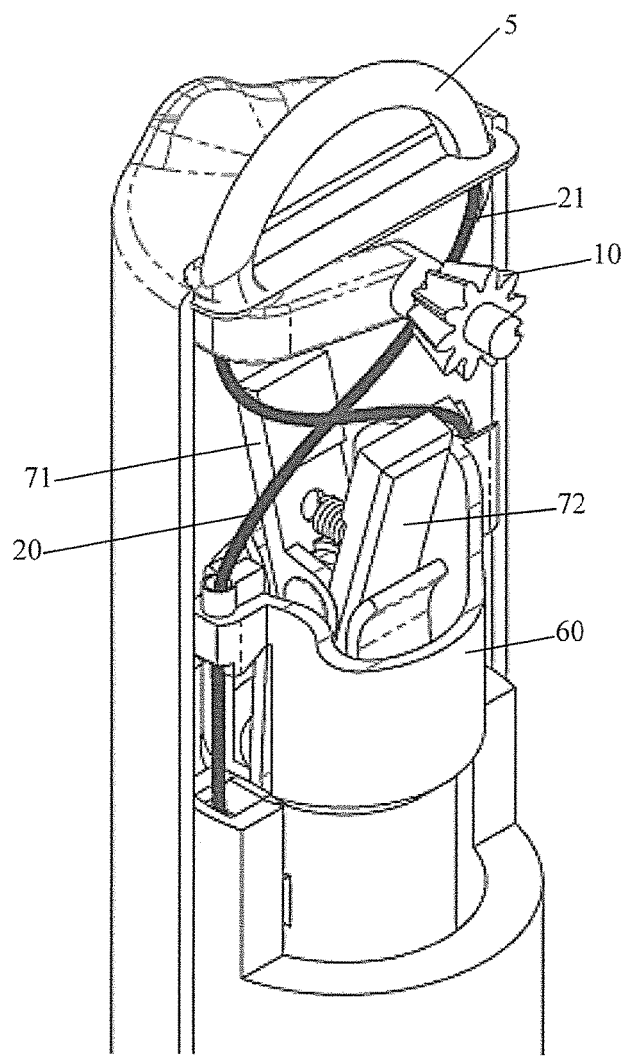
Figure 6L:
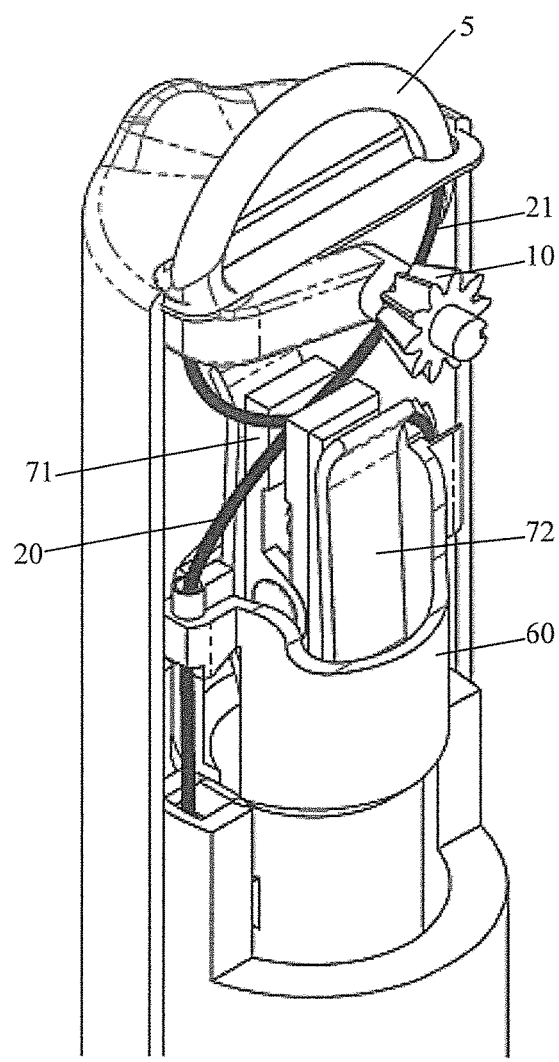
Figure 7A:
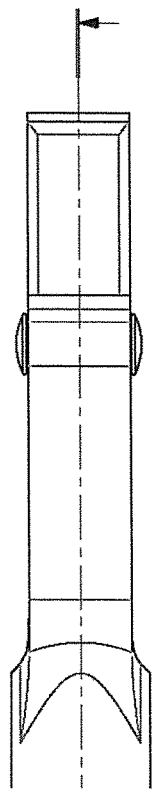
FIGS. 7a to 7f are views of a suture clamping and heating system used in the suture device.
Figure 7B:
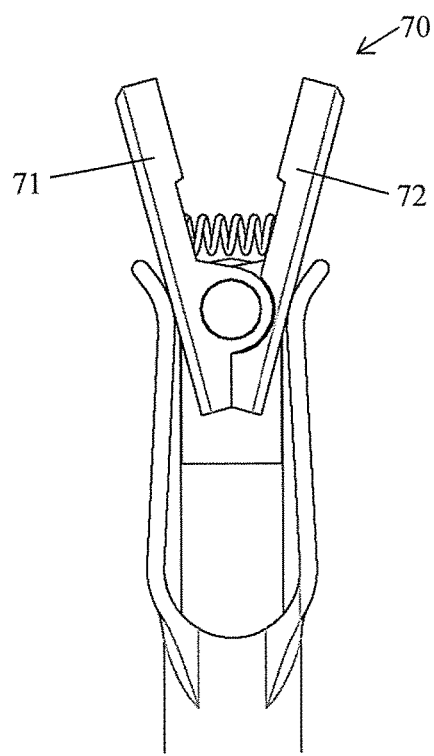
Figure 7C:
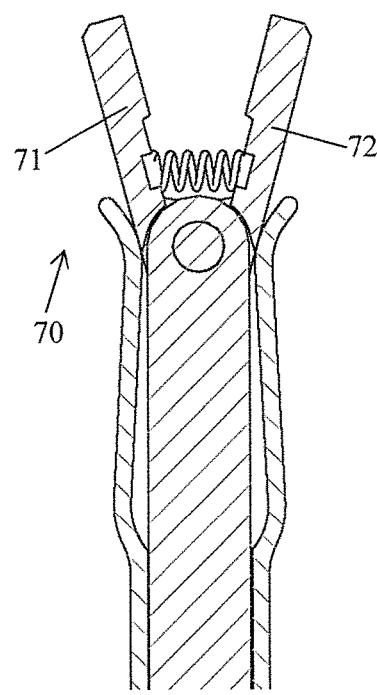
Figure 7D:
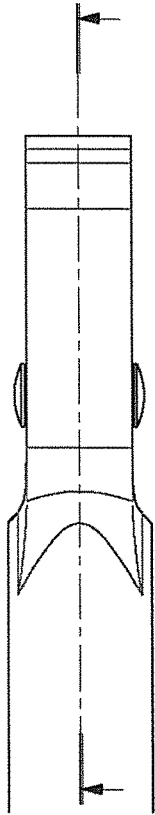
Figure 7E:
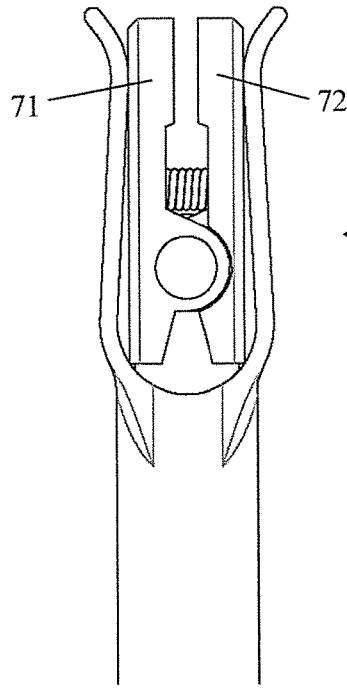
Figure 7F:
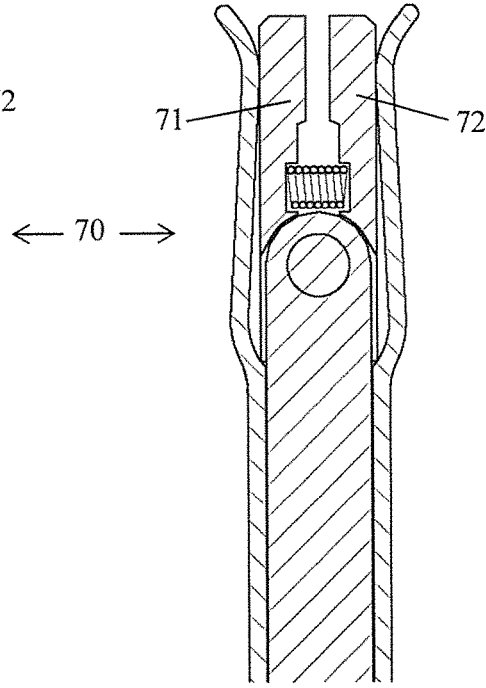

FIGS. 6k and 6l are the same views as FIGS. 6g and 6h but with a suture 20 in place.

FIGS. 7a to 7f illustrate heated clamp plates 71, 72. The temperature to which the plates 71, 72 are heated may be adjusted depending on the type of suture being used. The heated plates 71, 72 are then pressed down onto the suture overlap 22 leaving a gap of typically about 0.5 mm. The shape/profile of the heated plates 71, 72 can vary from flat, parallels plates, to curved plates, to angled to a point.

FIGS. 8 to 12 illustrate a 3D printed needle 5 with integrated gear 10 or assembled with gear 10. The needle 5 may be printed in metal such as titanium or stainless steel. The external surface of the curved needle 5 and the axle shaft 18 may be polished to a smooth finish. The internal surface of the suture path can be polished, left unfinished or smoothed using an etching laser process that generates a subtle melt on the surface to remove the texture.

Figure 8:
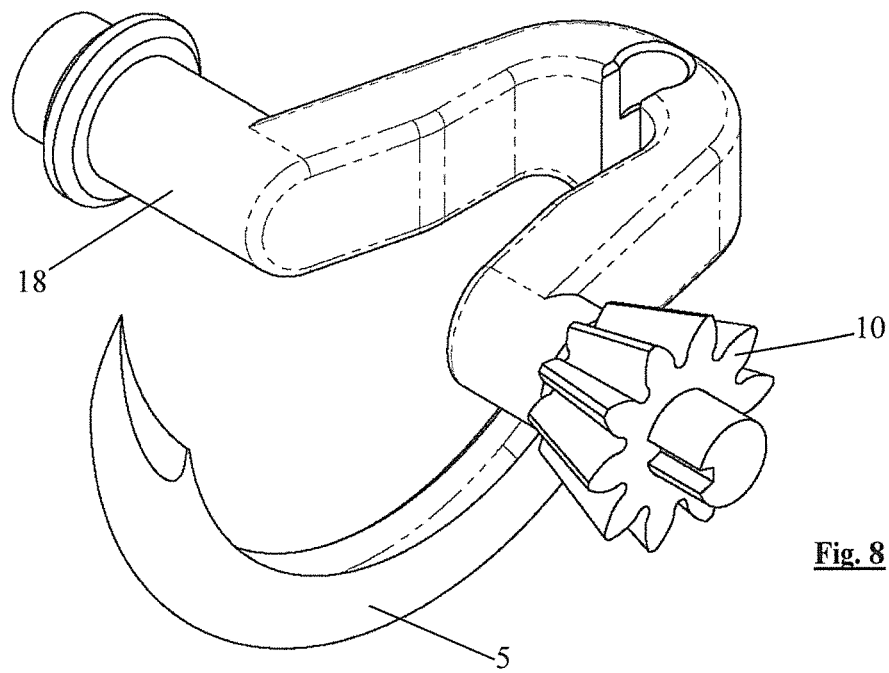
FIGS. 8 to 12 are views of a suture needle part of the suture device.
Figure 9:
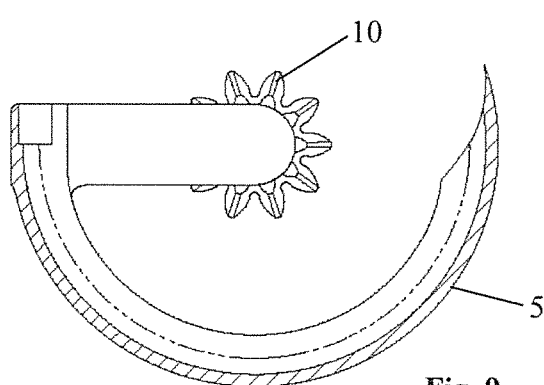
Figure 11:
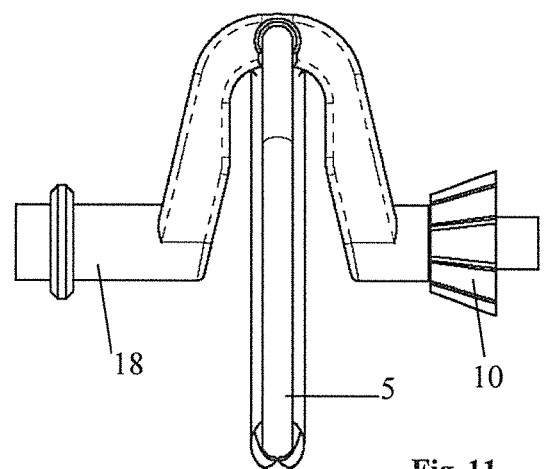
Figure 10:
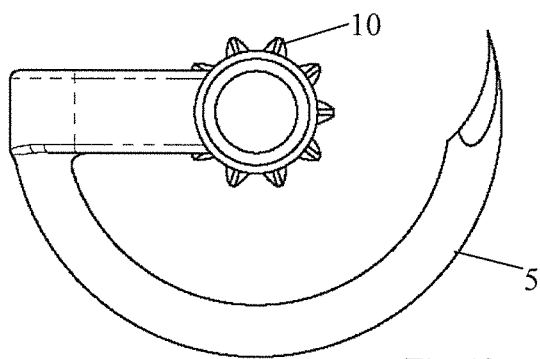
Figure 12:
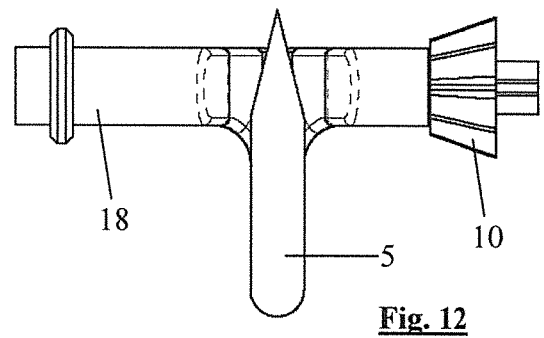

Referring for example to FIG. 8, in one case the needle is manufactured by 3D printing as one unit or two separate 3D printed parts attached. Alternatively the needle may be manufactured by metal injection moulding. The needle in some cases may be of a ceramic or any suitable composite or combination of materials. In some cases the needle is manufactured using an over moulding technique.

The needle is preferably driven using a mechanical gear system to ensure effective and reliable operations. The gear system is ideally of metal and/or ceramic for enhanced strength. In one case the gear system is a sector gear (also known as a crown gear or rack)/pinion-gear combination. The system illustrated may be referred to as a rack and pinion system.

Figure 13:
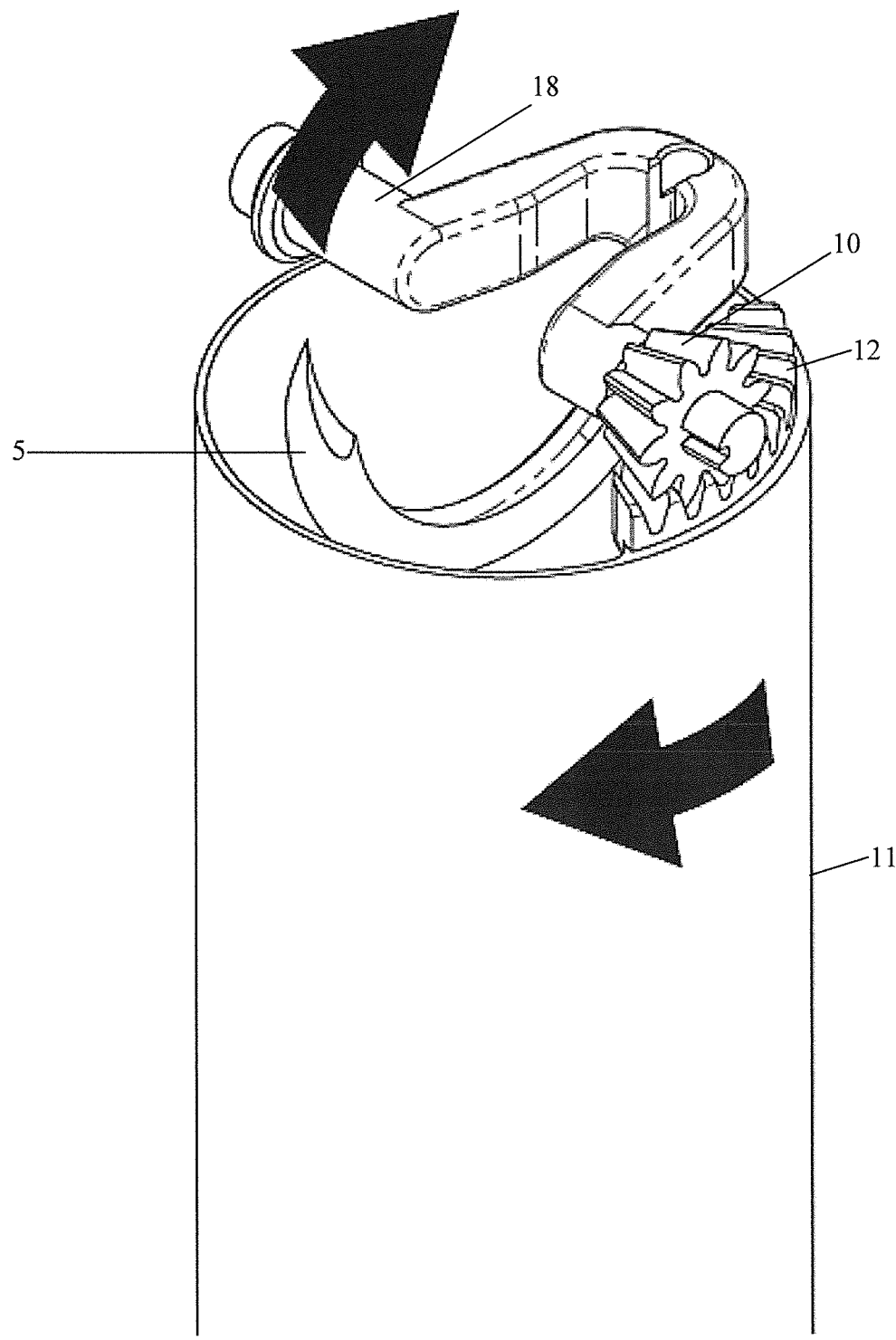
FIGS. 13 to 15 illustrate the distal end of the suture device with the suture needle part in different configurations.

Referring to FIG. 13, the gear 10 on the needle 5 is a bevelled gear which is turned by a sector gear 12. The sector gear 12 is mounted at the top of the shaft 11. The shaft 11 is rotated by a motor in the handle 3 of the device. The gear ratio may be modified to provide the required mechanical force. In one case, the shaft 11 rotates 60 degrees to achieve a 180 degree rotation of the needle 5. The needle 5 rotates back when device activation has been completed.

The system of the invention gear provides a highly efficient way of transferring torque from the motor, along the shaft and into the needle. The components are typically a mixture of metal and hard plastics and no force or movement is lost. A problem with an alternative cable or wire operated system is that even a very small amount of stretch of the cable or wire translates into a significant loss of rotational movement in the needle. 1:1 is the most efficient gear ratio. However, in the illustrated case the ratio is 1:4 which means the sector gear is rotating 90 degrees to achieve a 180 degree rotation on the needle. The sector gear is thereby relatively short which avoids any interference with the movement of the needle.

If the device has a fixed bend or a curve in the shaft, then the internal shaft with the sector gear may include a feature to transfer twisting force across the bend. By utilising a spring at the bent section of the tube, the force is transferred across the bend. This spring design would also function in an articulating head which facilitates use with robotic systems. Alternatively or additionally, the shaft may have a bend or curve to increase the degree to which the device can be manipulated in use.

Figure 14:
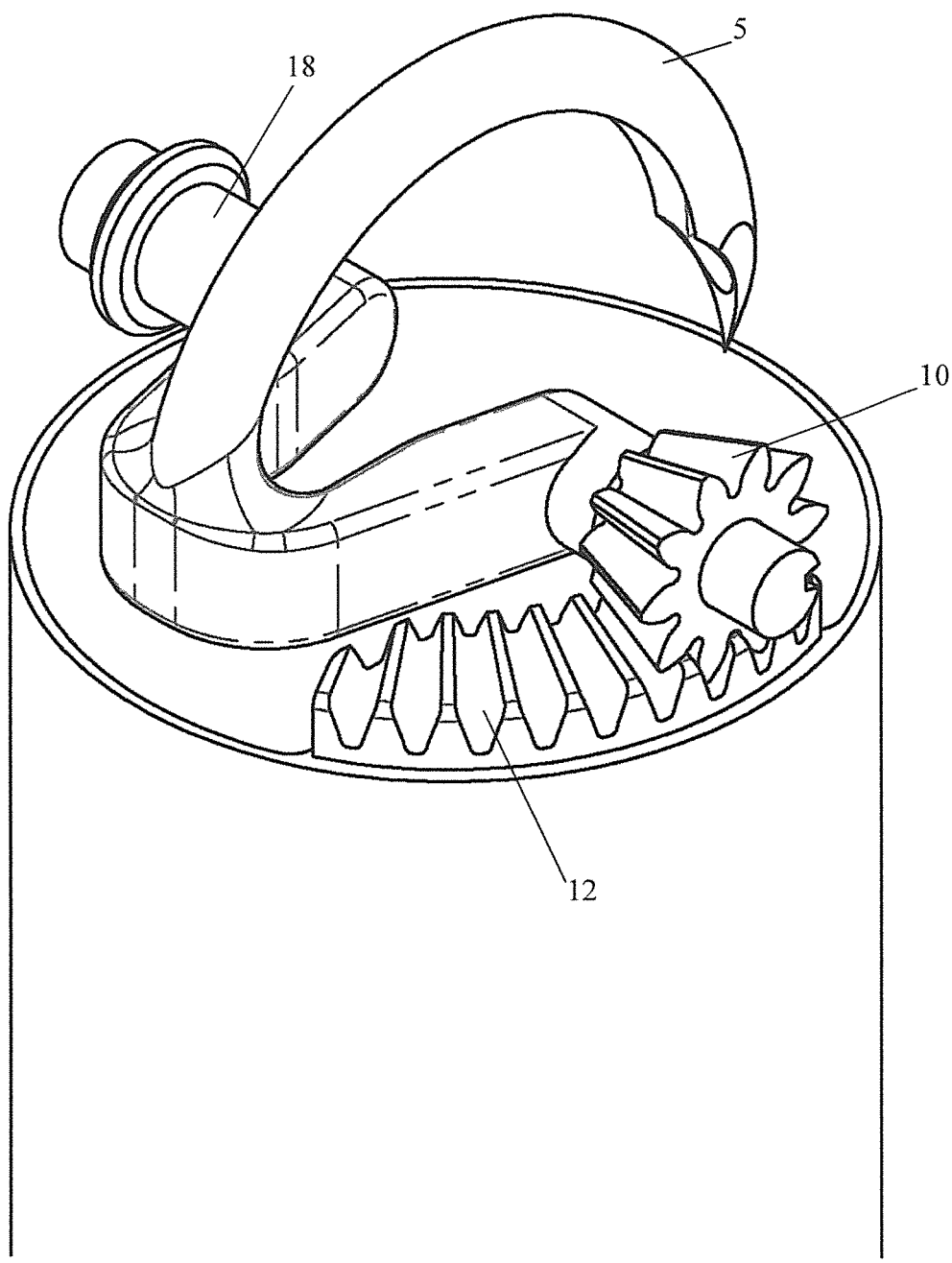

FIG. 14 shows the needle 5 in its deployed position.

Figure 15:
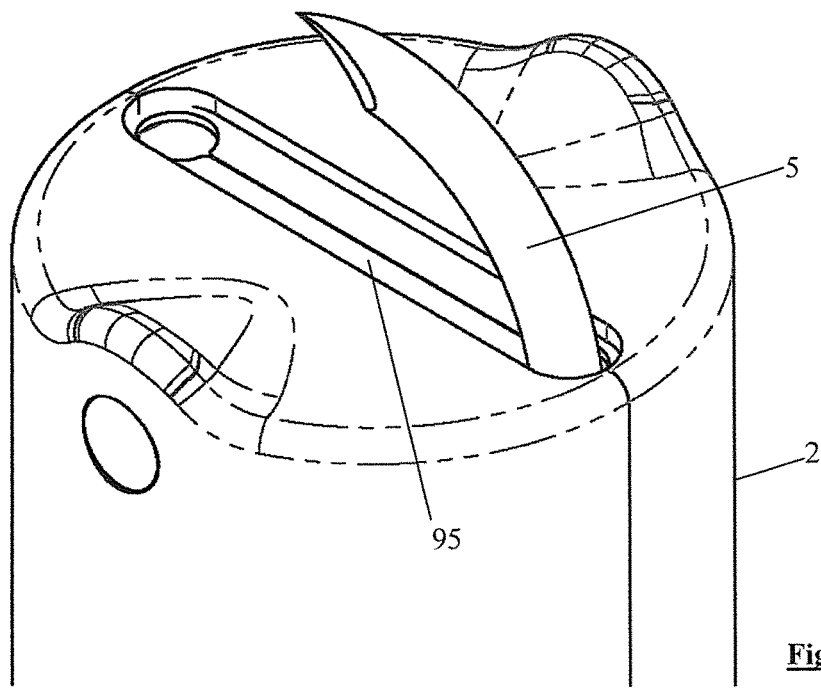
Figure 16:
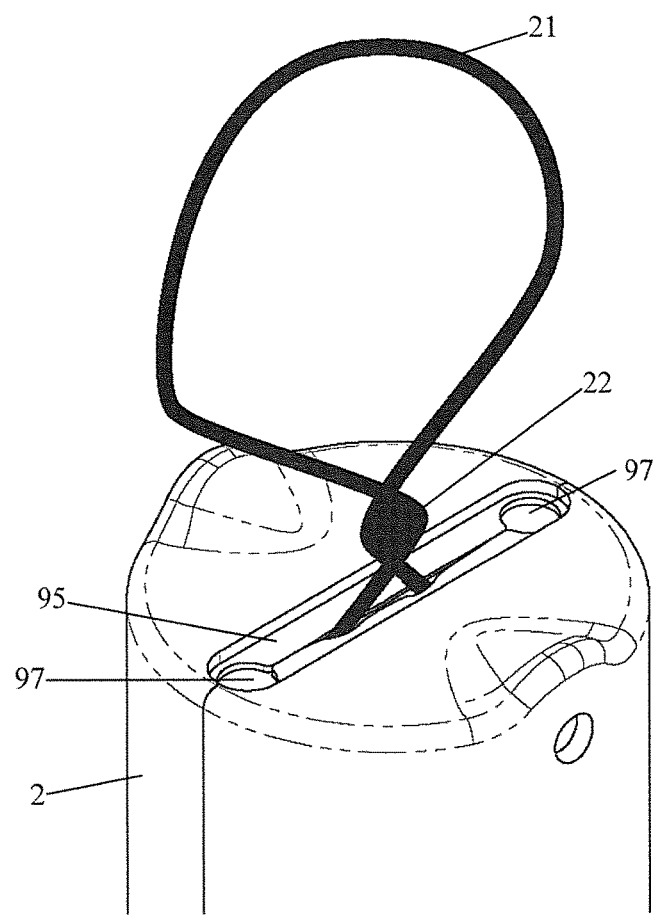
FIG. 16 illustrates the suture device and a suture loop passing through the flap and the flap deforming.

Referring to FIGS. 15 and 16, at the opening of the distal end 4 of the device, there is a flexible flap 95 to prevent ingress of material into the device. The needle 5 passes through this flap 95 and into the tissue. Once the suture loop 21 has been put into place, it can then be pulled back out through the flap 95.

Referring to FIG. 16 it will be noted that the flap 95 deforms around the melted section of the suture to prevent debris entering the device during withdrawal of the suture loop from the device. Open areas 97 at each end of the flap prevent the flap from blunting the needle as it rotates into and out of the housing.

Figure 17:
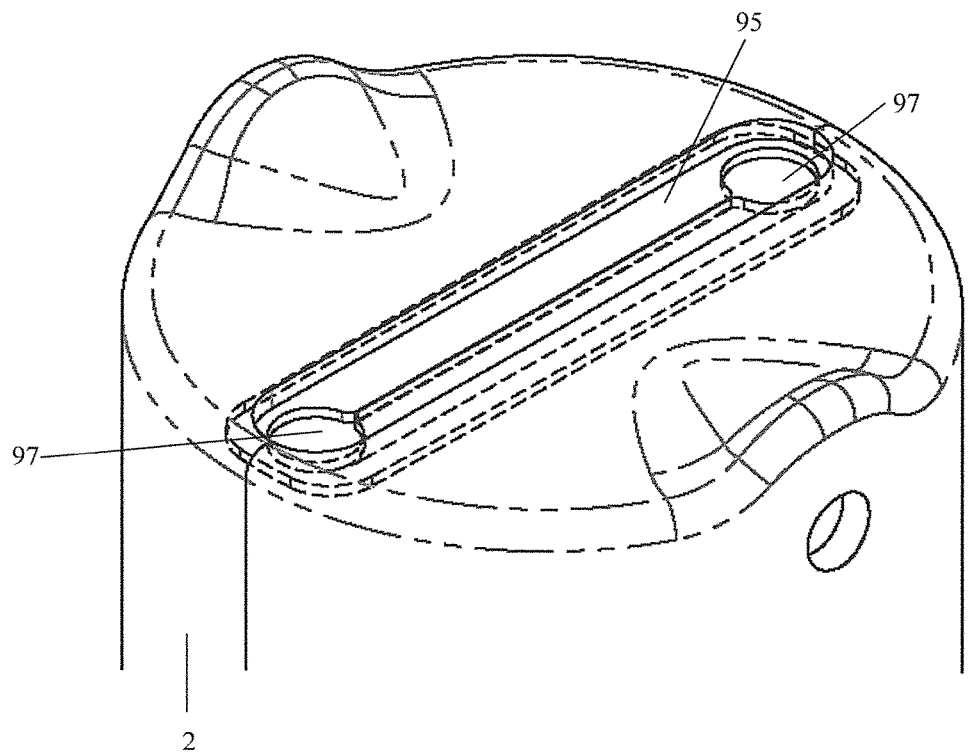
FIGS. 17 and 18 are views of a distal end of the suture device showing the flap.
Figure 18:
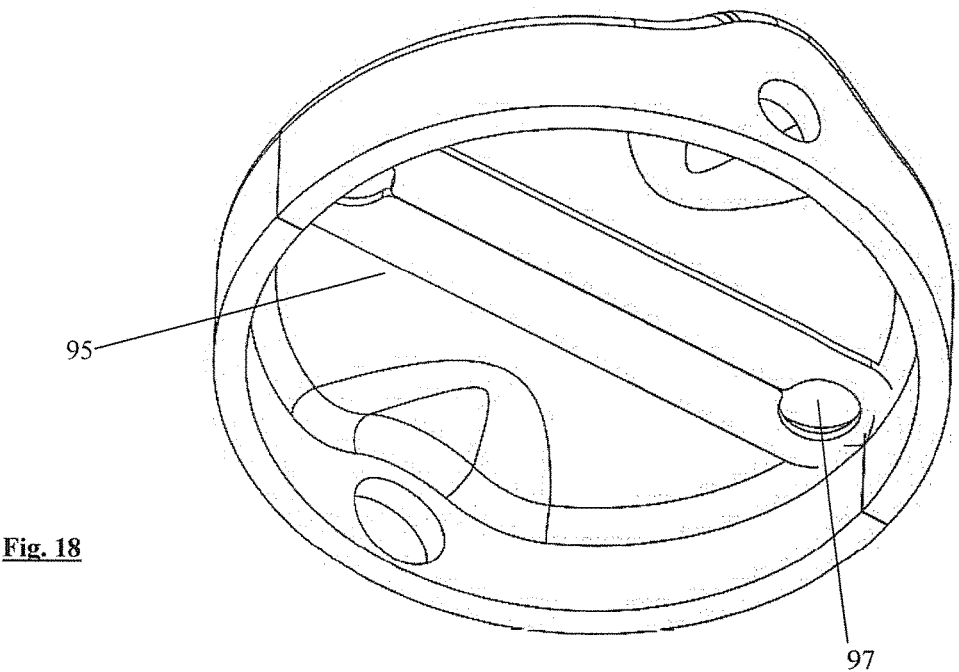
Figure 19:
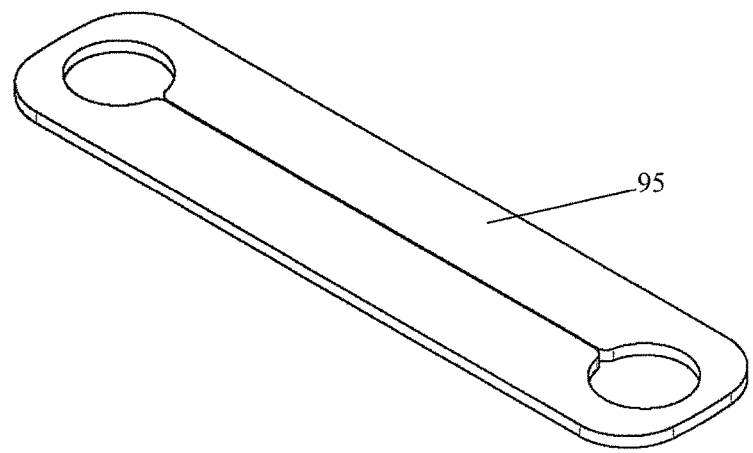
FIGS. 19 to 22 are views of various flaps for use at a distal end of a suture device.
Figure 20:
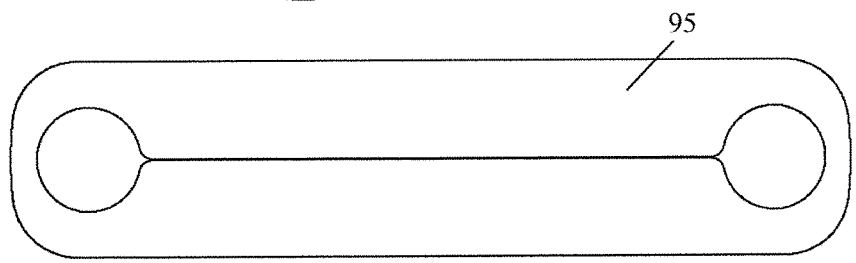
Figure 21:
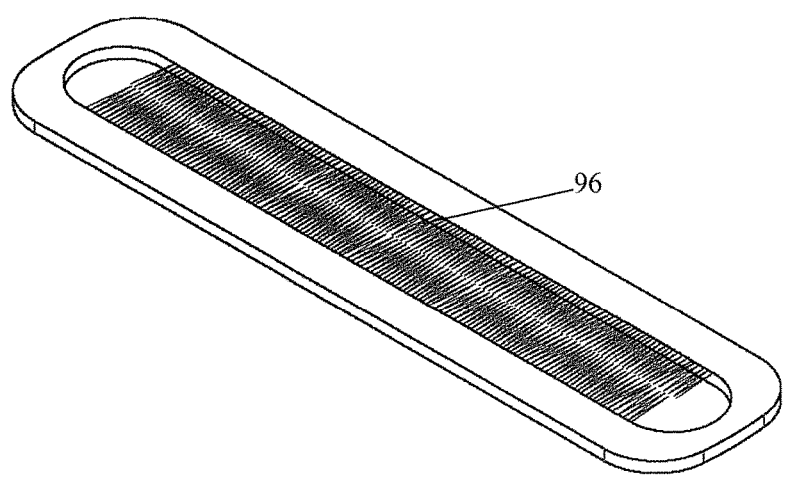
Figure 22:
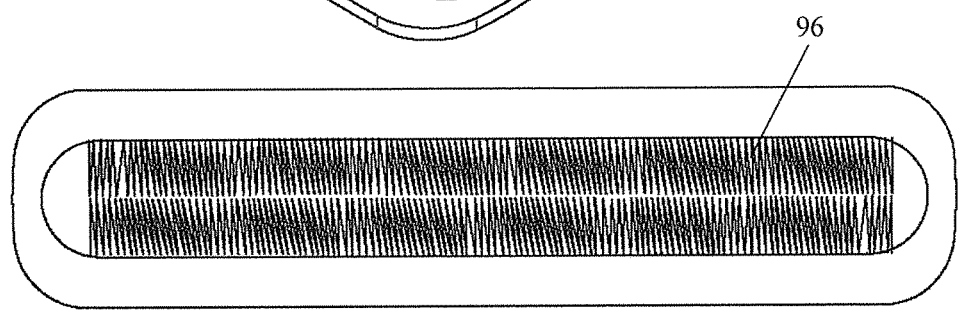

FIGS. 17 and 18 show the flap 95 fixed to the underside of the distal opening 4 in the housing 2.

FIGS. 19 to 22 illustrate that the flap 95 can be made of a flexible film or silicone and/or may comprise bristles 96.

Figure 23:
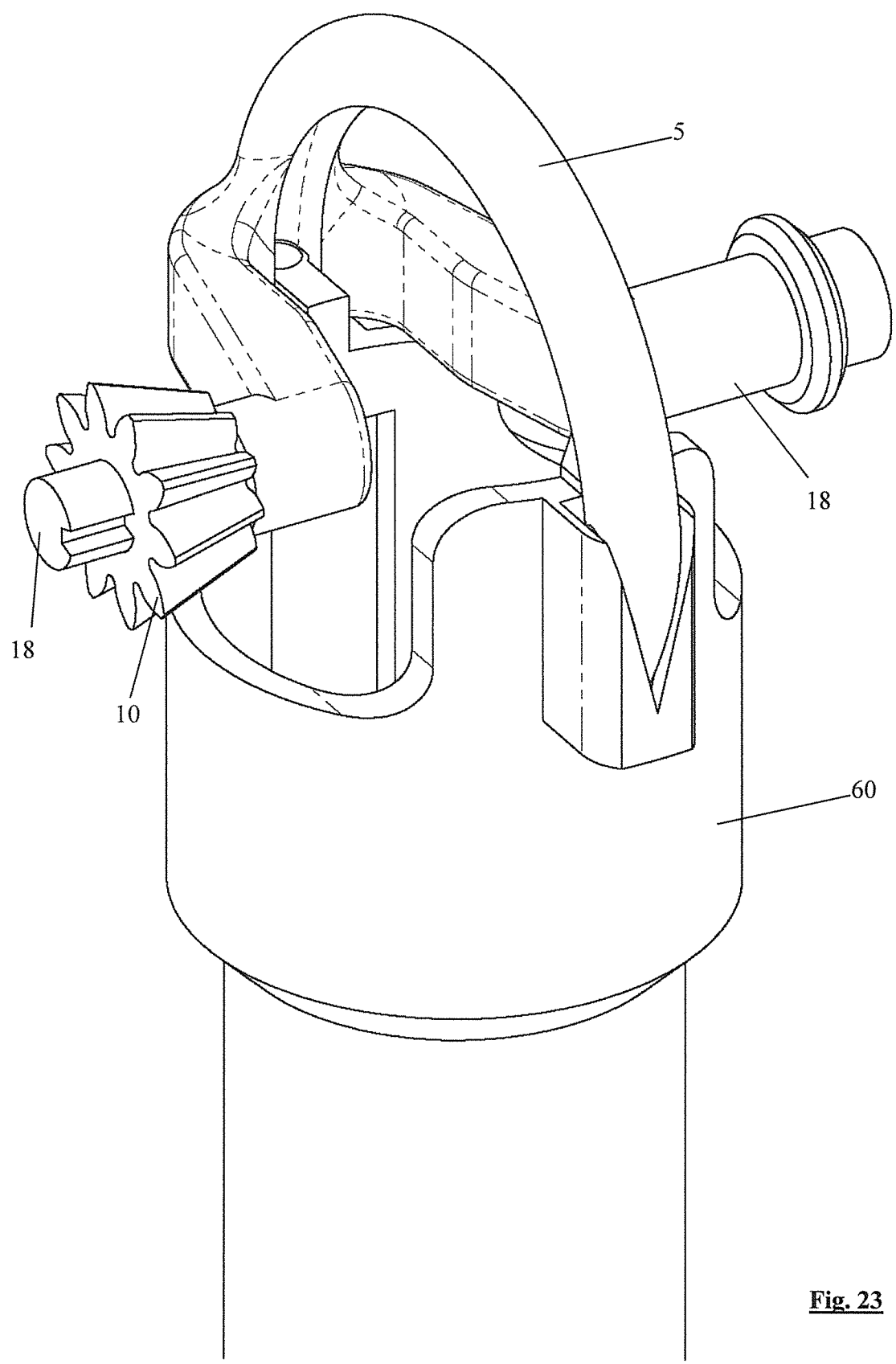
FIGS. 23 to 25 show details of the interaction of the suture needle and the twisting device.

Referring to FIG. 23, the twist element 60 of the device has features that engage with the needle 5 to ensure the needle 5 completely clears the tissue.

Figure 24:
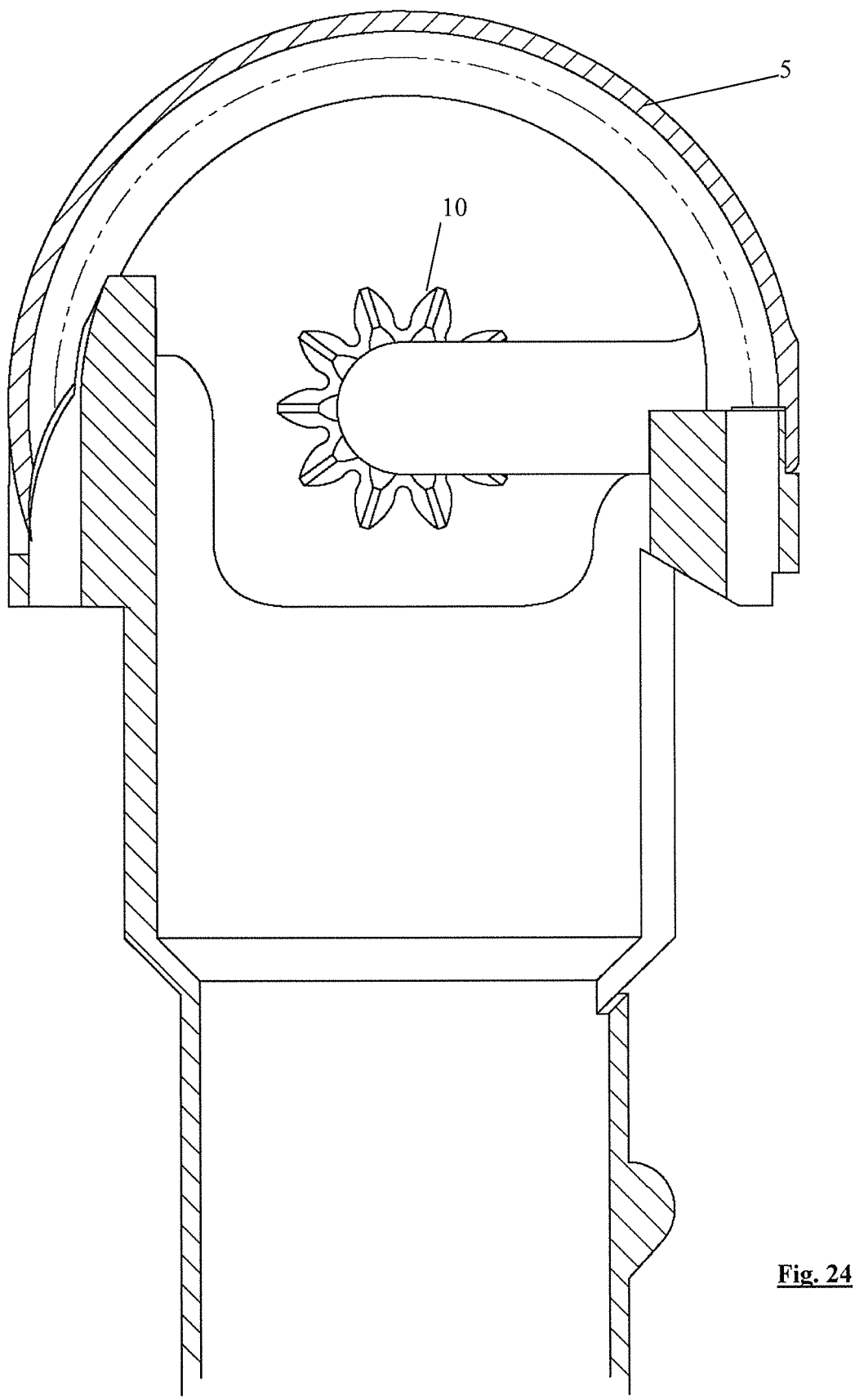
Figure 25:
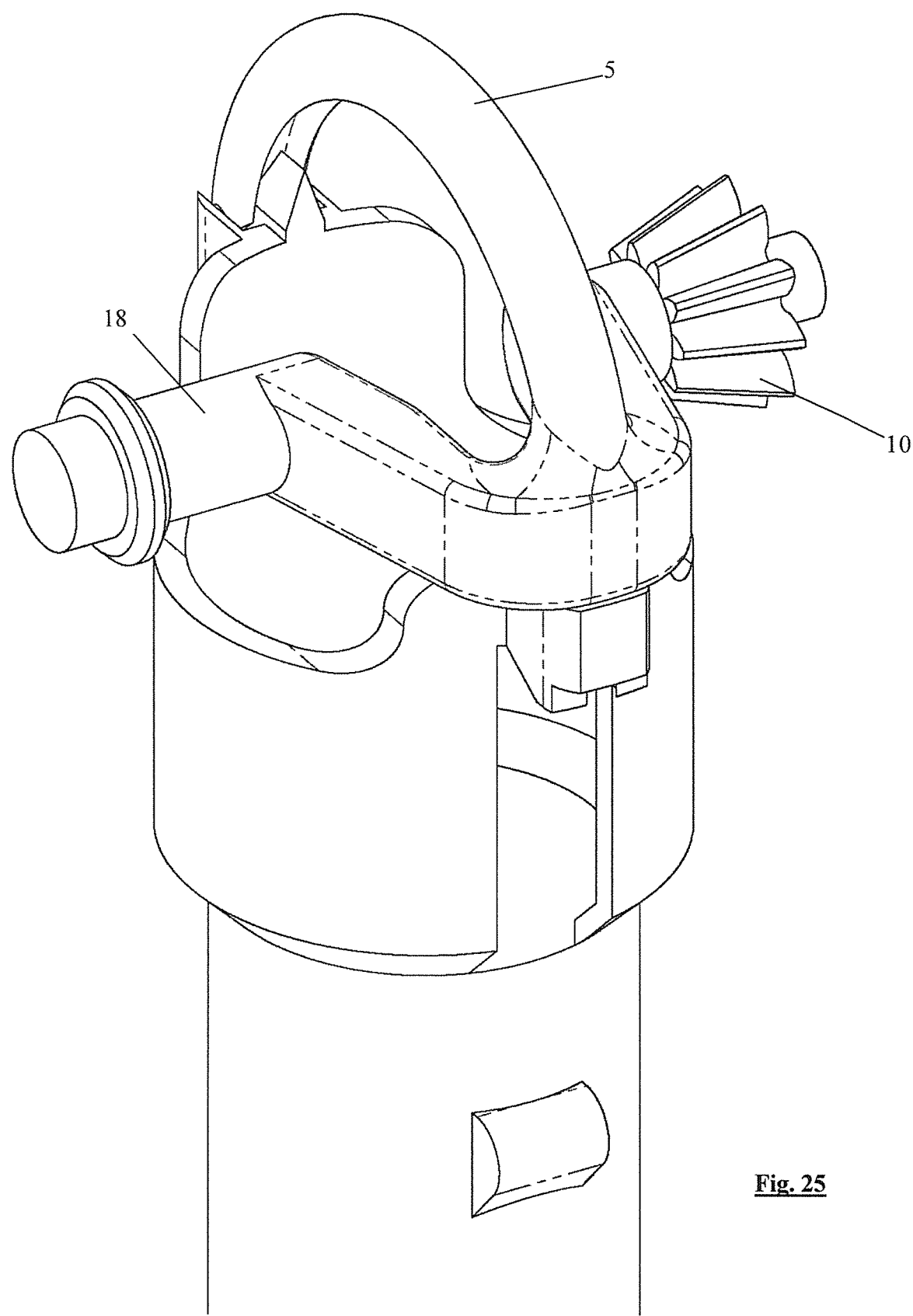
Figure 26:
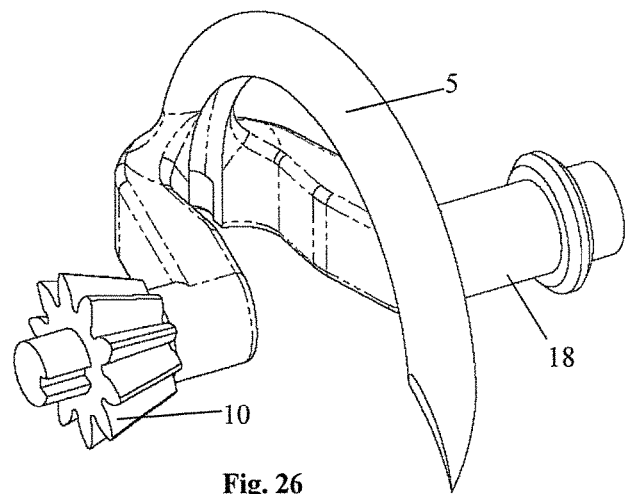
FIGS. 26 and 27 are further views of the suture needle.
Figure 27:
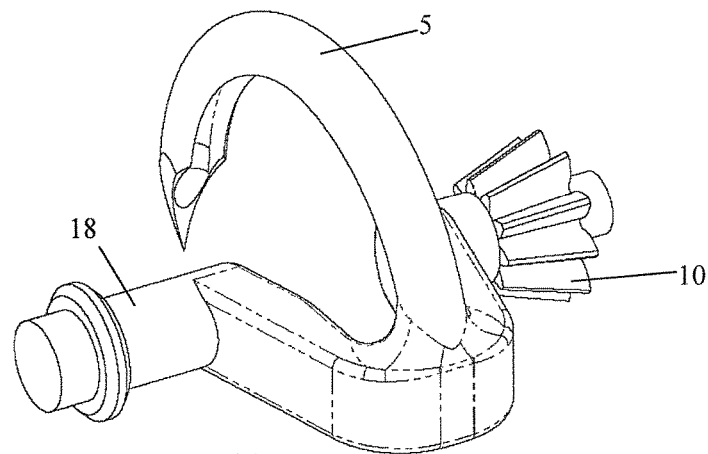

It will be noted from FIG. 24 that the end that engages with the needle tip has a sharp peak to push back any tissue that may be caught in the needle tip. The side from which the suture feeds has location bosses to ensure that the suture is guided into the needle channel.

Figure 28:
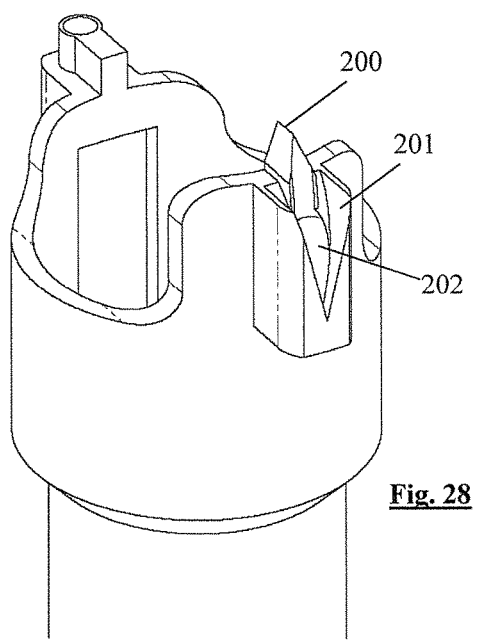
FIGS. 28 and 29 are views of a distal end of the suture device with the needle removed.
Figure 29:
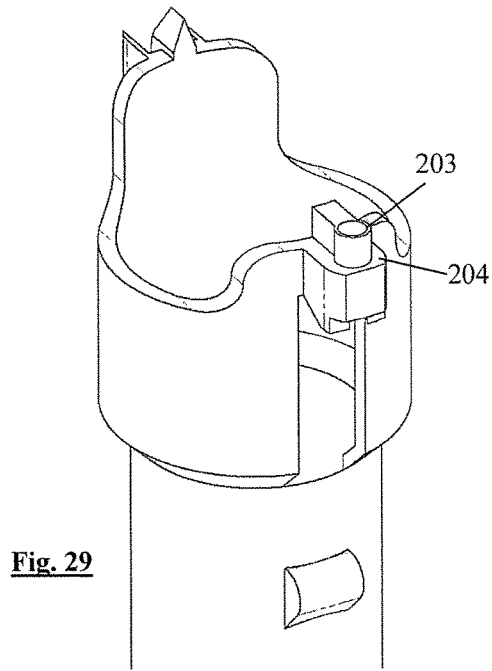

FIG. 28 is an enlarged view that shows the detail of the device in the region where the suture exits the feed channel. There is a protruding sharp edge tip 200 to aid the needle point in clearing tissue and the mesh. The channel 202 for receiving the suture is slightly larger in diameter than the needle channel. There is also a feature 201 for receiving the needle point to assist in aligning the internal channels of the needle and the suture feed channel. The deep V shape assists in guiding the needle so that the channels are aligned.

Figure 32:
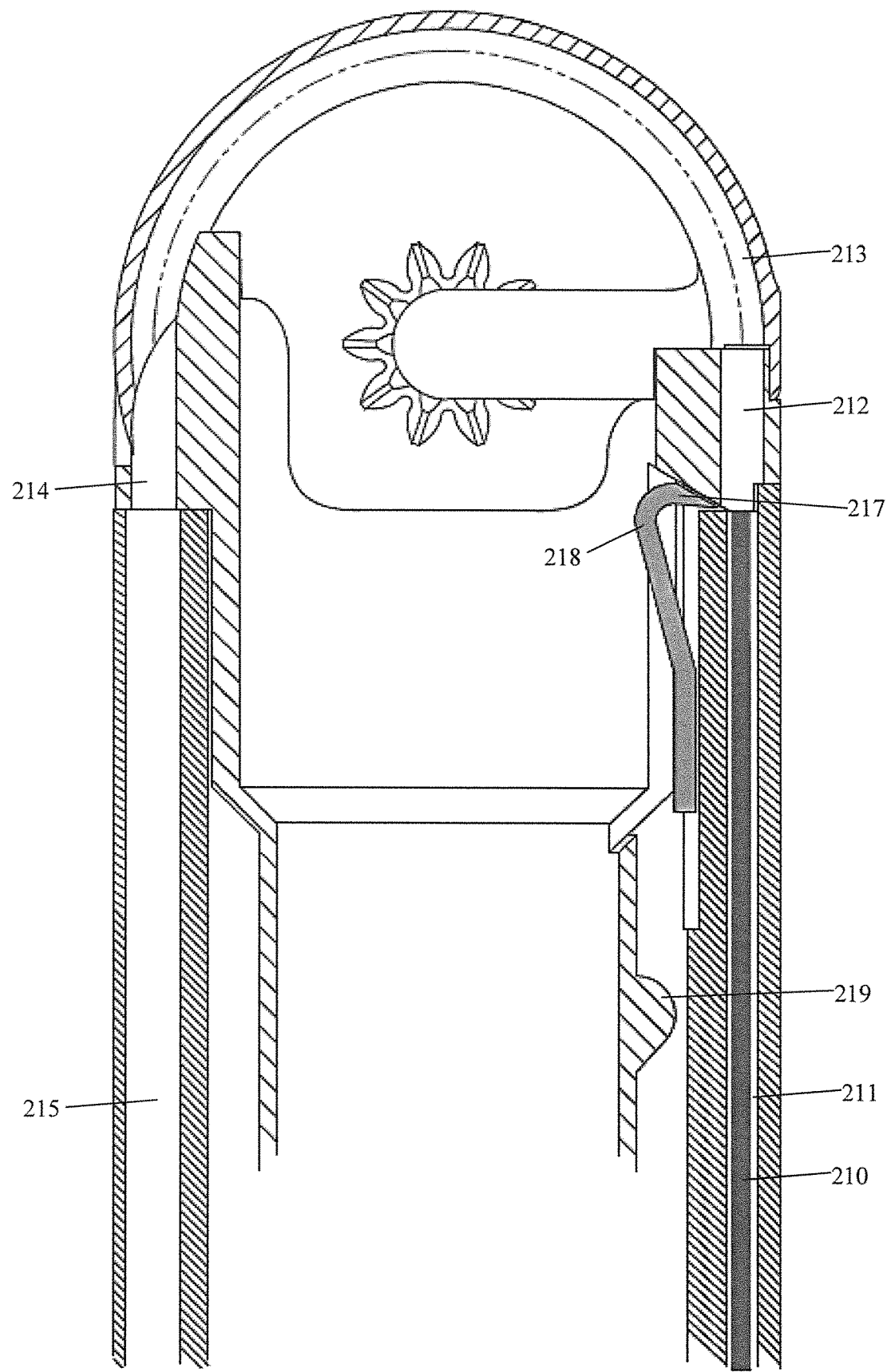

A feature 204 at the end of the feed section 211 of the channel ensures that the twister component correctly aligns with the needle. There is a recess 205 (as illustrated in FIG. 32) at the inlet end of the transition section 212 which aligns with and engages feature 204 of the feed section 211.

Referring to FIGS. 30 to 35 the various channels through which a suture 210 passes are illustrated on an enlarged scale. There are five different sections of this channel. The sections of the suture channels increase in diameter at each transition point to prevent snagging of the channels do not align perfectly. To aid with alignment of each channel, locating features are provided at each connection point.

| | |
|---|---|
| Feed section 211: | 0.6 mm internal diameter |
| Transition section 212: | 0.7 mm internal diameter |
| Needle channel 213: | 0.8 mm internal diameter |
| Transition section 214: | 0.9 mm internal diameter |
| Return section 215: | 1 mm internal diameter |

Channel 211 has a tight tolerance to ensure that a pushing force is transferred into advancement of the suture.

Figure 31:
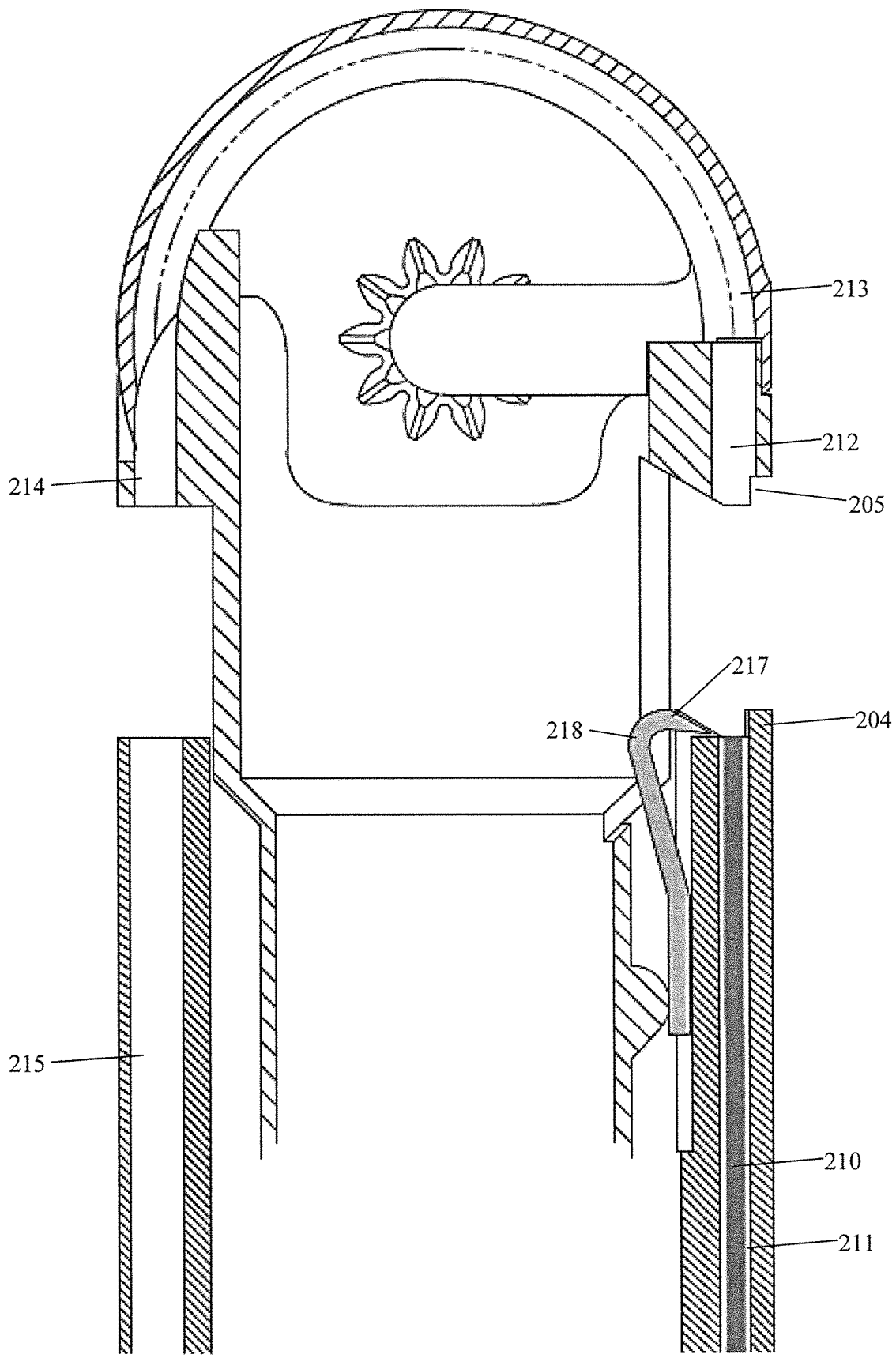
Figure 33:
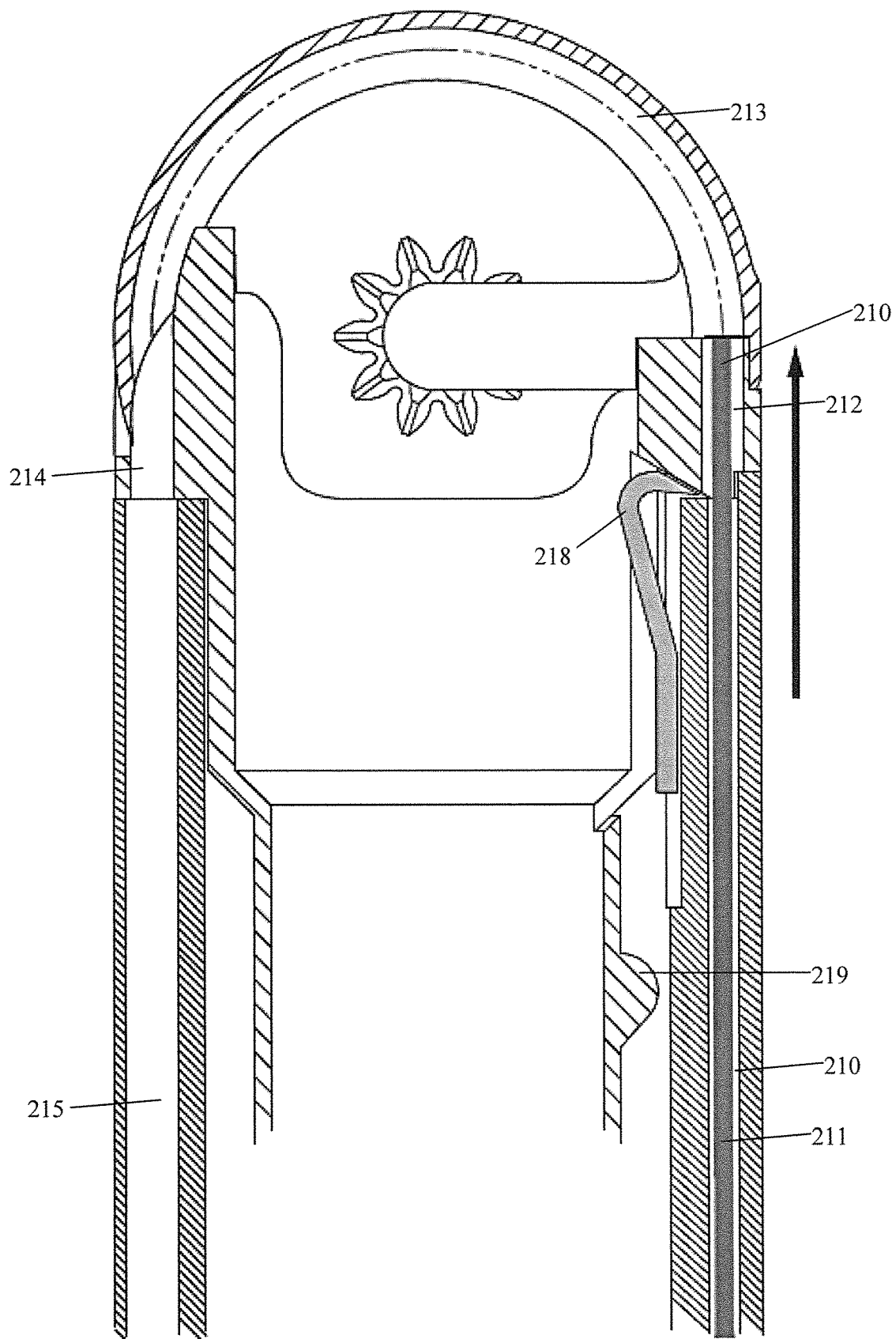
Figure 34:
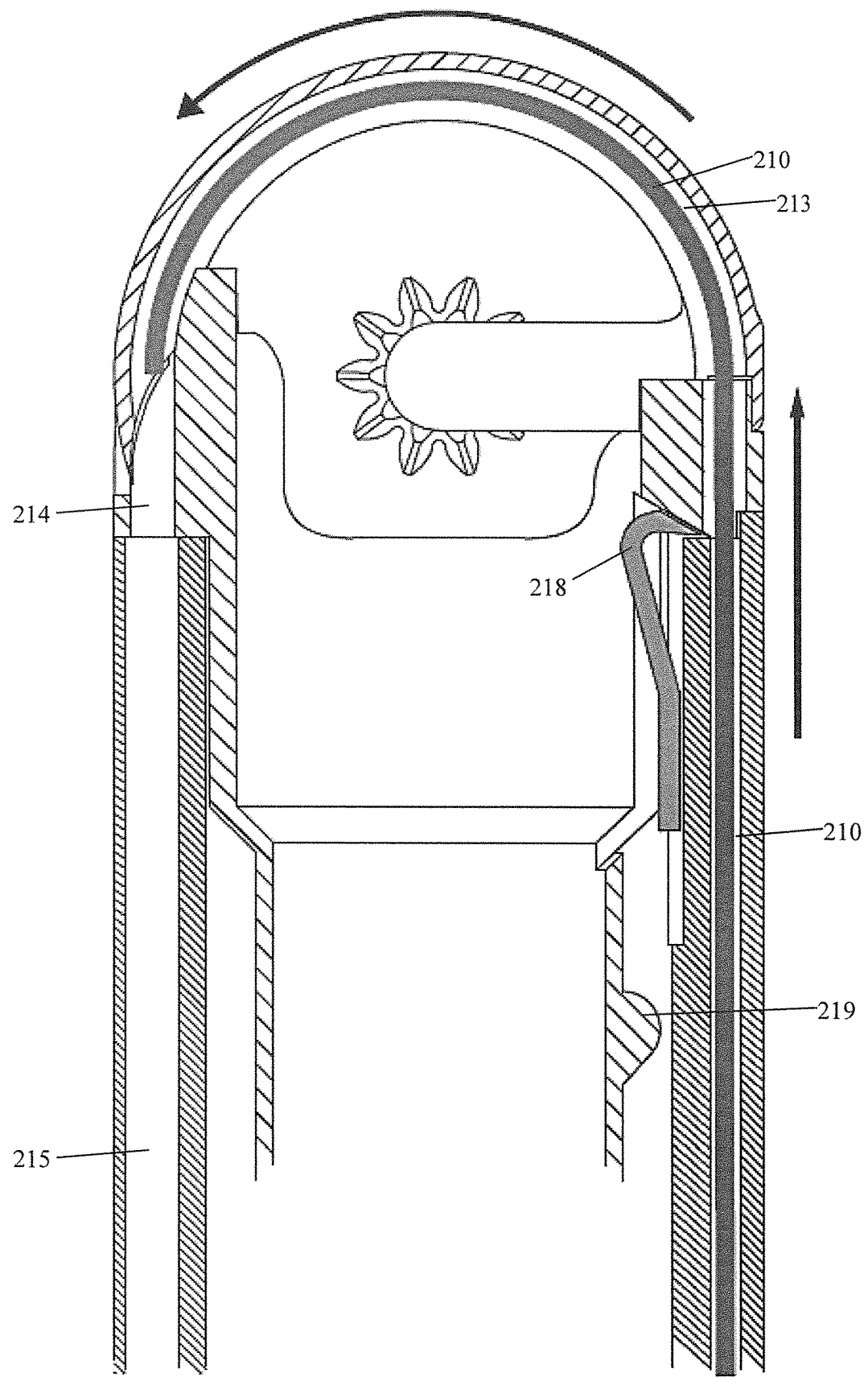
Figure 35:
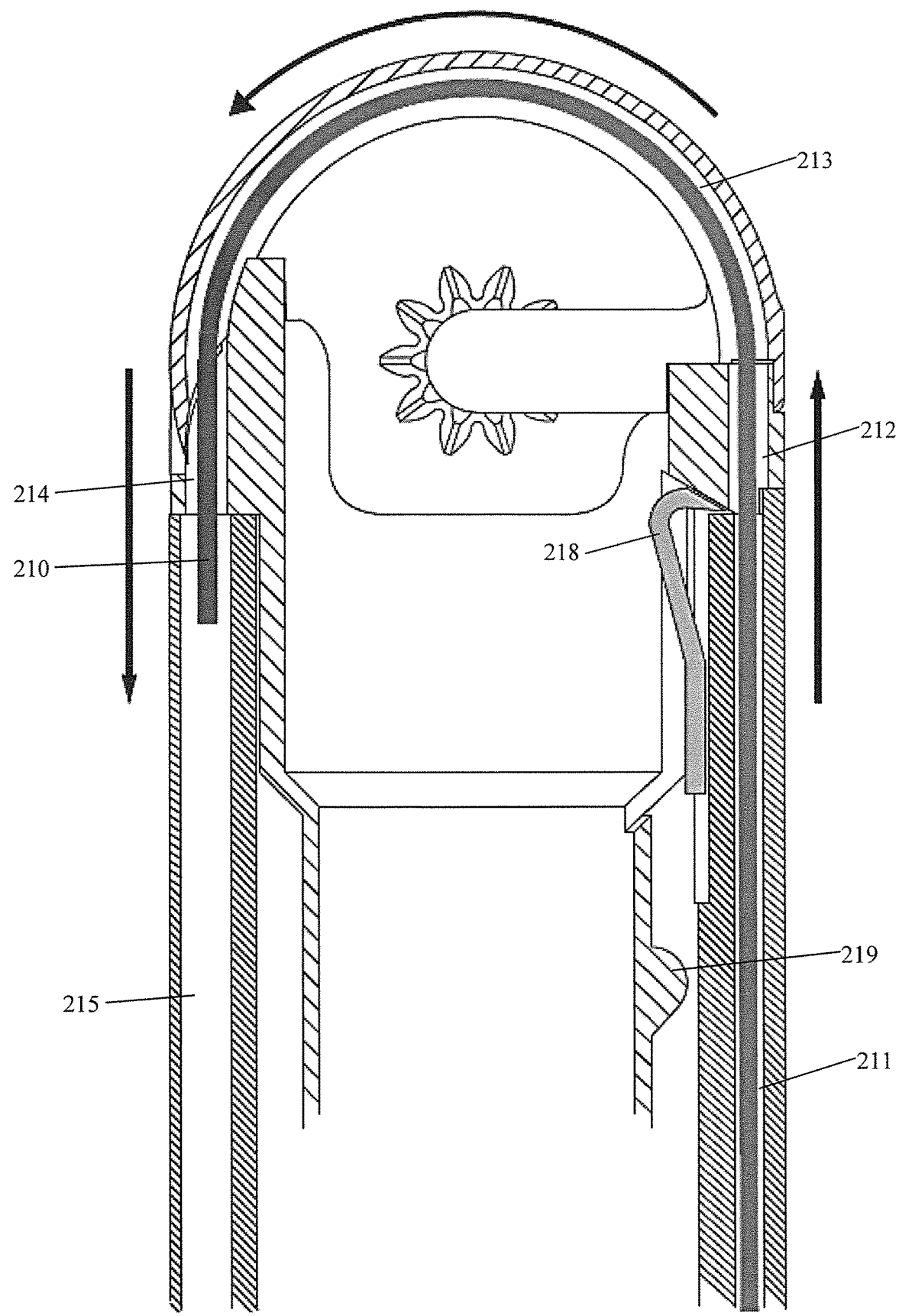

FIG. 31 illustrates that the twister and suture paths move towards the needle at the same time. The suture 210 advances as the suture path advances. FIG. 32 illustrates the twister stopped against the needle and the suture path continuing to advance. When the suture path is completed the suture 210 advances (FIG. 33). The suture then advances through the needle 213 (FIG. 34) and into the return section (FIG. 35).

Figure 45:
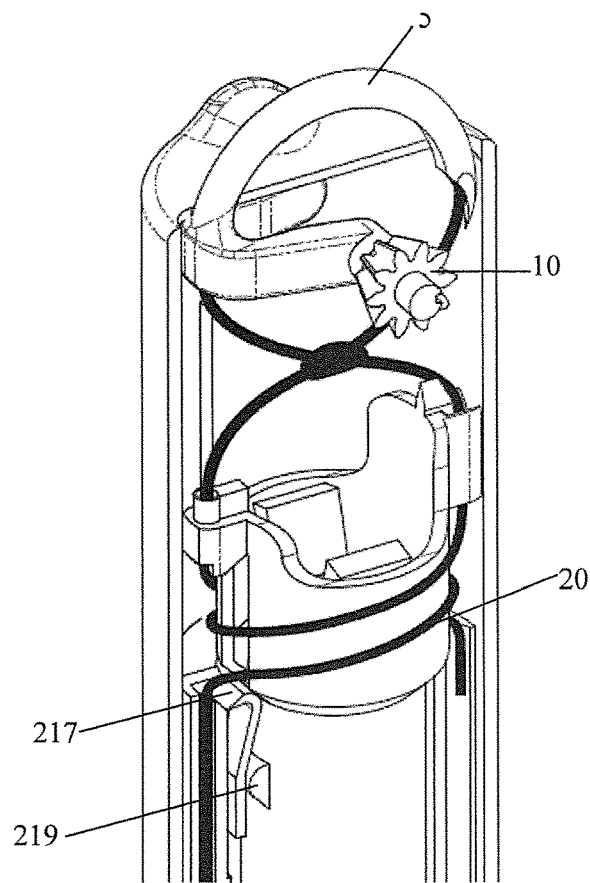
FIGS. 45 to 47 illustrate the suture being cut.
Figure 46:
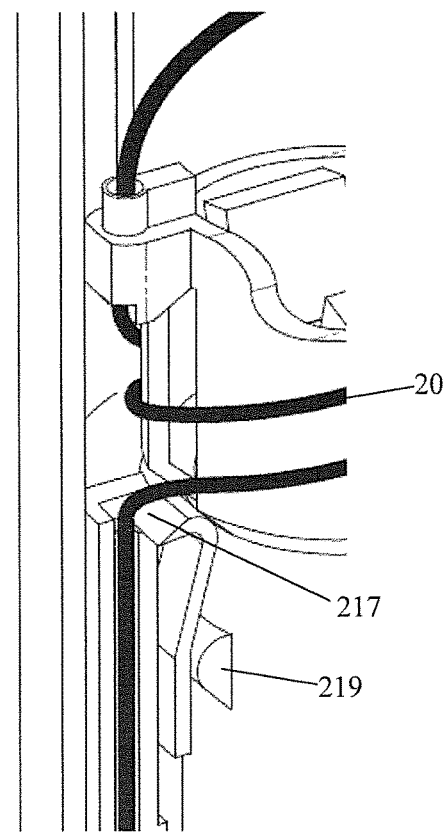
Figure 47:
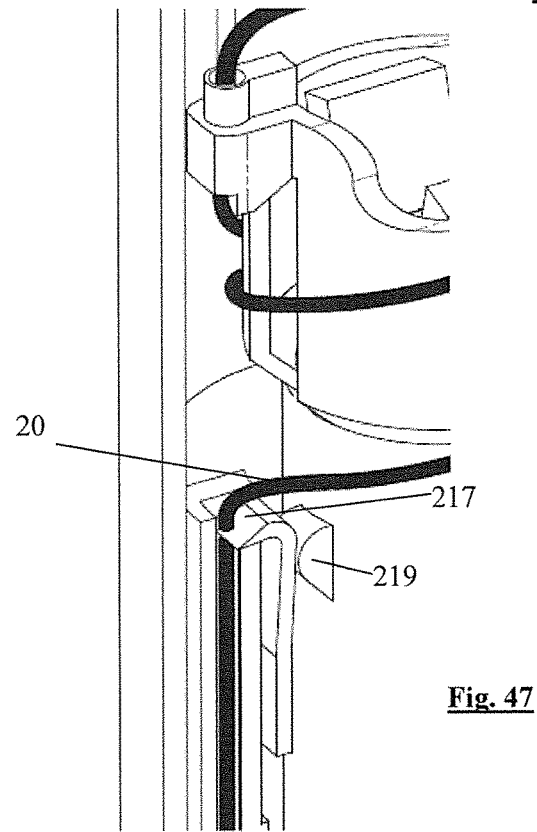

Referring to FIGS. 30 to 35 and also to FIGS. 45 to 47, the suture is cut to a desired length by a cutting blade 217 located at the exit from the suture feed channel 211. The blade 217 is normally retracted as illustrated and is activated to cut the suture when a projecting part 218 of the blade 217 is engaged by a projection 219 on the twist mechanism 60 as it is pushed forward.

Figure 36:
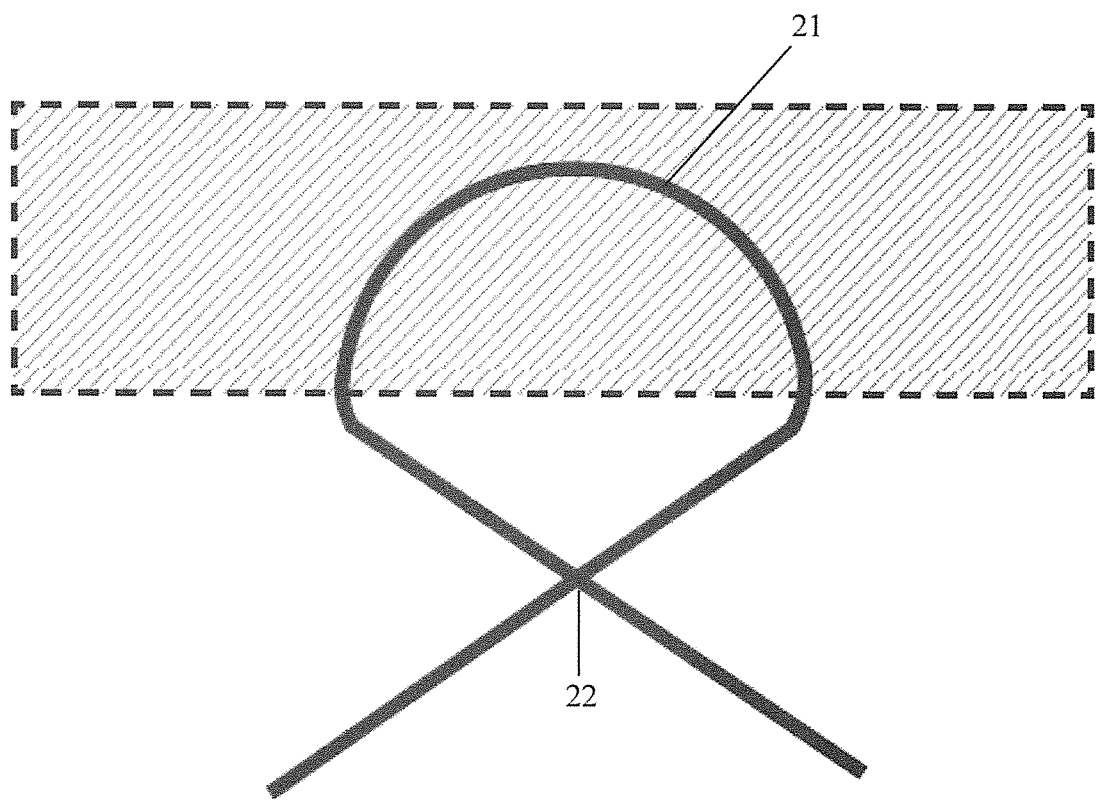
FIGS. 36 to 38 illustrate the formation of a suture loop using the suture device.
Figure 37:
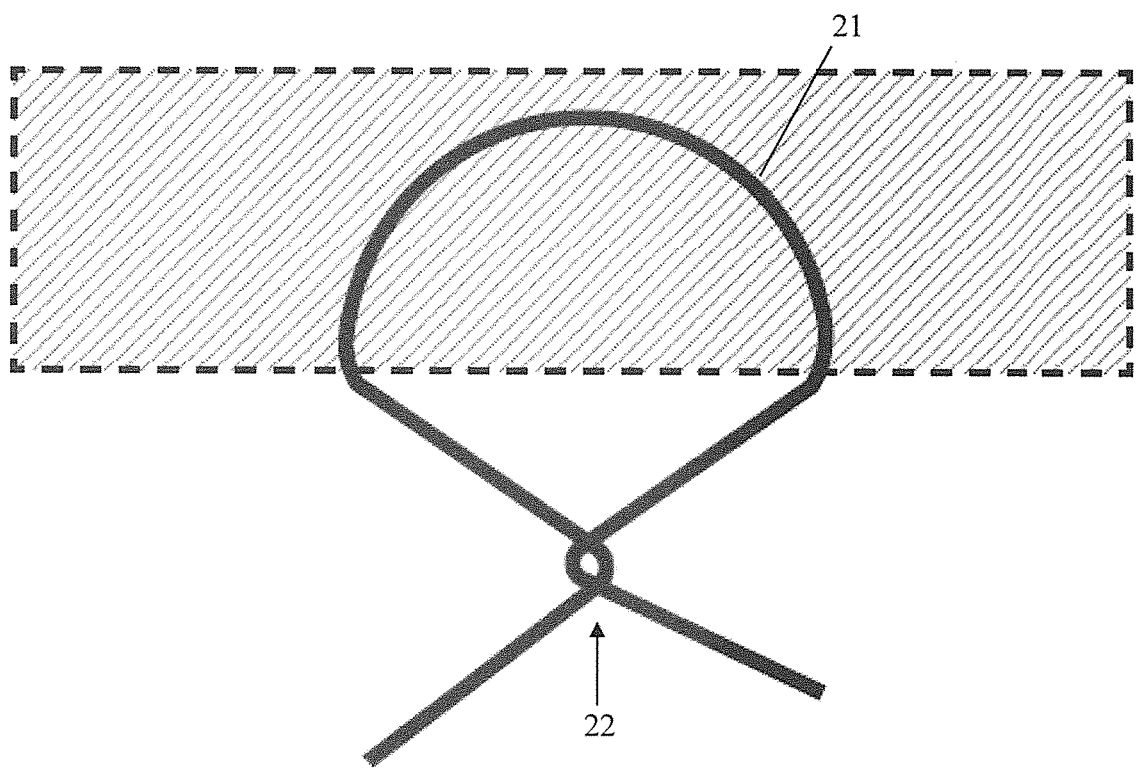
Figure 38:
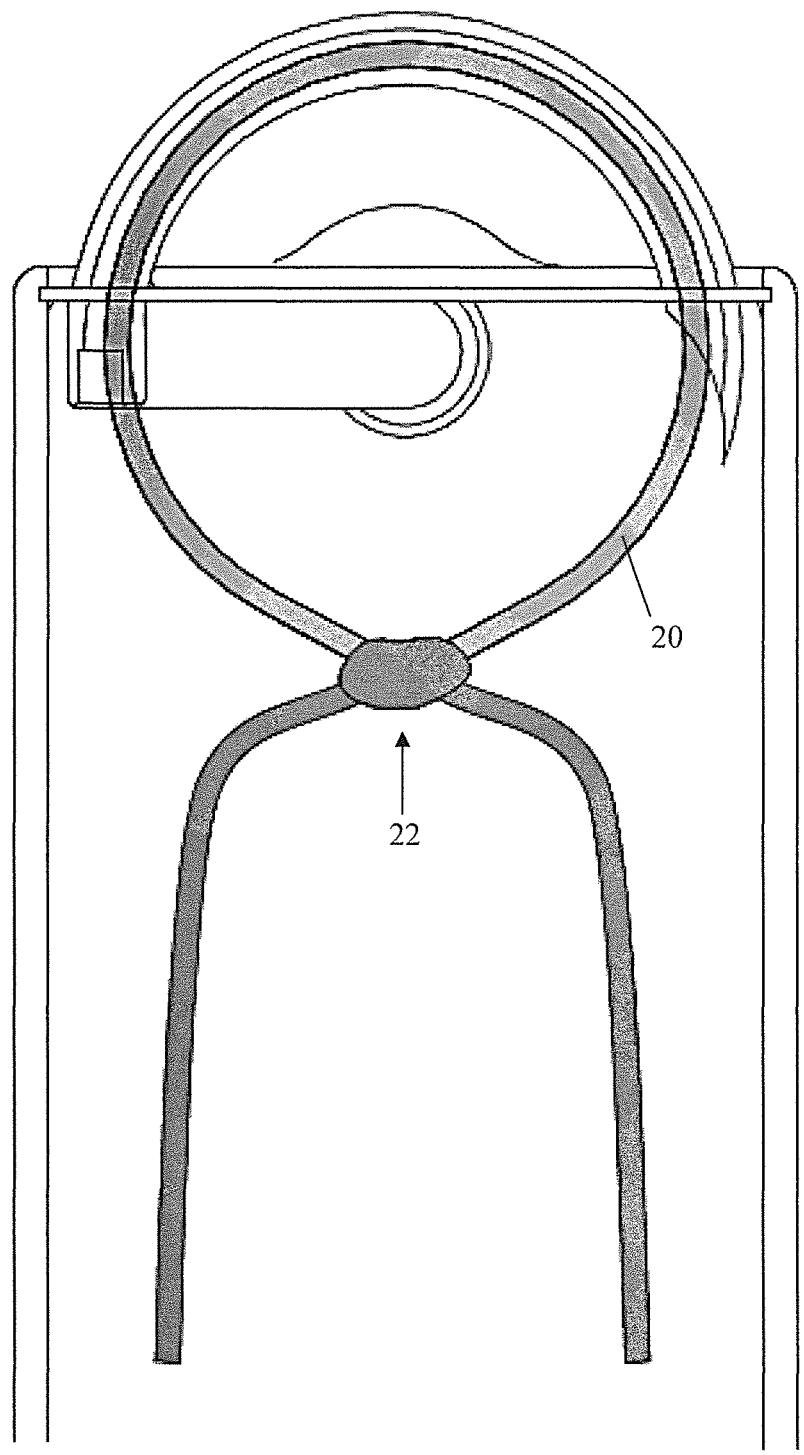

FIGS. 36 and 37 illustrate that the suture can be twisted 180 degrees (one cross over) up to more than 360 degrees. The suture loop can be fixed with a circumference of, for example, 10 mm with part of such as half the loop contained in the tissue. The external part of the loop can be shortened by adding additional twists therefore creating a suture loop with tension as illustrated in FIGS. 105 to 109. The primary objective is a tension free suture loop.

Figure 39:
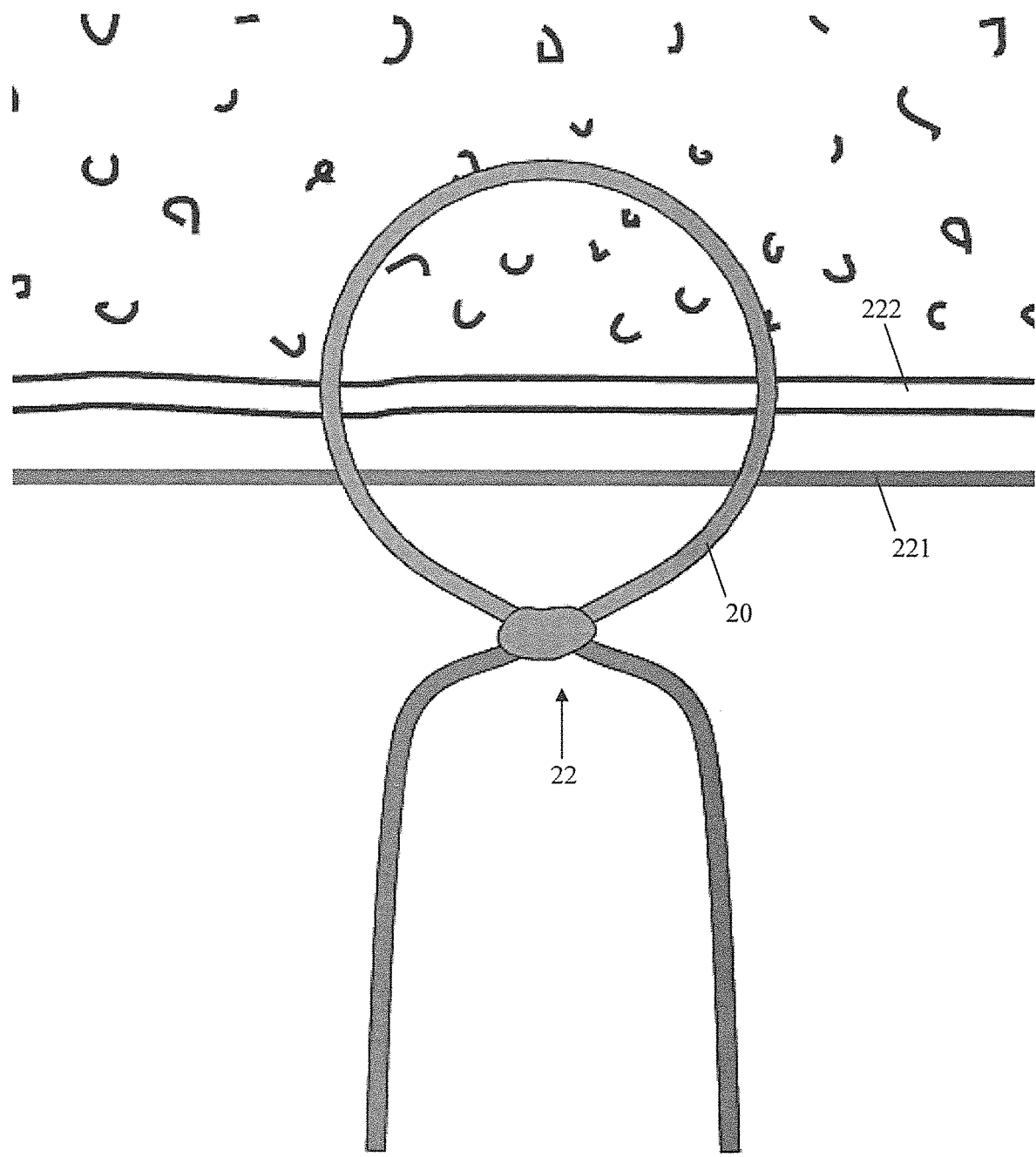
FIG. 39 illustrates a suture loop in use attaching a mesh to tissue.

Referring to FIG. 39 a suture 20 is illustrated extending through a mesh 221 (such as a hernia mesh) and into tissue 222. It will be noted that only about 50% of the loop is embedded in tissue and the balance remains external to the tissue. The mesh 221 is thereby free to adjust adjacent tissue and thereby improve patient comfort. At the same time the suture loop 20 ensures that the mesh 221 is securely held to the tissue.

FIGS. 40 to 42 illustrate a suture cartridge 35 that can be sterilised separately.

Figure 43:
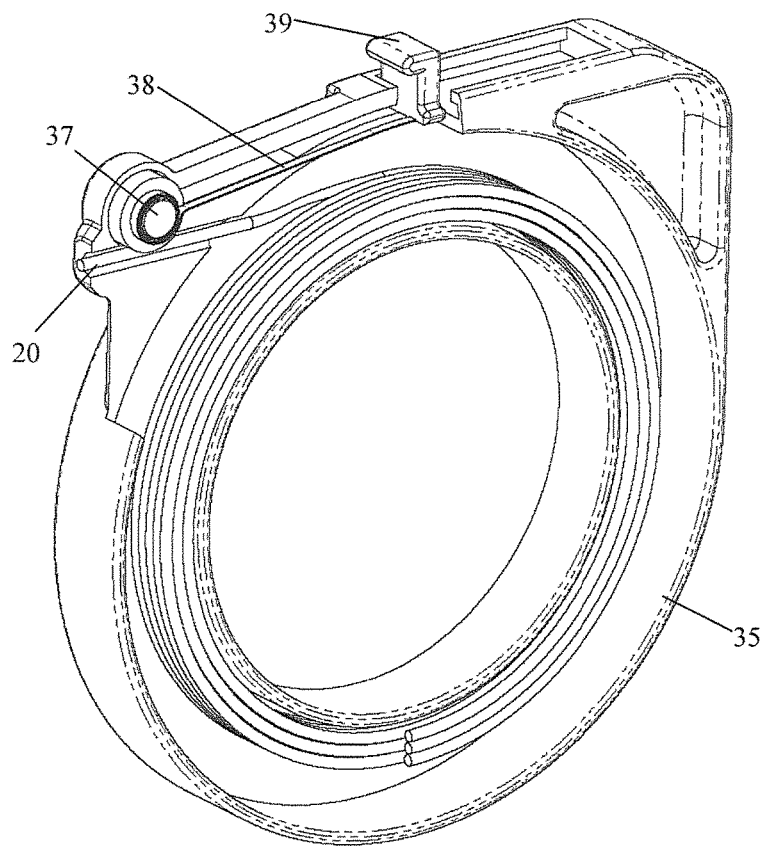
Figure 44:
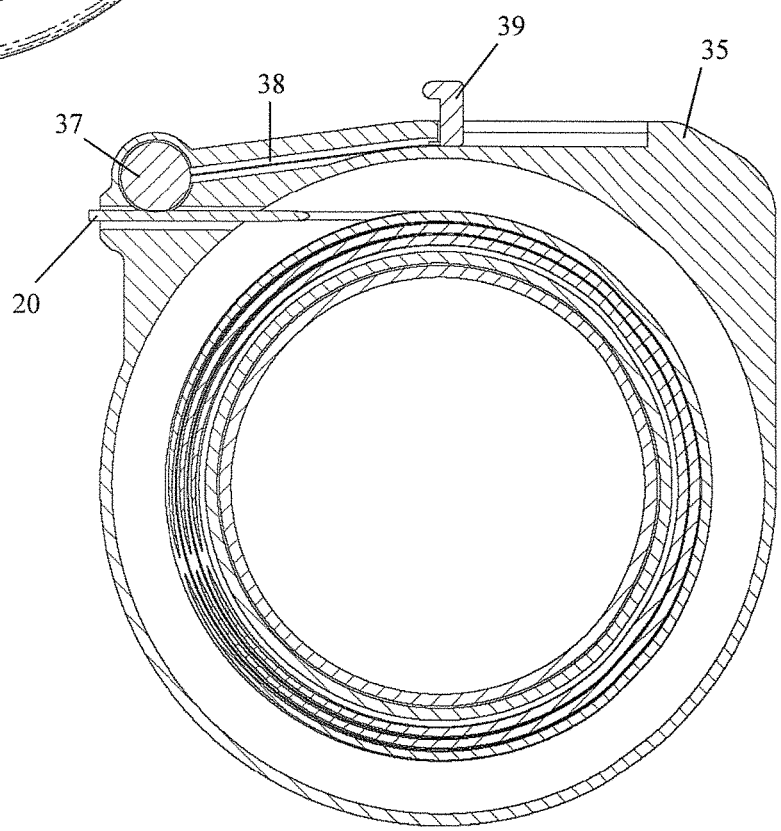

Referring to FIGS. 43 and 44 the cartridge 35 has a mechanism in the top that automatically starts to feed the suture 20 out of the cartridge 35 as the cartridge drawer 30 is slotted into the back of the device. A wheel 37 feeds the suture 20 as a cable 38 wrapped around its axis is pulled out by the hook or trigger 39 catching on a feature inside the device.

FIGS. 45 to 47 illustrate that the suture cut happens at the point where the suture 20 comes out of the feeding channel. The cut is made by a toughened blade 217 (which may be of steel) that is deflected by the twist mechanism 60 when it is pushed forward. The blade 217 engages with a flat surface or another blade on the opposite side of the suture feed channel.

Figure 48:
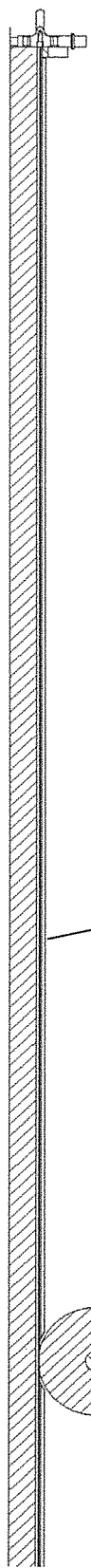
FIGS. 48 and 49 are views of a suture driving system.
Figure 49:
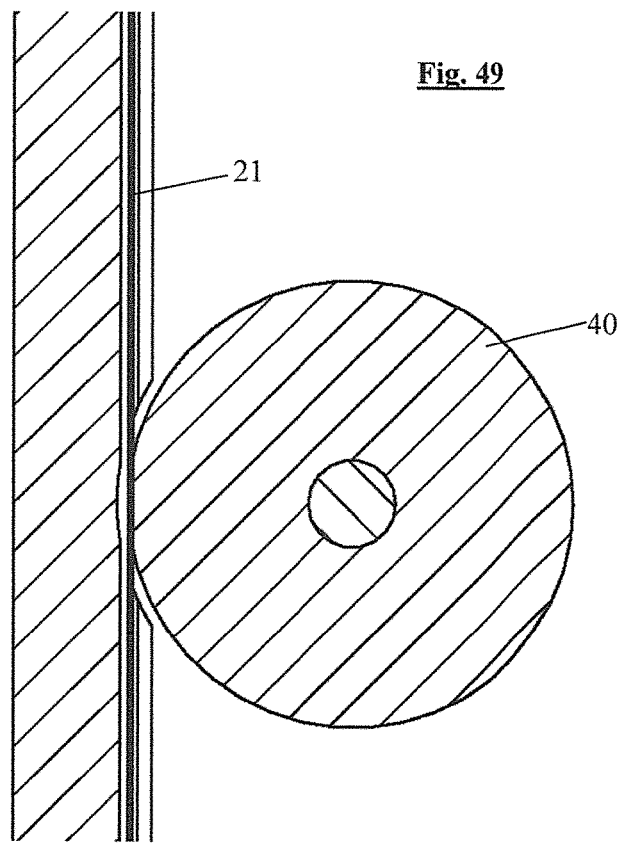

FIGS. 48 and 49 show the suture 20 pushed from the handle 3 of the device up the shaft by a wheel 40 that captures the suture 20. This wheel 40 is driven by a motor in the handle 3. The wheel 40 may be coated with or comprise a flexible material such as rubber or plastics.

In the invention individual suture loops are formed to secure a mesh to adjacent tissue. The loops will generally all be of a pre-set size set by the suture device. The suture loops ensure that the mesh is efficiently and effectively placed and retained in place but with sufficient flexibility to allow some movement of the mesh to accommodate patient movement, for example as a result of coughing. Unlike anchors or screws the loops will not result in localised pain to the patient when such movement occurs. The loops are generally slack and not tensioned against tissue. The mesh may be applied in any desired manner, for example, by first applying loops at some locations such as the corners to locally retain the mesh and then apply further suture loops around the periphery of the mesh.

As described above, the loop may extend through just one or two holes in the mesh. The holes may be pre-formed in the mesh or may be made when the curved needle is advanced through the mesh before the suture is threaded through the needle.

Referring to FIGS. 50 to 72 there is illustrated another suture device according to the invention. In this case the suture is bonded without a requirement for a twisting mechanism. Consequently, the mechanism is simpler to operate and cheaper to manufacture.

Figure 50:
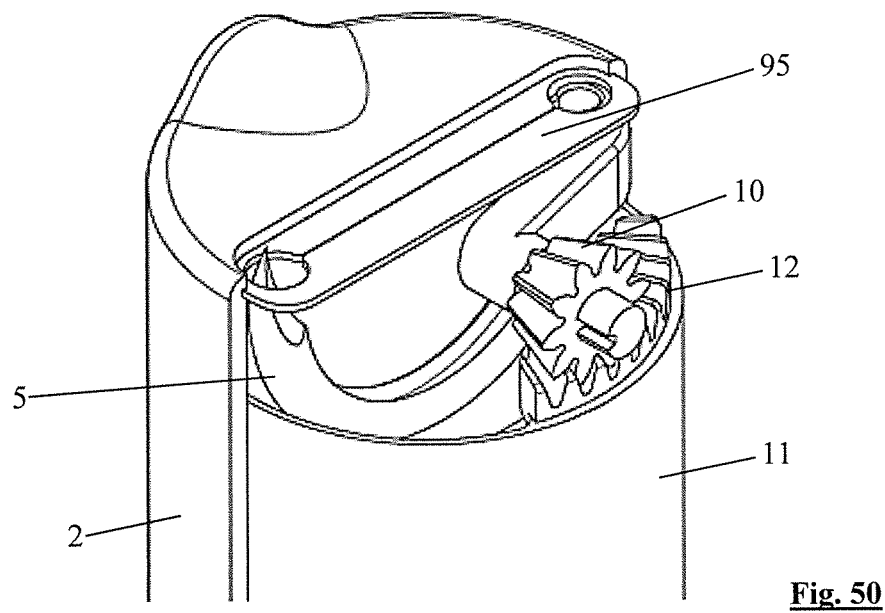

FIG. 50 illustrates a needle 5 that is rotatable at the distal end of the device. The distal opening is covered in with a silicone flap 95 to prevent the ingress of fluids or debris.

Figure 51:
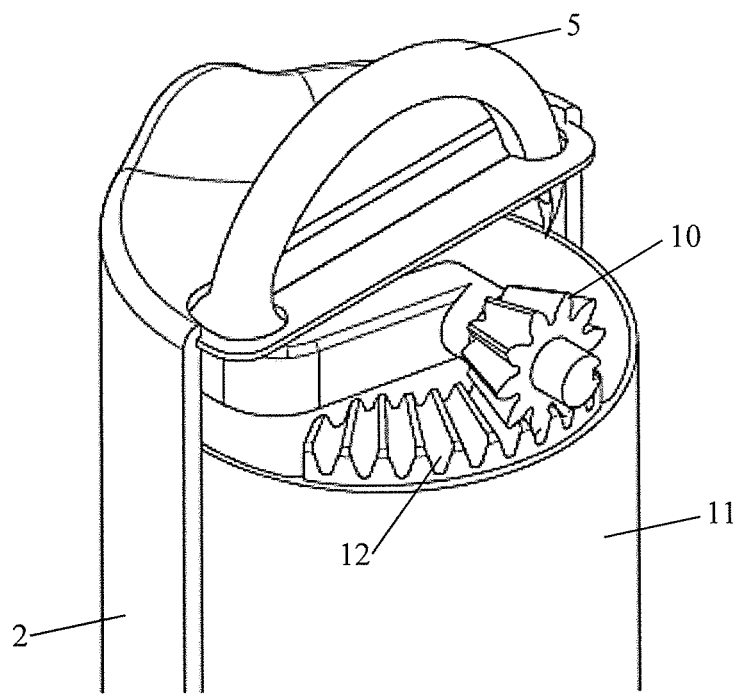

The needle 5 has a cog 10 which is driven by a gear 12 on the internal shaft 11 that turns to drive the needle 5 as illustrated in FIG. 51.

Figure 52:
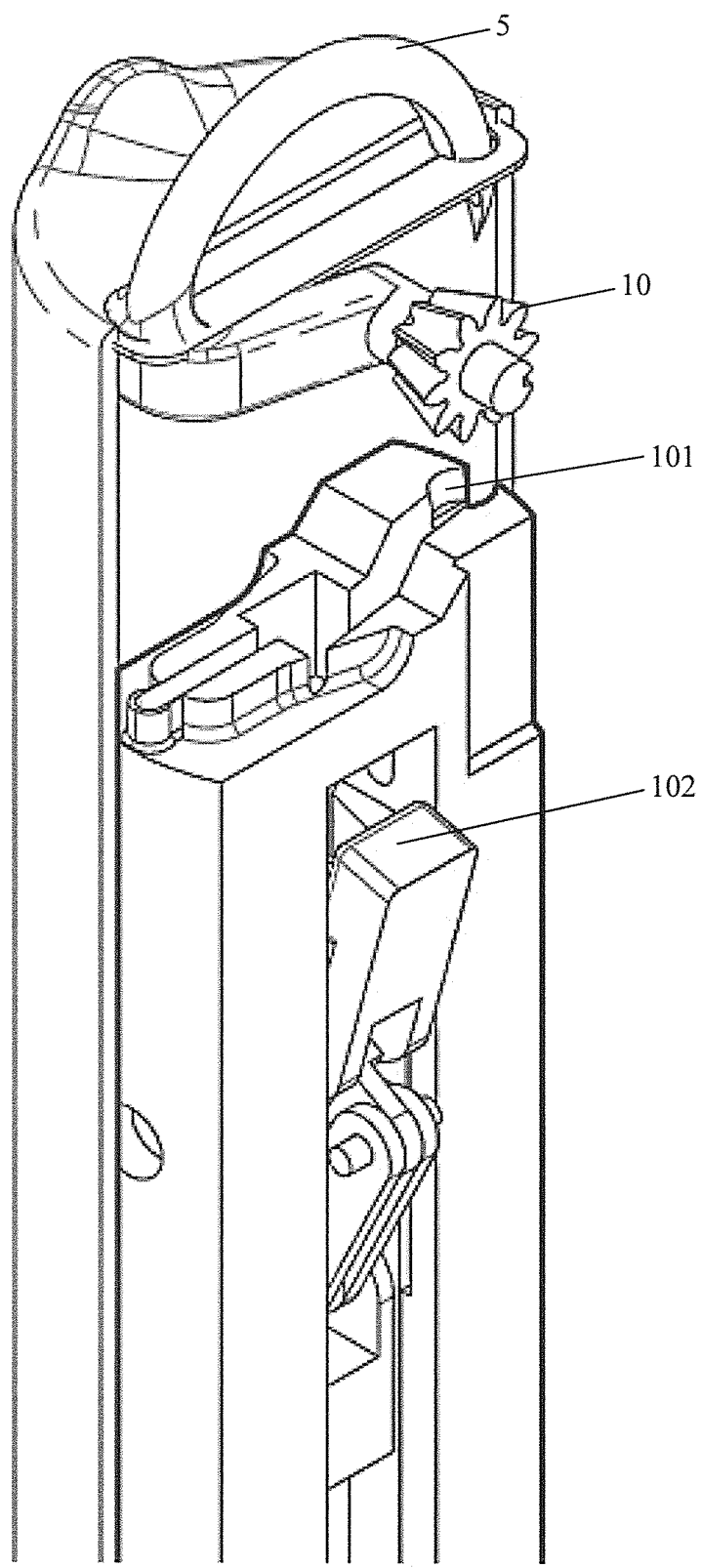

FIG. 52 illustrates the internal assembly which comprises a suture path 101, a suture push mechanism (such as described above with reference to FIGS. 48 and 49), a suture bonding mechanism 102 and a suture cutter 104.

Figure 53:
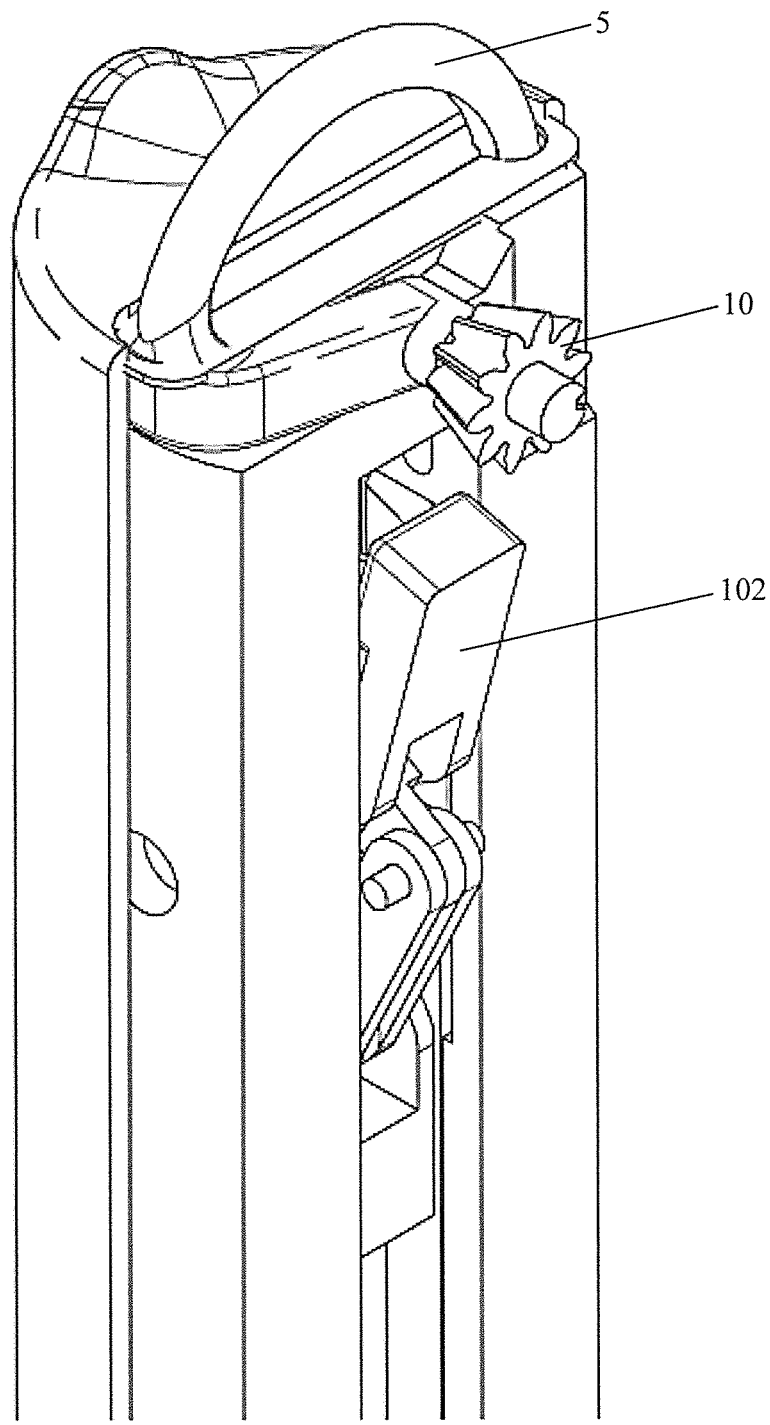
Figure 54:
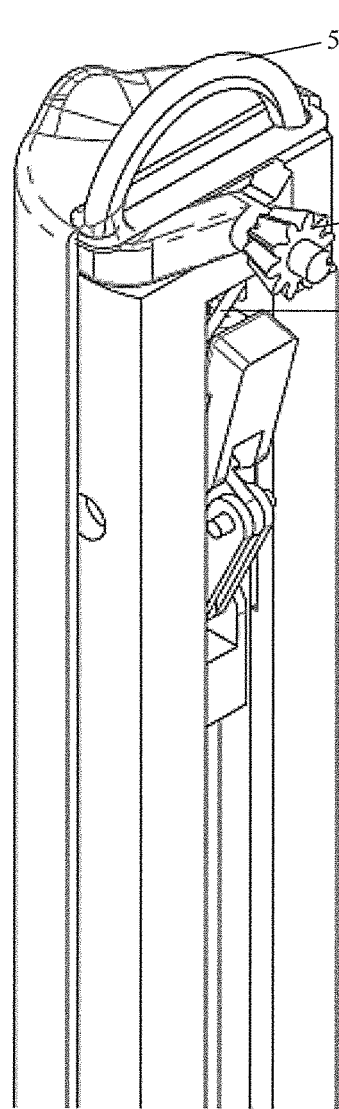
Figure 55:
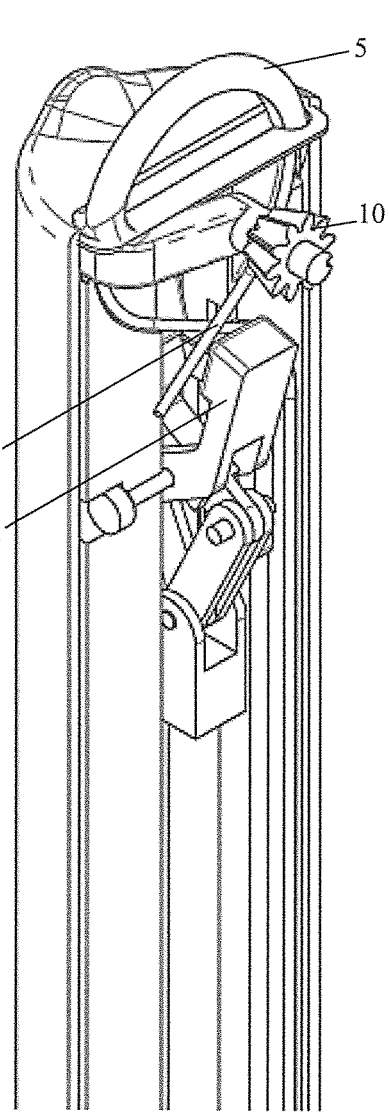
Figure 56:
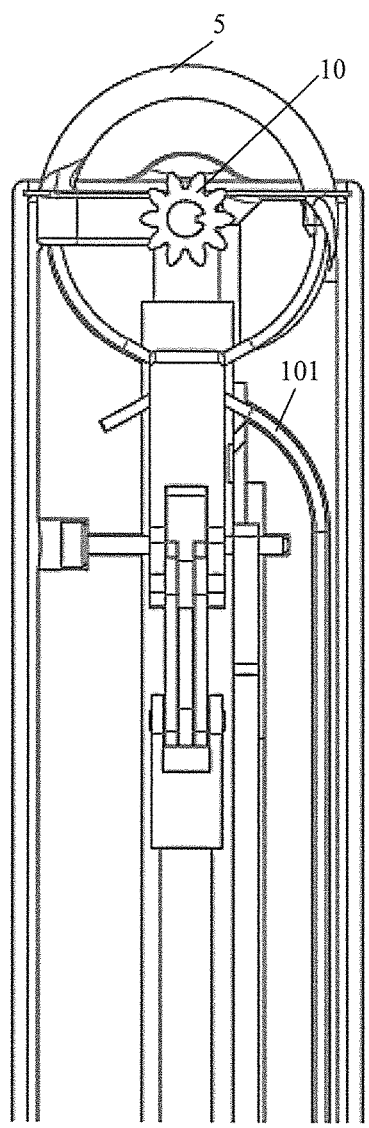

FIG. 53 illustrates the internal assembly advancing to the needle 5.

Once the assembly is in place, a suture 100 is pushed up through the channel 101, around the needle 5 until it crosses over the original suture. The return section of the suture channel is rotated by, for example, 9 degrees to allow for the leading end of the suture to cross the suture without clashing.

As illustrated in FIGS. 57 to 58, the heated clamp 102 closes over at the suture cross over point 105. Time, temperature and distance between the hotplates will typically be about 1.5 seconds at 150° ° C. with a 0.5 mm gap.

Referring to FIGS. 59 to 62 the mechanism for opening and closing a heat clamp with jaws 230, 231 is illustrated in more detail. The jaws 230, 231 are pivotal about a pivot pin 232 and link arms 233, 234 are connected at pivot points 235, 236 to the jaws 230, 231. The link arms 233, 234 are connected to a rod 237 through a pivot pin 238. The rod 237 is pulled back to close the clamp. The pivot pin 232 that the clamp activates around is connected to the suture channel in the core device assembly.

Figures 63, 64:
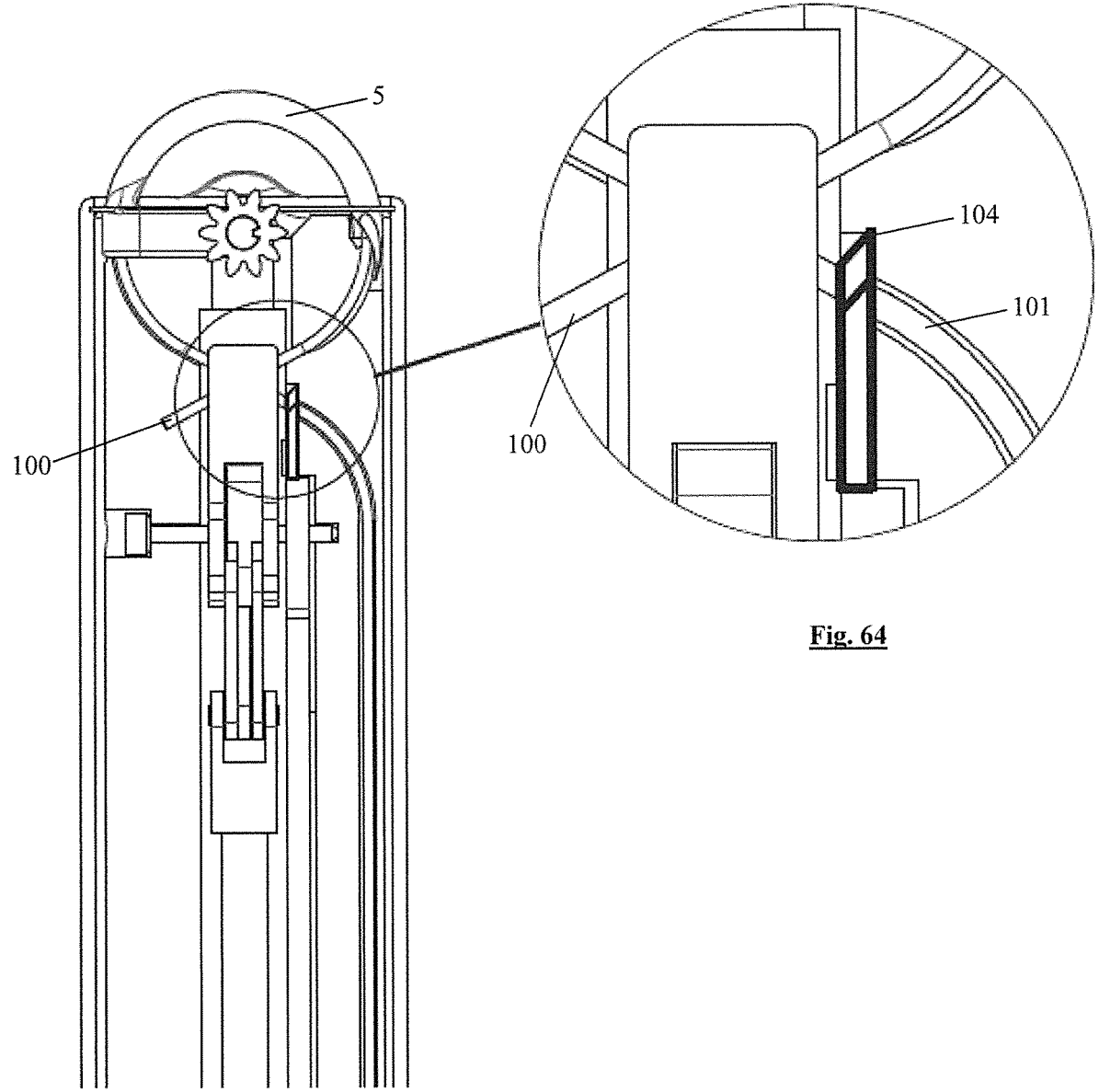

FIGS. 63 and 64 illustrate that as the suture 100 is melted and bonded, the cutting blade 104 advances to cut the suture 100 as it emerges from the suture channel 101.

Figure 65:
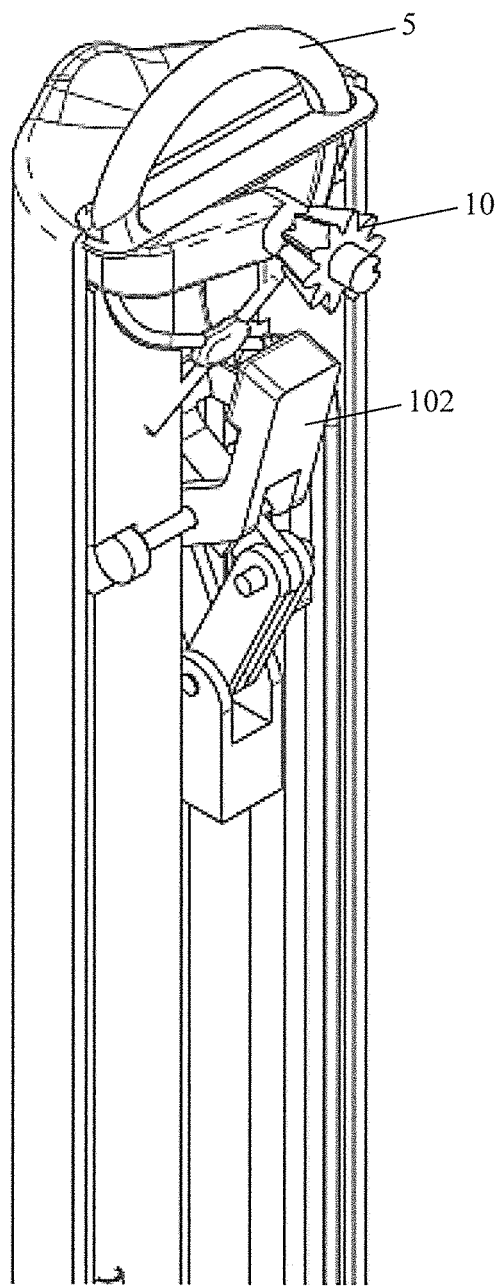
Figure 66:
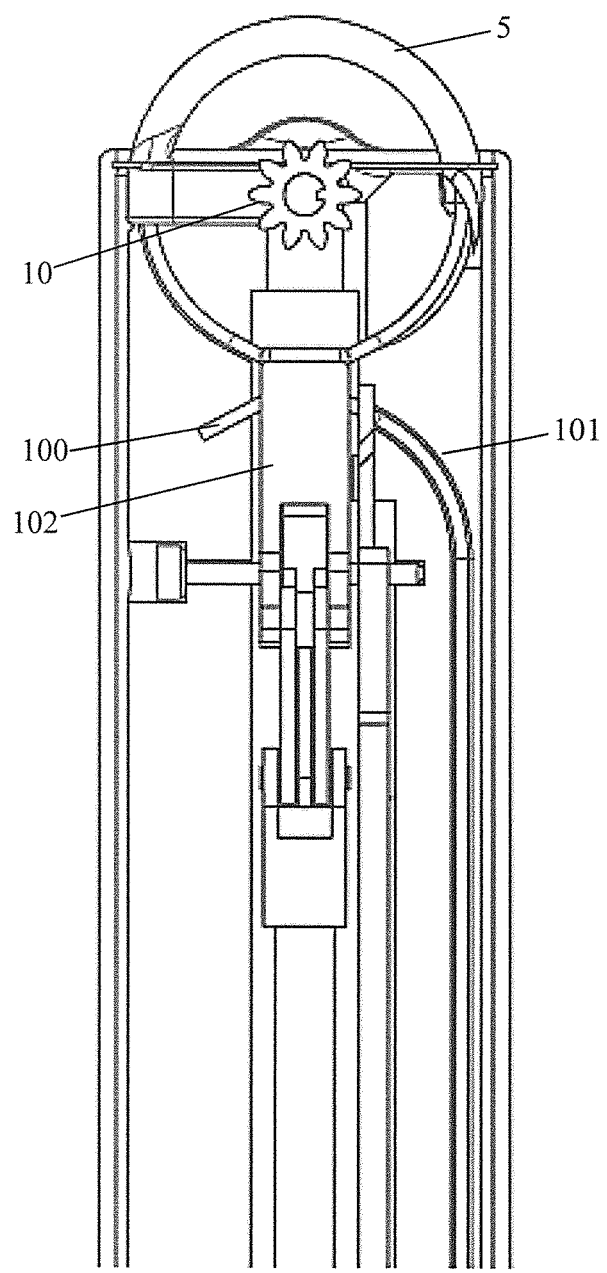

FIGS. 65 and 66 illustrate the heat clamp 102 opening and the cutting blade 104 retracting as the whole internal assembly retracts away from the needle.

Figure 67:
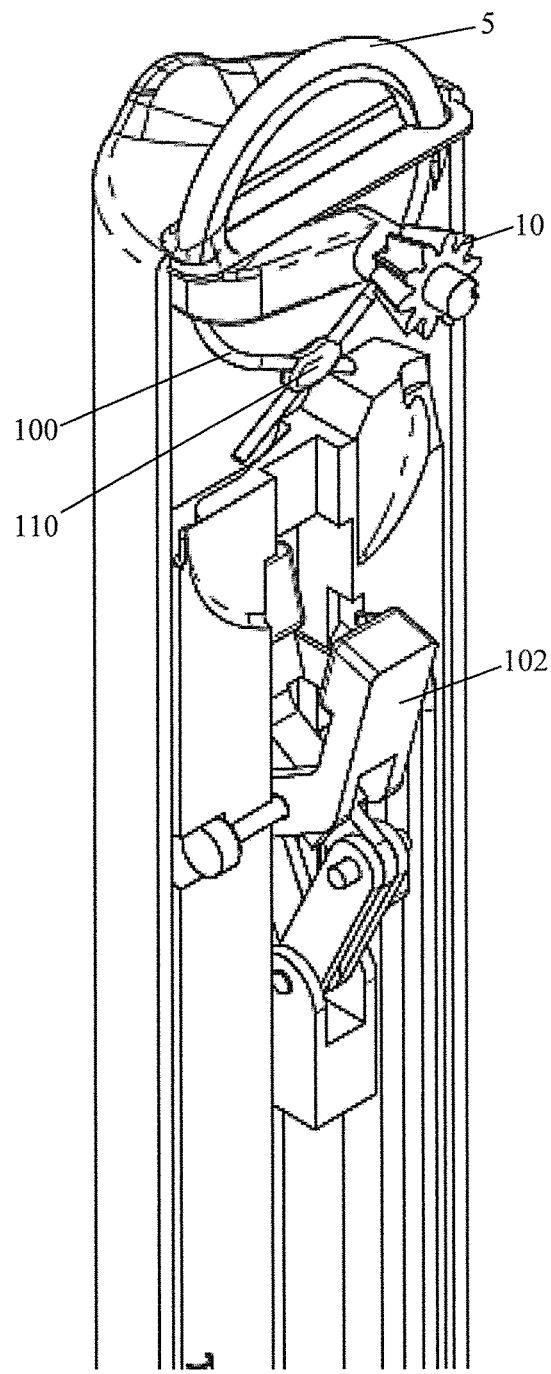
Figure 68:
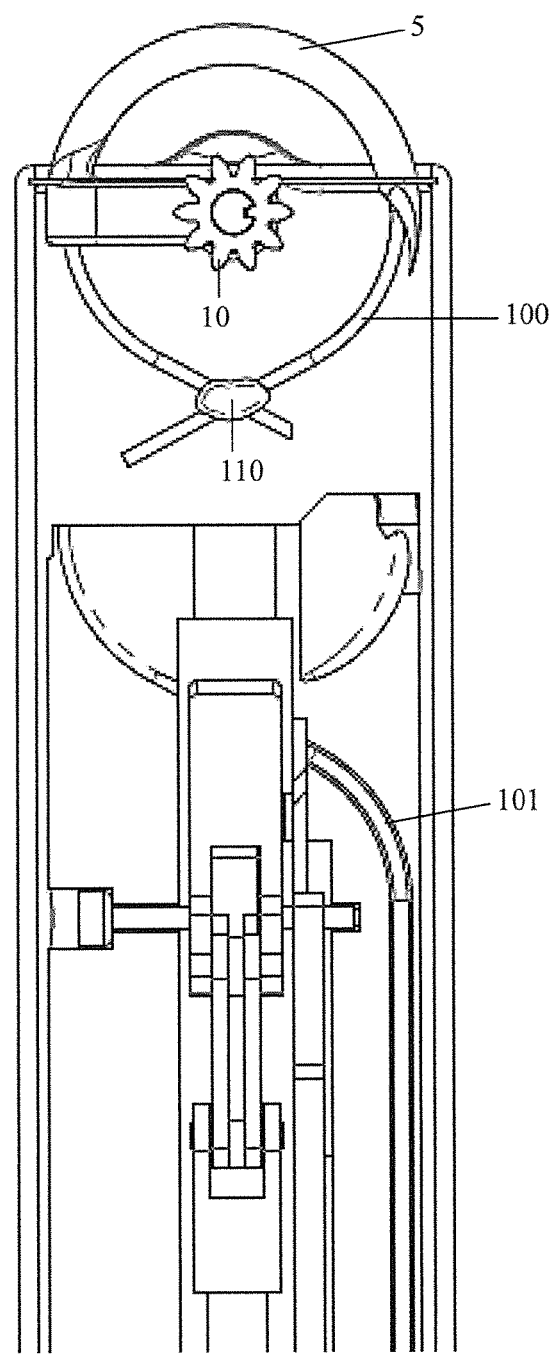

FIGS. 67 and 68 illustrate a suture loop 100 left in place in the tissue and needle 5 while the internal assembly retracts.

Figure 69:
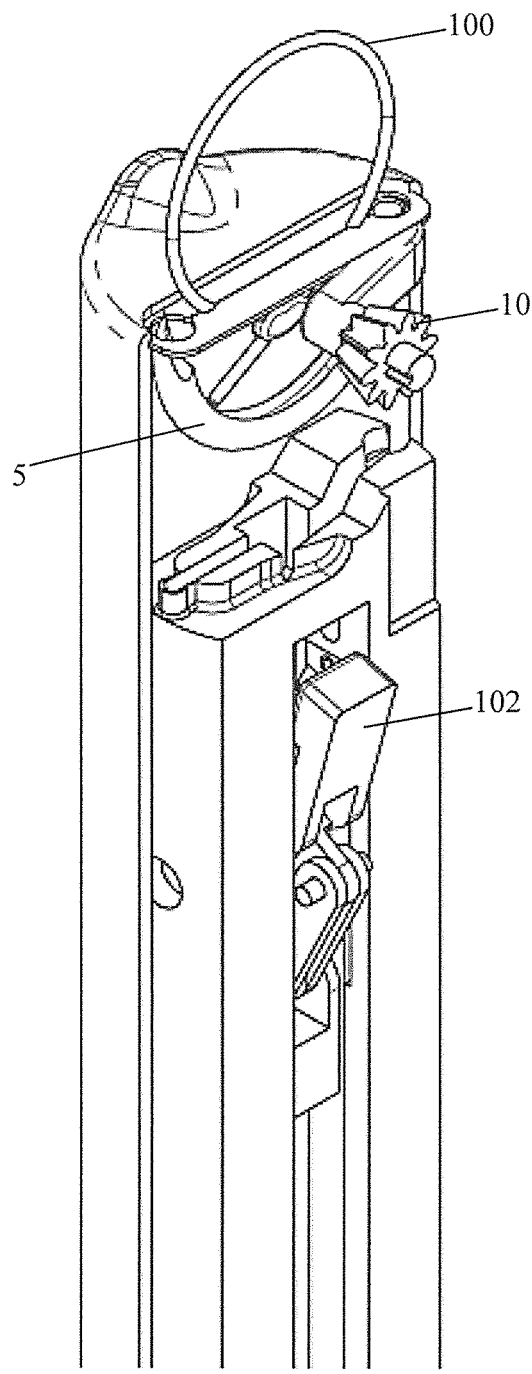
Figure 70:
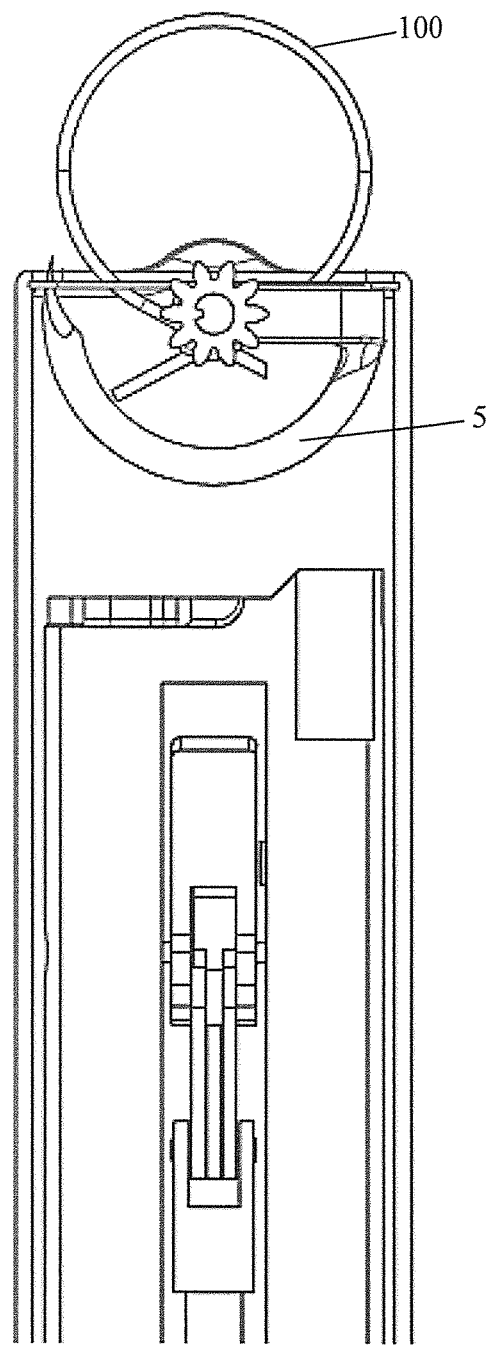

FIGS. 69 and 70 illustrate retraction of the needle 5. Once the needle 5 is retracted, the device is pulled back leaving the loop in the tissue.

Figure 71:
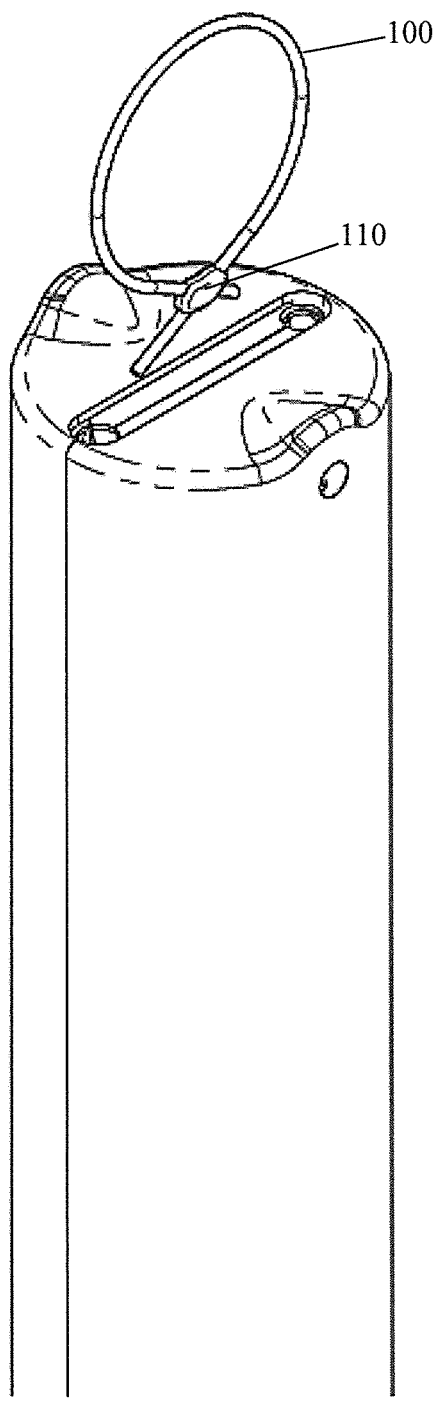
Figure 72:
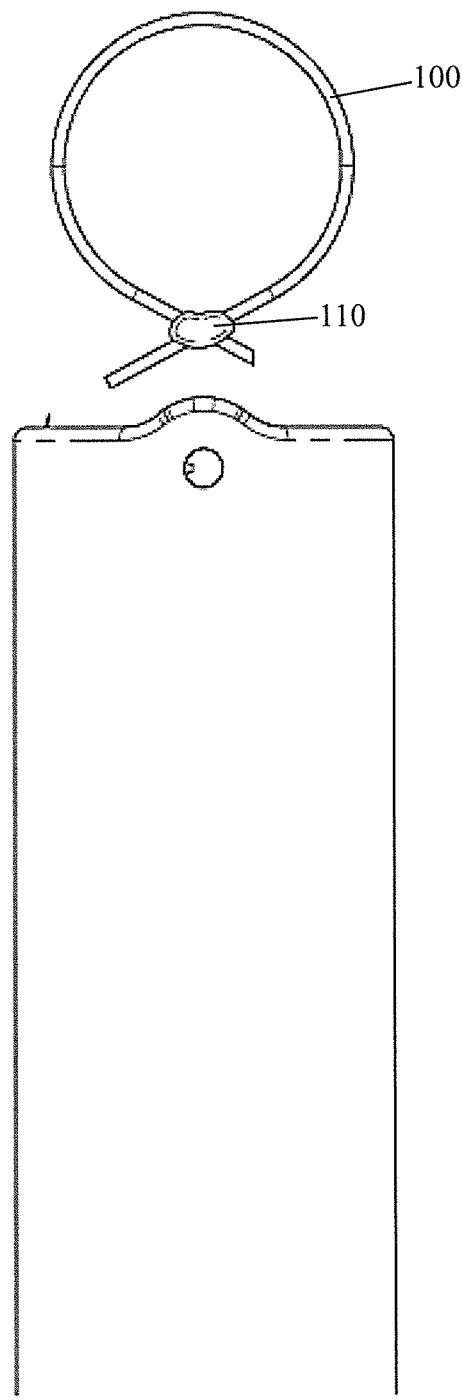

FIGS. 71 and 72 show the suture loop 100 with the bond 110 released through the silicon flap 95. This design removes the need for a twisting mechanism.

Figure 73:
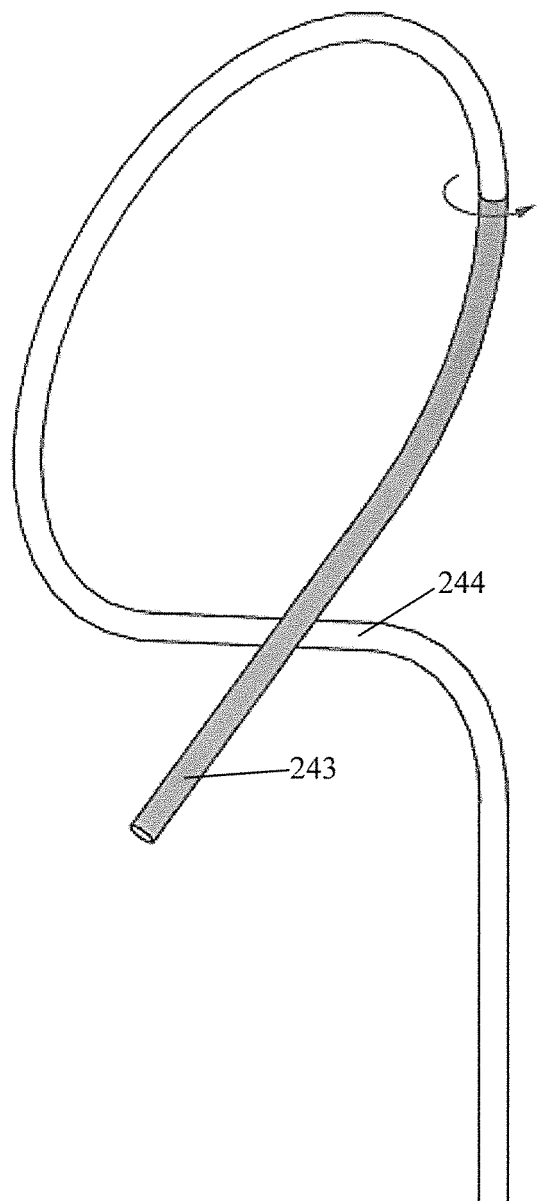

Referring to FIGS. 73 and 74 the offset of the suture to facilitate overlap is illustrated in more detail. A first section 240 of suture is in one plane 241 which is in alignment with the needle. When the suture exits the needle the receiving channel for the suture is in another plane 242 which is offset from plane 241, in this case rotated by typically 9 degrees to enable the leading section 243 of the suture to bypass the following strand 244 of suture.

Figure 75:
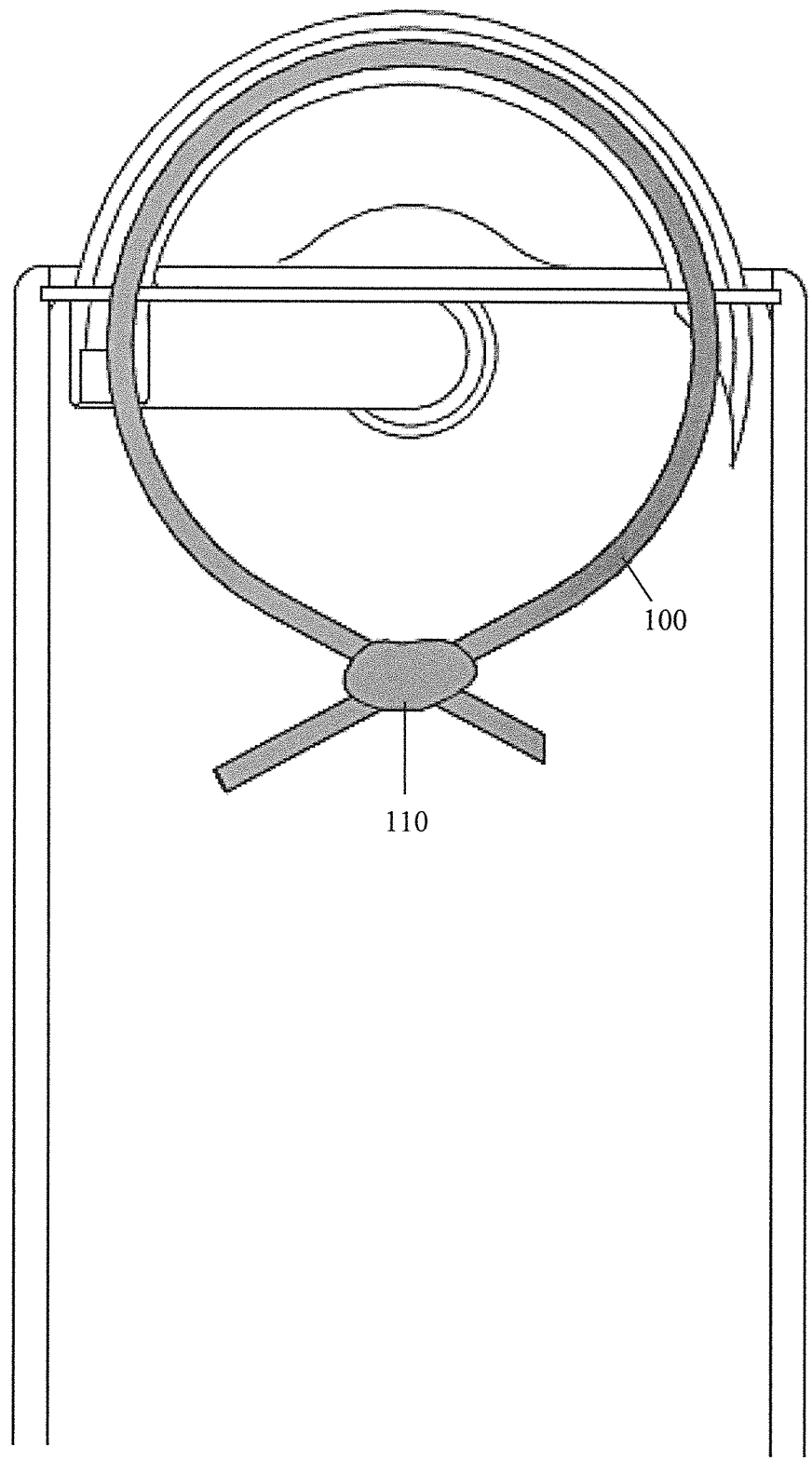
FIG. 75 illustrates the formation of a suture loop.
Figure 76:
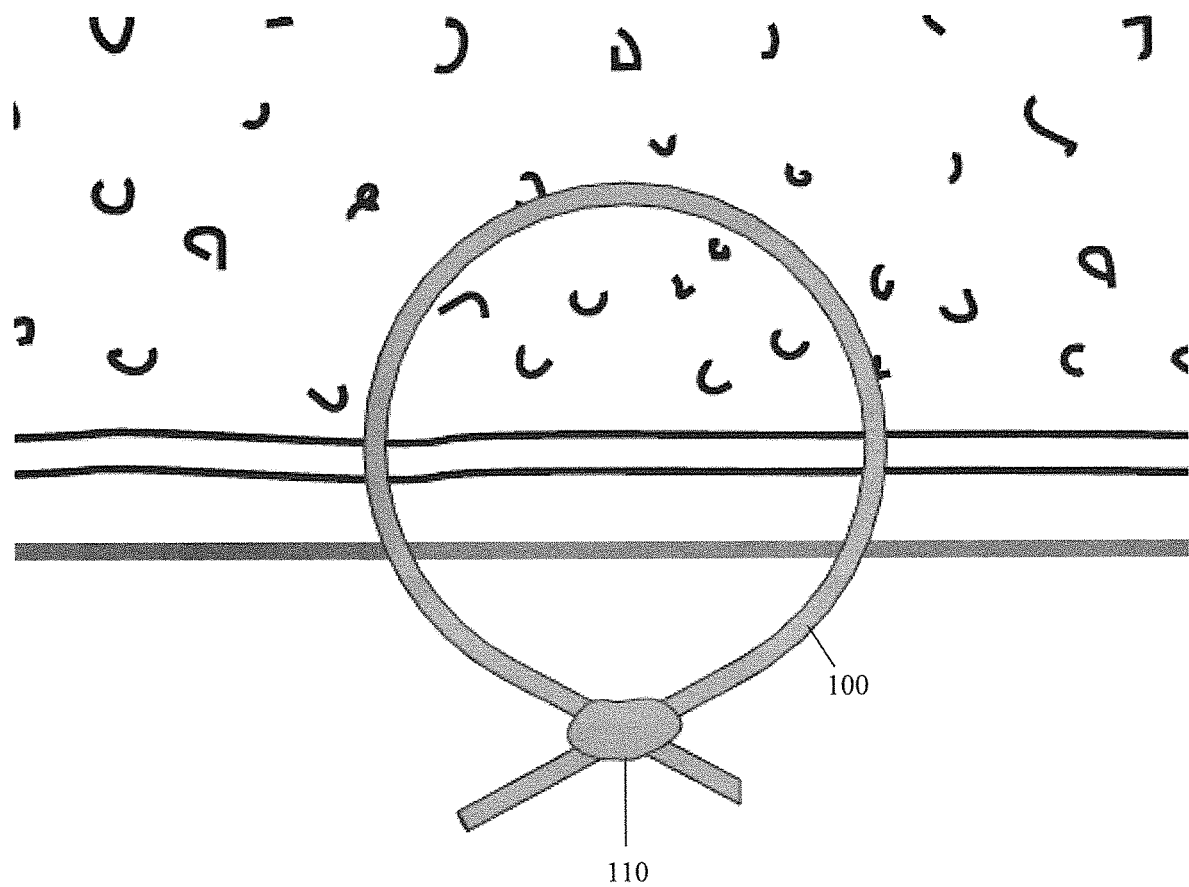
FIG. 76 illustrates the suture loop of FIG. 75 in use attaching to tissue.

FIGS. 75 and 76 illustrate the suture loop formed using the device of FIGS. 50 to 74. It will be noted that the tail section of the suture loop extending beyond the joint is significantly shorter than in the case of the tail section of the loop formed using the device of FIGS. 1 to 49. The shorter tail sections result in improved patient comfort.

FIGS. 77 to 85 illustrate various suture bonds.

FIGS. 77 and 78 illustrate a single cross over bond 120.

FIGS. 79 to 80 illustrate a suture bonding configuration which is side by side 121. This is an alternative layout of the suture for bonding. As the leading edge meets the advancing suture, instead of crossing by it, it runs along the inside face of the suture loop leaving the suture lying side by side rather than crossed over. The suture is then bonded in this configuration.

Figure 81:
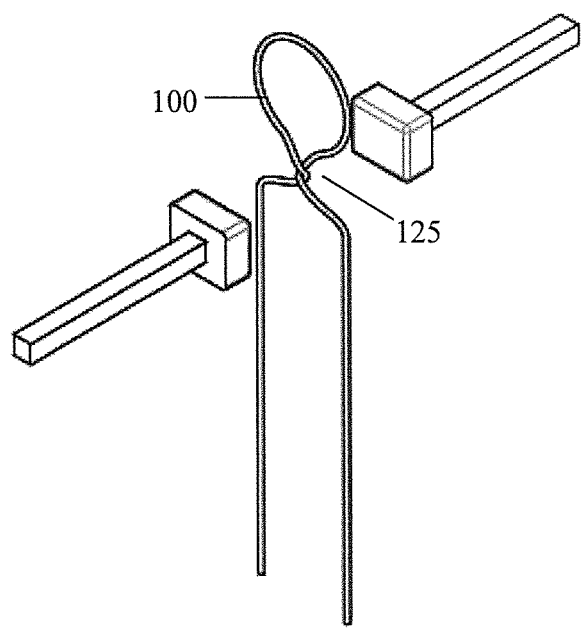
Figure 82:
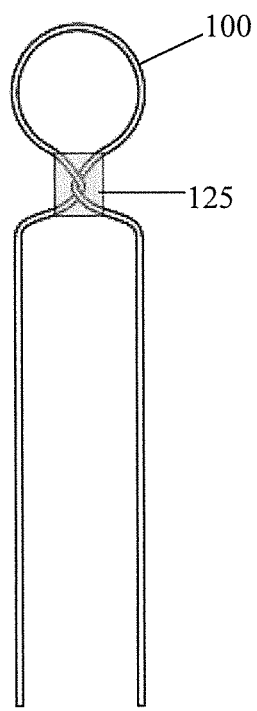

FIGS. 81 and 82 illustrate a suture bonding configuration which is a double cross over 125. This is a configuration created with a twisting mechanism described above.

Figure 83:
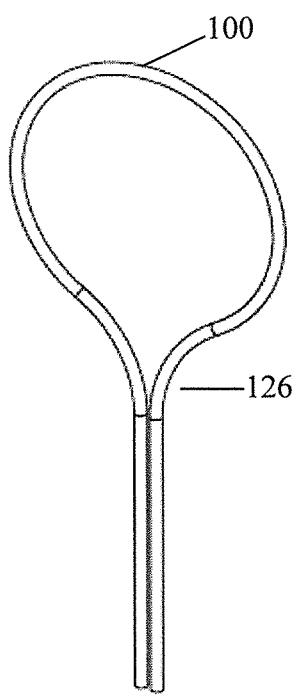
Figure 84:
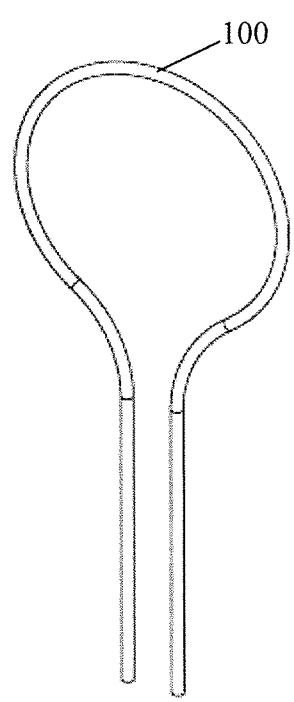
Figure 85:
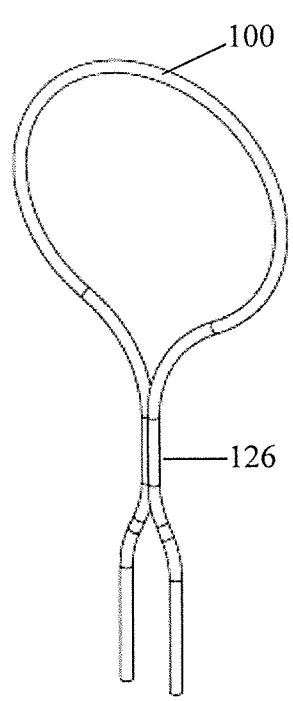

FIGS. 83 to 85 illustrate another suture bonding configuration which in this case is side by side vertical 126. This is another alternative layout of the suture, the suture would be pushed together from the sides to be bonded.

FIGS. 86 and 87 illustrate various pairs of heating plates 129 flat, convex vertical plane, angled with a flattening, concave, convex horizontal plane. The size of the heating plates ranges typically from 4 mm×4 mm to 2 mm×2 mm. The heating plates are shown on a larger scale in FIGS. 88 to 97.

Figure 90:
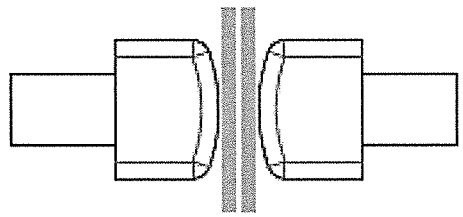
Figure 91:
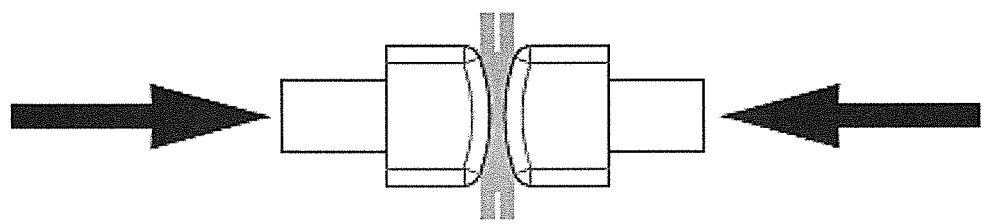
Figure 92:
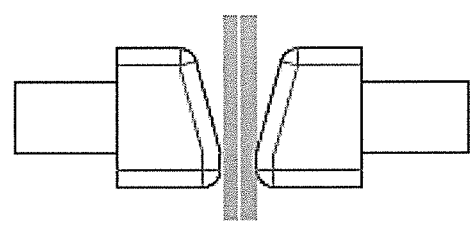
Figure 93:
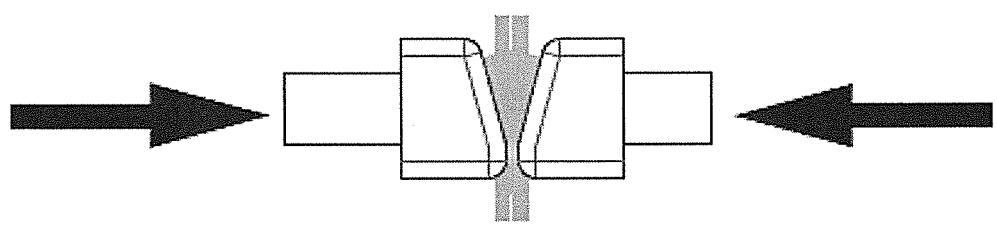
Figure 94:
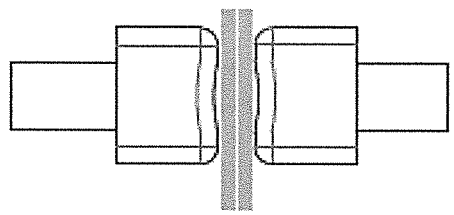
Figure 95:
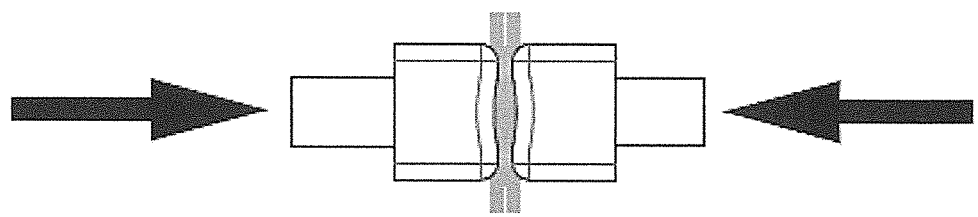
Figure 96:
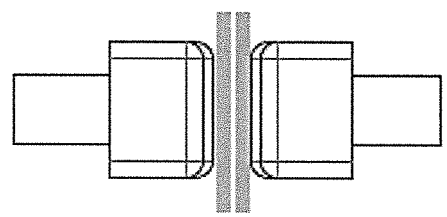
Figure 97:
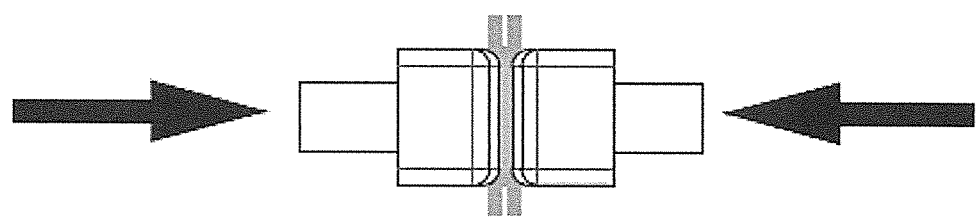

FIGS. 88 and 89 illustrate heating plates which with faces which are generally flat. FIGS. 90 and 91 illustrate heating plates with convex faces. FIGS. 92 and 93 illustrate angled faces to provide additional volume for melding. FIGS. 94, 95 and 96, 97 illustrate heating plates with alternative shaped faces to enhance bonding.

Figure 98:
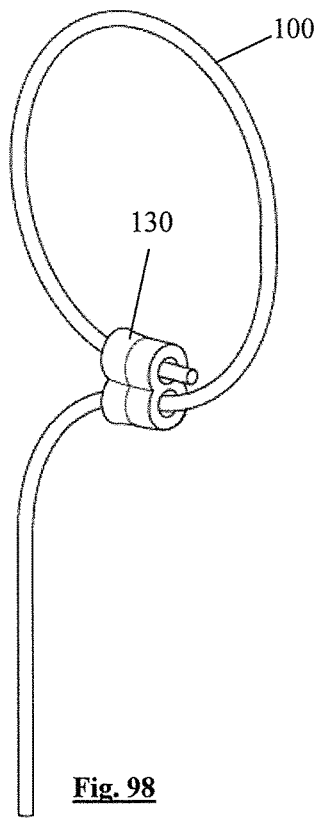
FIGS. 98 and 99 illustrate an alternative type of suture bonding.
Figure 99:
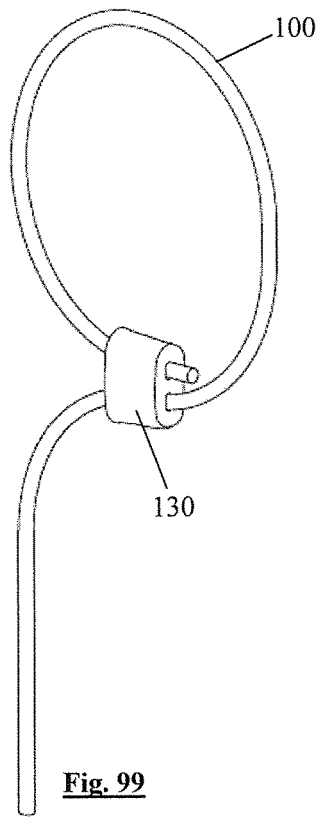

FIGS. 98 and 99 illustrate alternative suture bonding. In this case, at the cross over point, the suture 100 passes through a tube 130 which may be of the same material as the suture. This tube is then melted in the same manner as described above. The tube 130 provides additional material to the bond.

Figure 100:
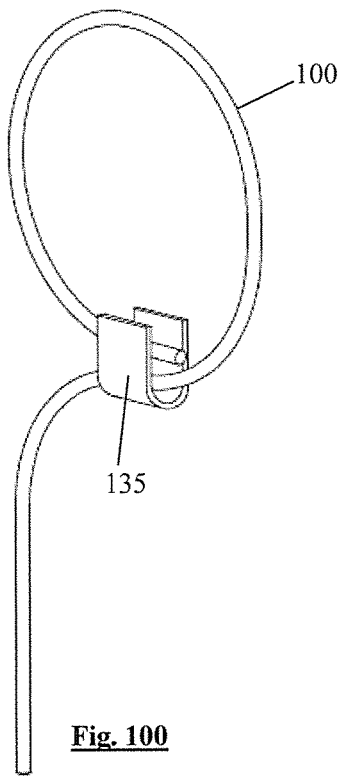
FIGS. 100 and 101 illustrate a crimping clip used to bond a suture.
Figure 101:
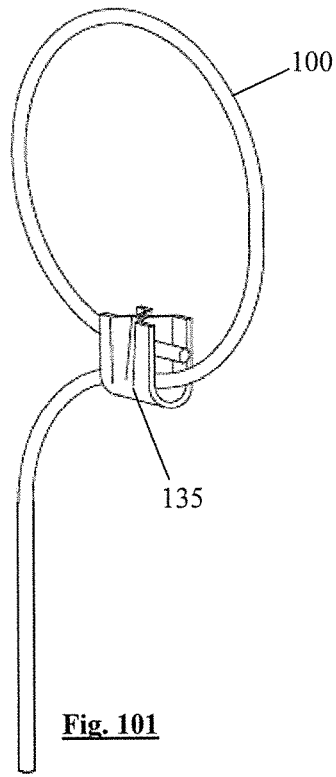

FIGS. 100 and 101 illustrate bonding of the suture 100 using a crimp/clip 135 as an alternative to heat. Force is applied to deform the clip 35 onto the suture creating the loop. Typically the clip 135 is of metal or other suitable material. Adhesive may also be used as an alternative or additionally for bonding.

Figure 102:
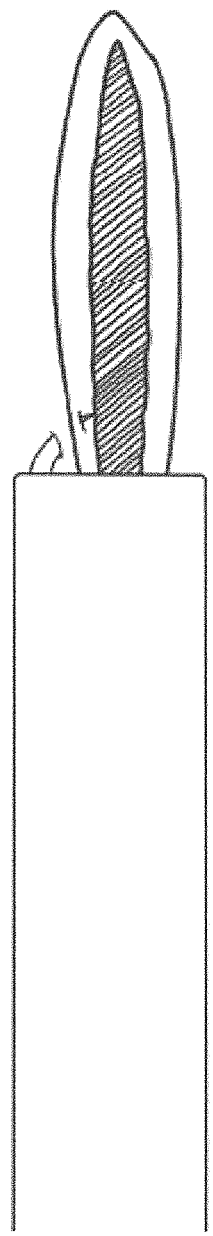
FIGS. 102 to 104 illustrate the device of the invention used for tissue approximation.
Figure 103:
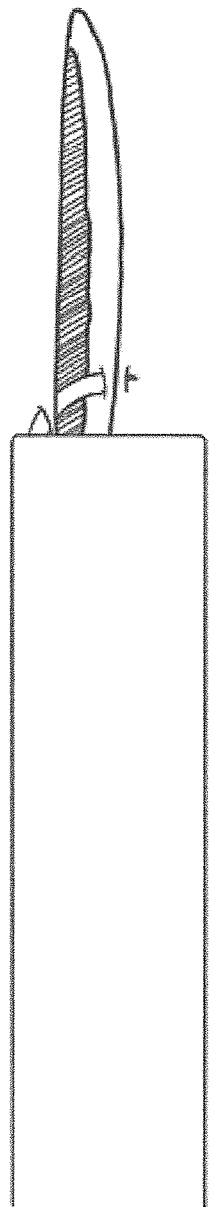
Figure 104:
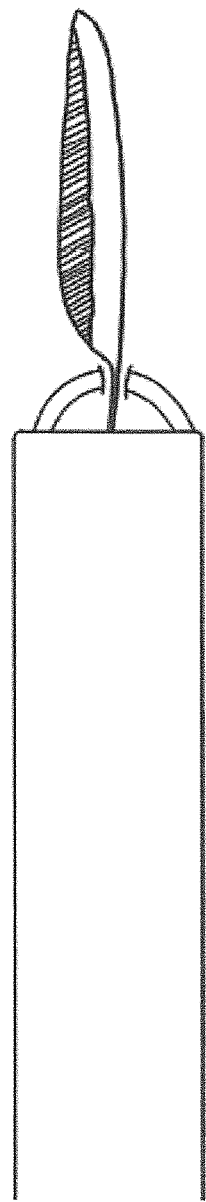
Figure 105:
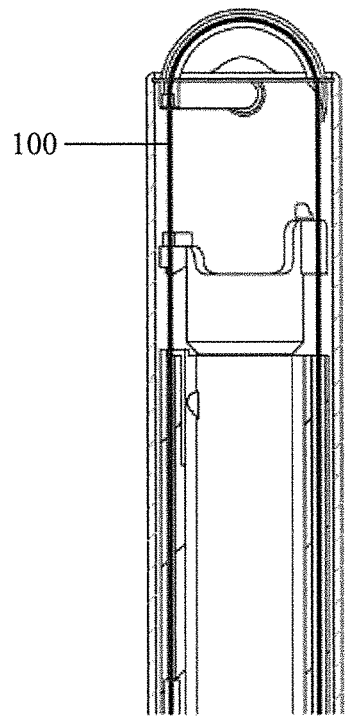
FIGS. 105 to 109 illustrate additional twisting of a suture loop for tightening before bonding.
Figure 106:
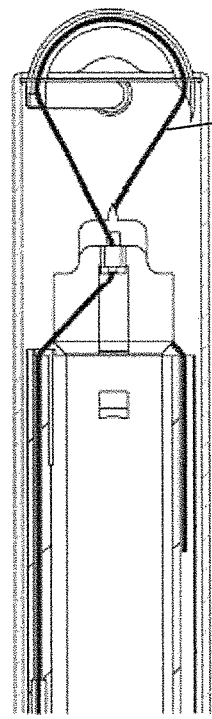
Figure 107:
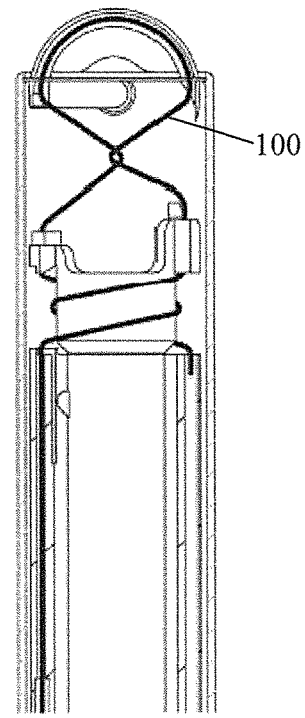
Figure 108:
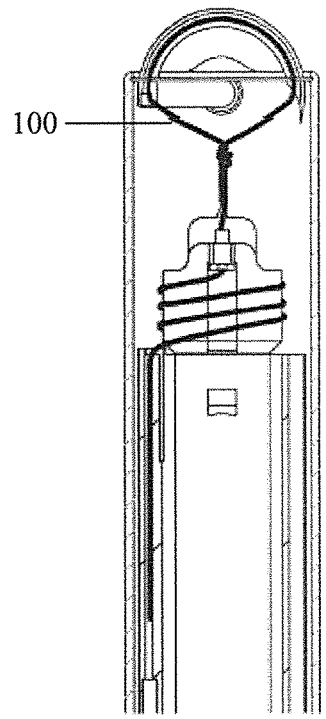
Figure 109:
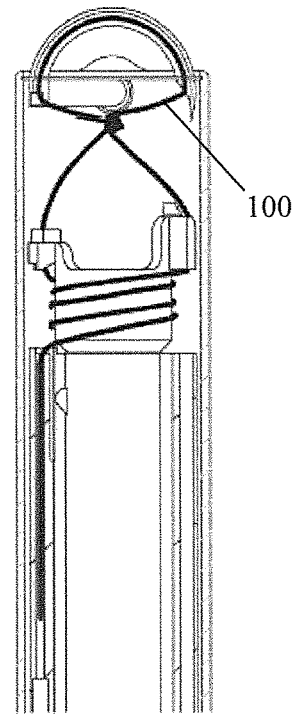

FIGS. 102 to 104 illustrate the suture device in use for tissue approximation. An additional function allows the needle 5 to advance incrementally under the control of the surgeon. The sequence is as follows:
(i) a surgeon deploys needle half way;
(ii) the surgeon uses the needle to puncture/capture the tissue on one side of the defect to be closed;
(iii) the surgeon uses the suture device to move that initial side of the defect to the opposite side;
(iv) once aligned, the surgeon then initiates the second movement of suture device, so that the needle punctures/captures the other side of the defect and the re-set of the device activates. The suture is threaded through the needle, bonded, cut and then the needle retracts.

FIGS. 105 to 109 illustrate that suture loops can create tension by increasing the number of rotations of the twisting mechanism before bonding.

Figure 110:
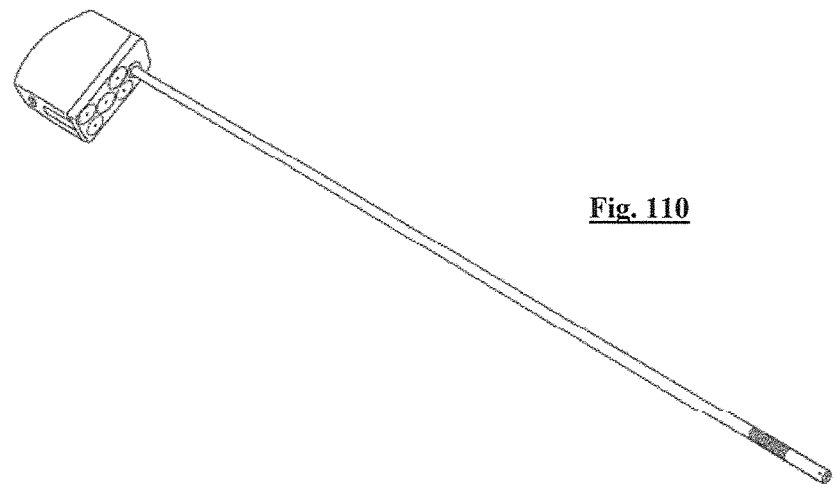
FIGS. 110 and 111 illustrate the device of the invention adapted for use with a robotic system.
Figure 111:
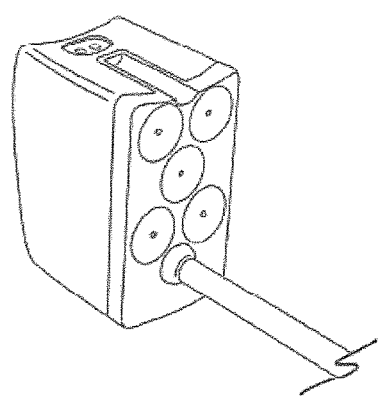

The suture device is readily compatible with a robotic system. In this case the suture device, rather than having its own motors in the handle, may be provided with connection points to use the existing motors in a robotic arm to drive the various mechanisms. A typical device of this type is illustrated in FIGS. 110 and 111.

Figure 112:
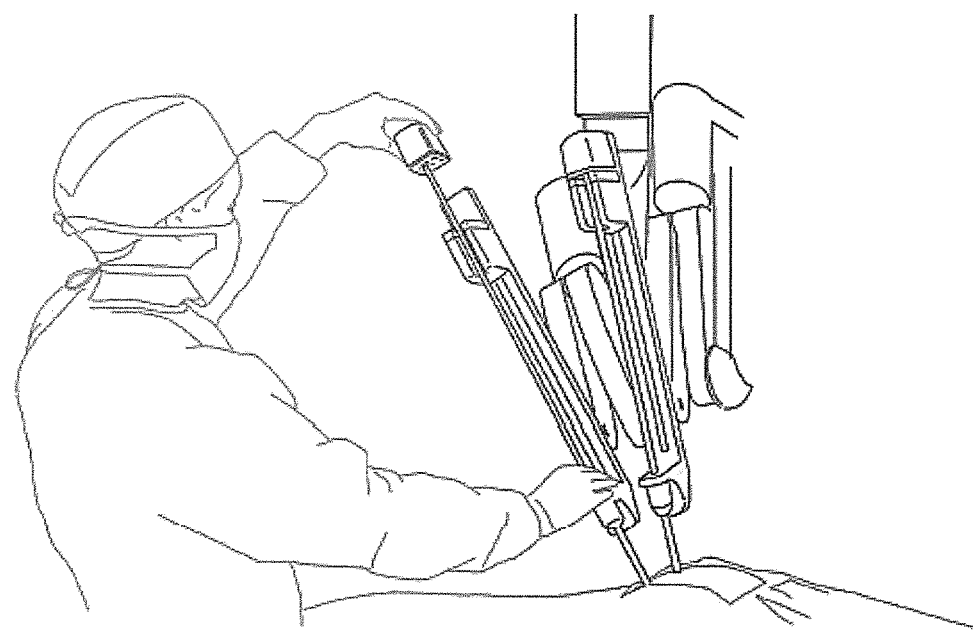
FIG. 112 shows the device docked with a robotic arm.

The device can then be docked with the relevant robot in a similar arrangement to other instruments so the robot would not require a specialist modification to accommodate the meshlock device. The suture device in use in a robotic system is illustrated in FIG. 112.

The distal end of the suture device may be controlled in any appropriate manner.

Figure 113:
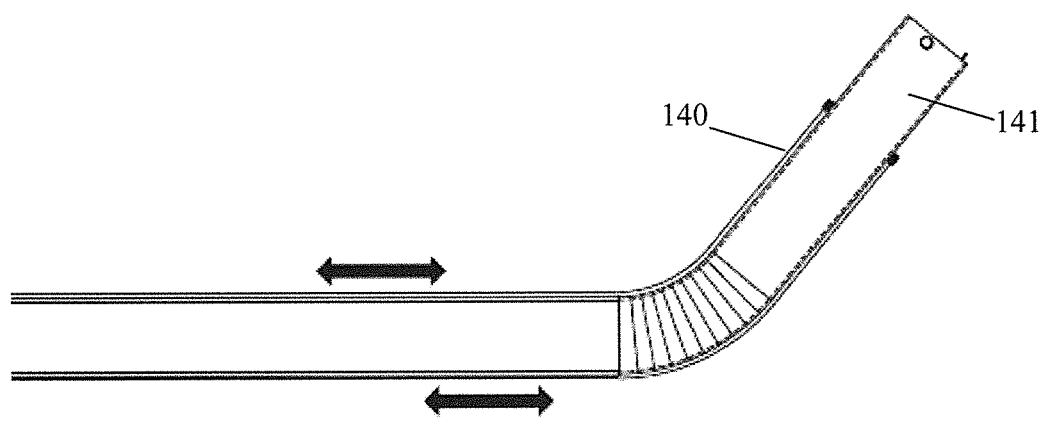
FIGS. 113 to 116 illustrate a device of the invention with a flexible/malleable section.

FIG. 113 illustrates cables 140 used to direct the head 141 of the suture device.

Figure 114:
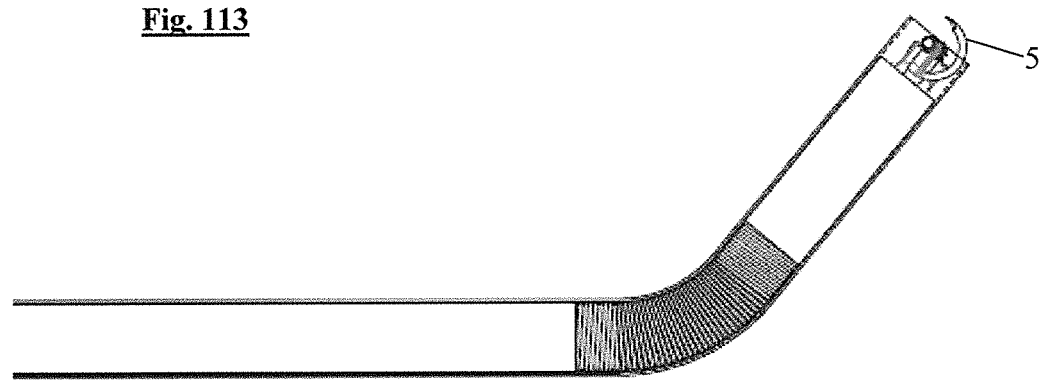
Figure 115:
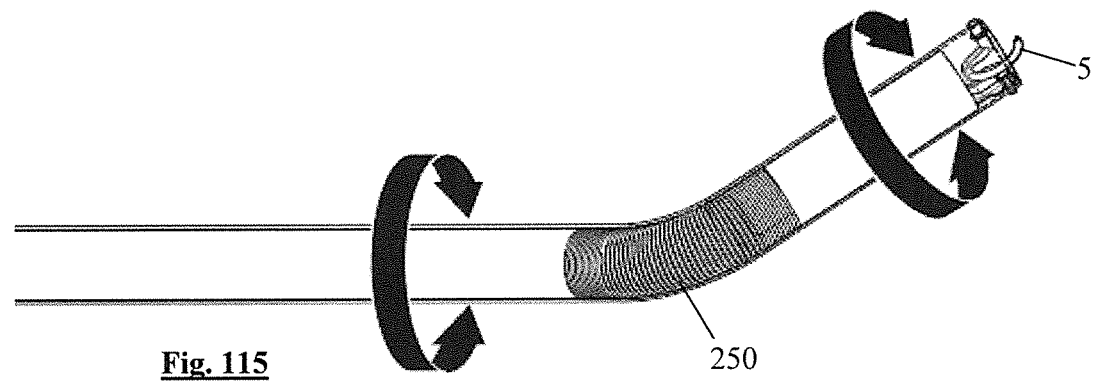

The head of the suture device may be malleable or flexible. For example, the outer shaft may have an armadillo type shell or flexible film. The internal gear driving shaft may have a spring section. This allows the shaft to bend due to the manipulation of the cables and to be rotated in the bent position (FIGS. 114, 115). The spring shaft facilitates turning around bends.

Referring for example to FIG. 115, the internal shaft rotates to drive the needle. In order for it to rotate in a bent configuration, a section of the shaft at the bend point comprises a heavy gauge spring 250. This enables the shaft to be rotated along the length of the shaft device as the turning motor will be located in the handle.

Figure 116:
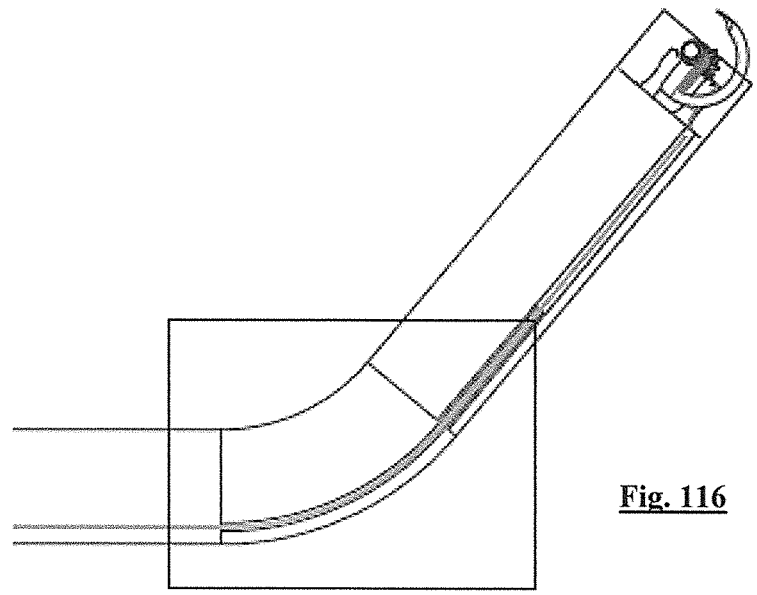
Figure 117:
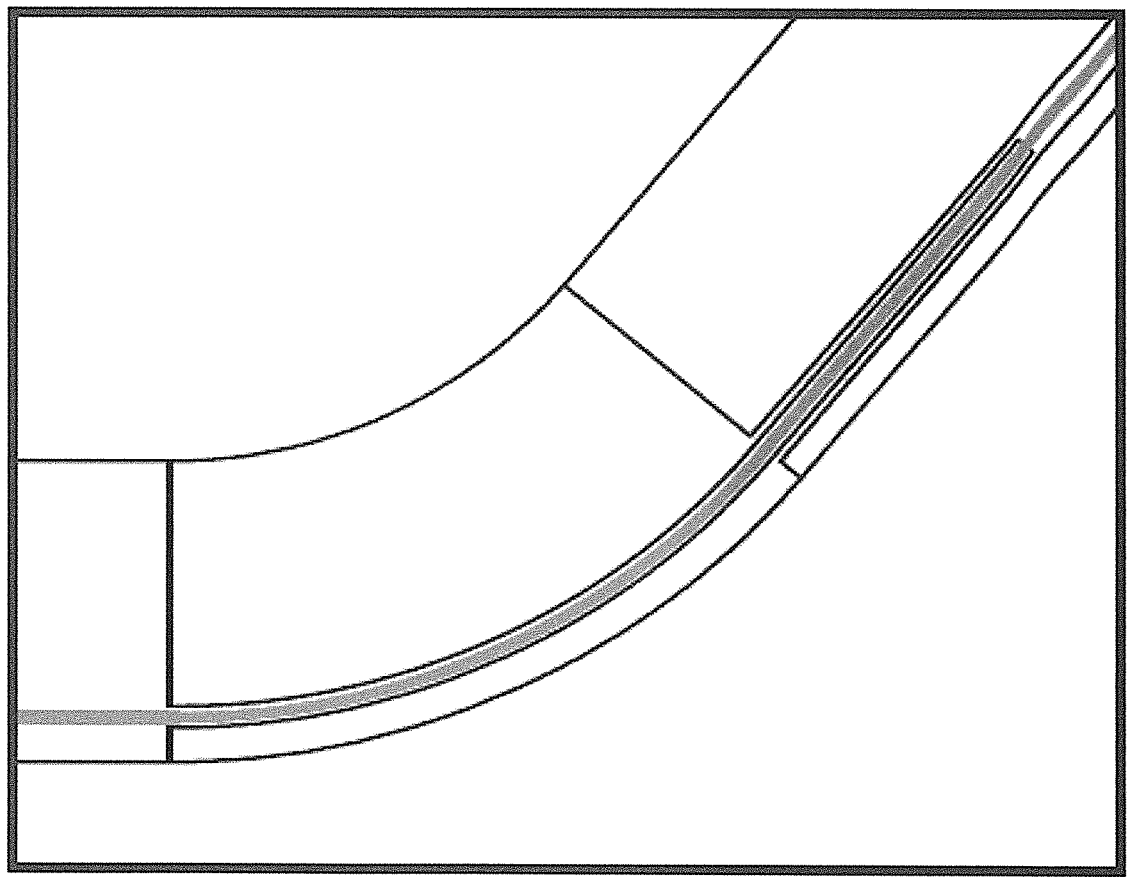
FIG. 117 is an enlarged view of portion of FIG. 116.
Figure 118:
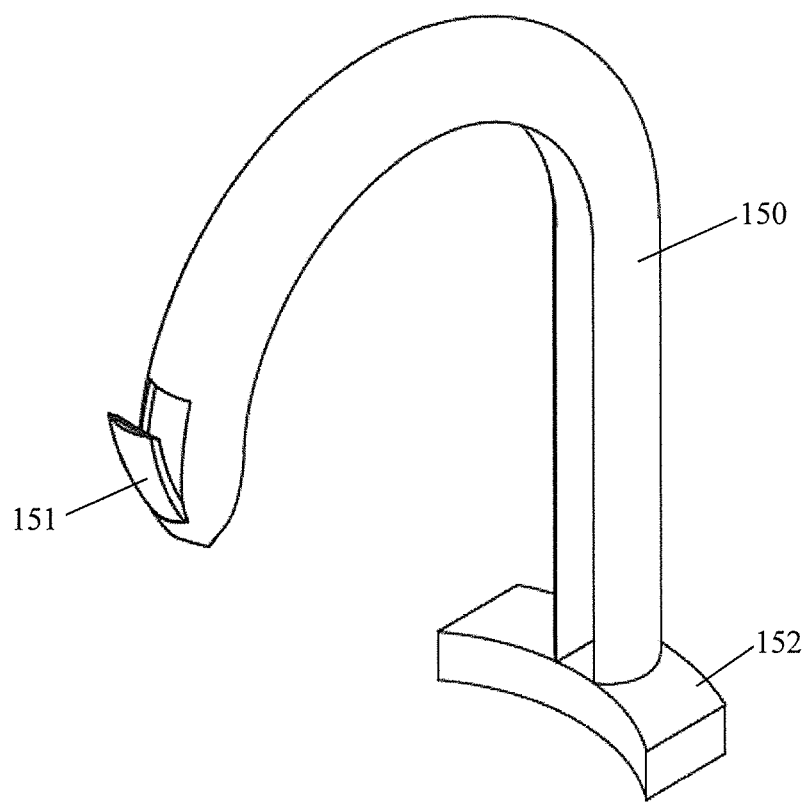
FIG. 118 is an illustration of a tack according to the invention.
Figure 123:
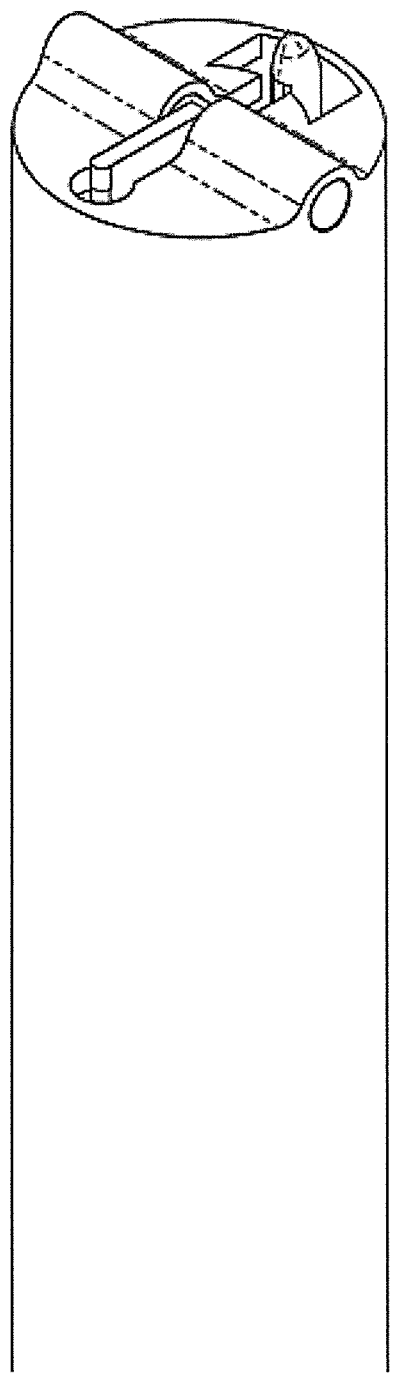
FIGS. 123 to 132 illustrate a device used to insert a tack.
Figure 124:
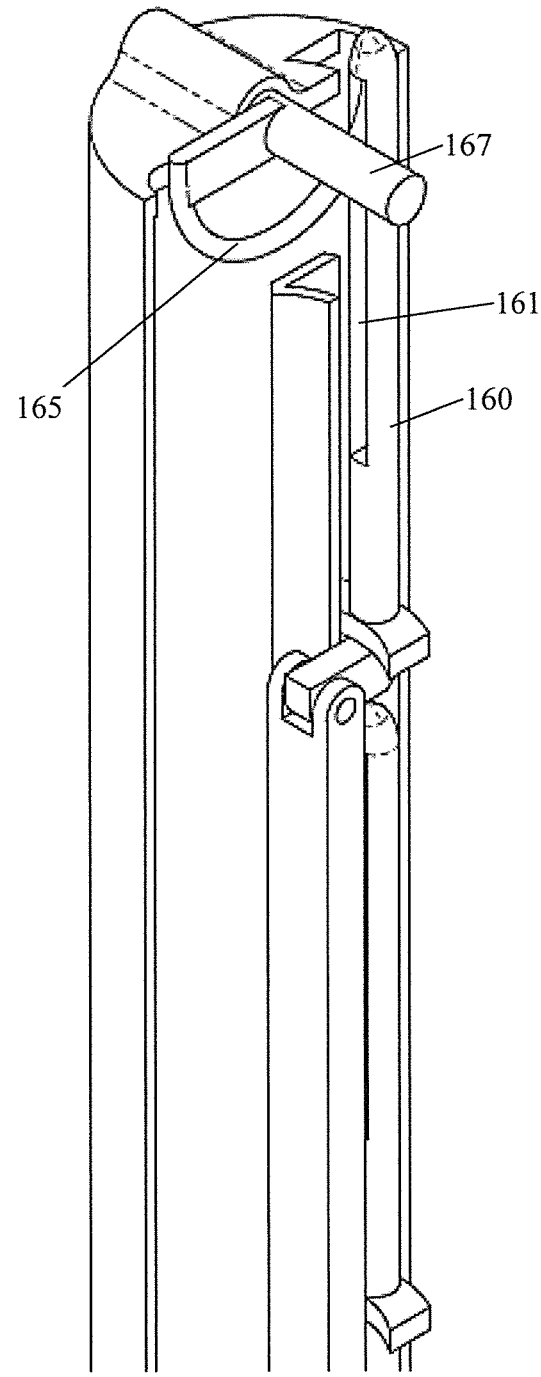
Figure 125:
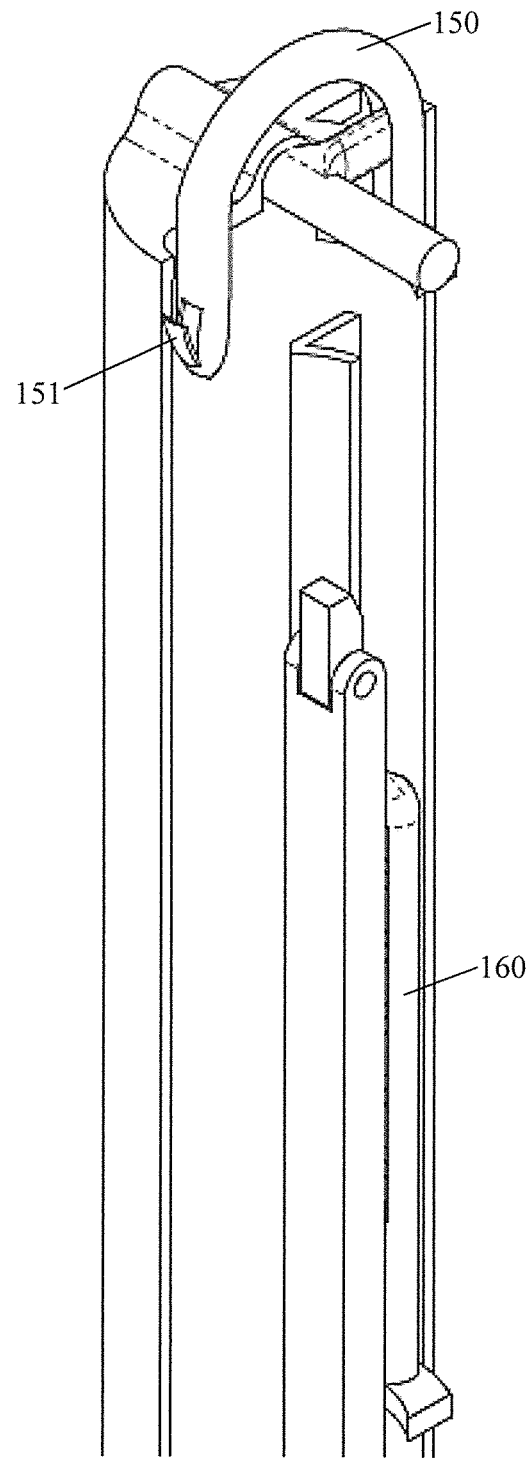
Figure 126:
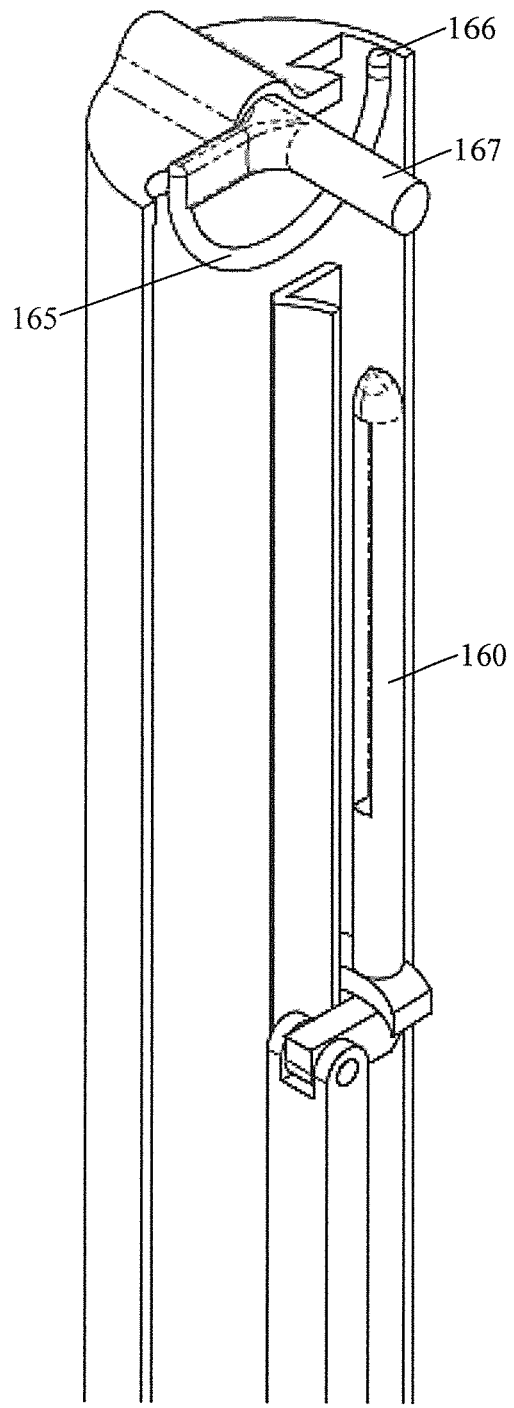
Figure 127:
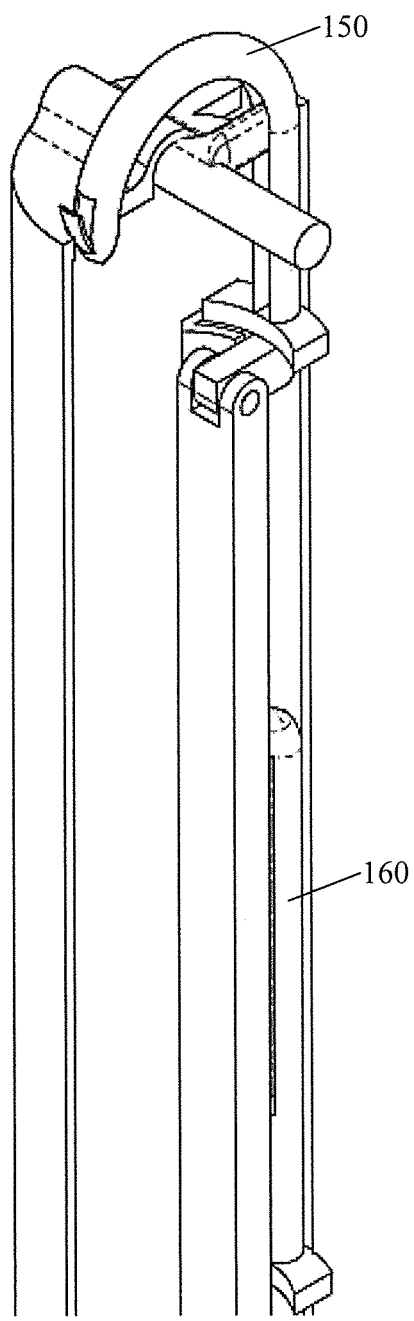
Figure 128:
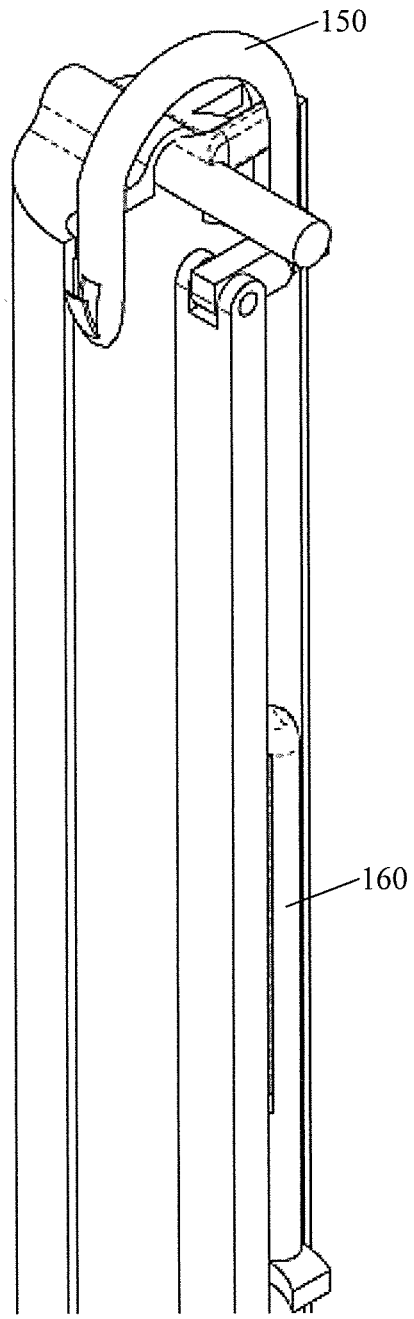
Figures 129, 130:
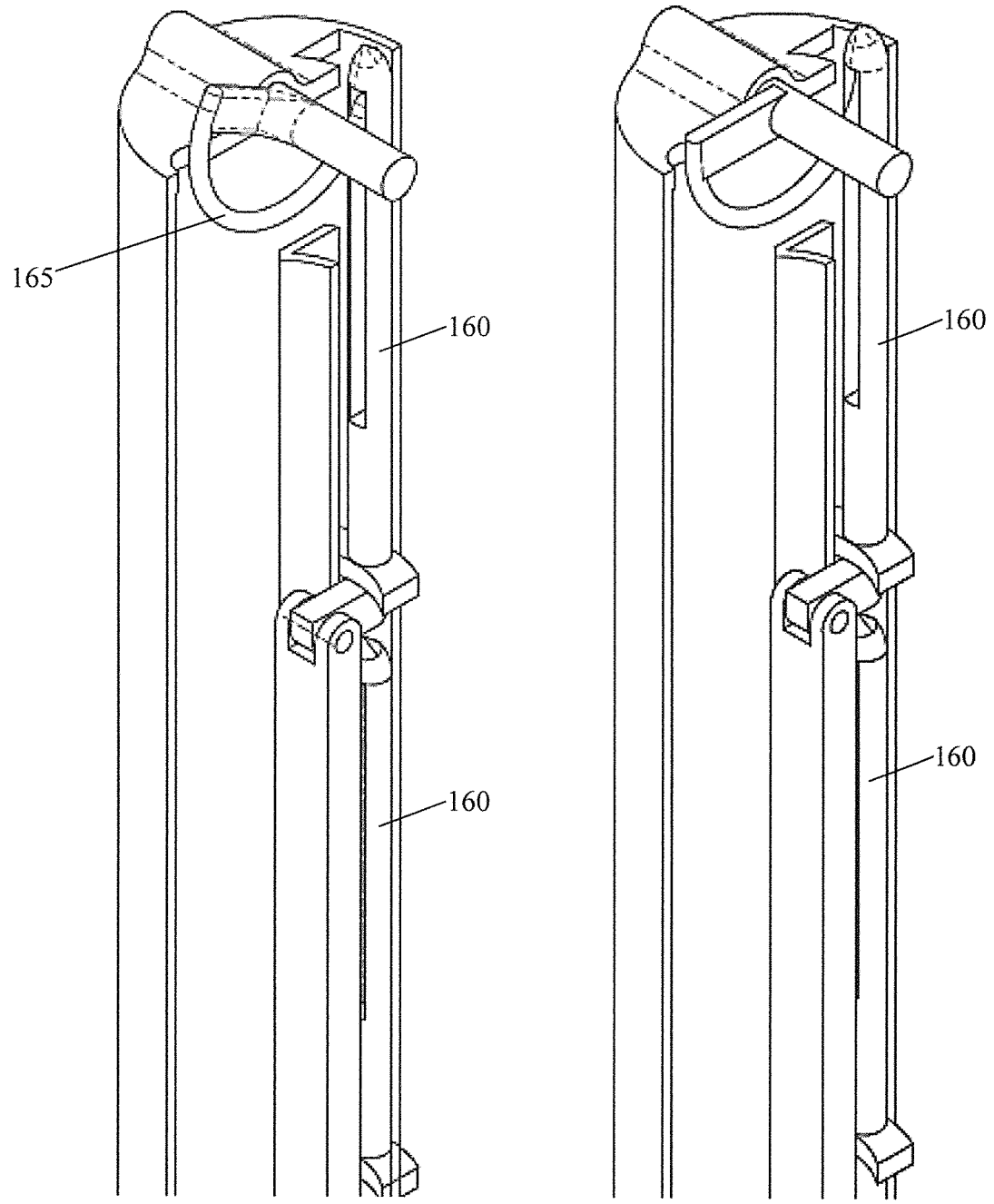

The advancement of a suture around a bent shaft section is illustrated in FIGS. 116 and 117.

To enable the suture to advance round the bend, the suture path closest to the user may have a flexible tube at the end which feeds into the section on the distal end of the device as illustrated in FIGS. 116 and 117. This would allow the head to bend in any direction and allow the suture to travel from the handle to the needle.

The invention provides a suture that may be used to achieve fixation in a loose manner. It will be appreciated that loose fix action may be used in applications other than sutures. One such example is for tacking.

FIGS. 118 to 122 illustrate a double ended loose tack 150 according to the invention. The tack is initially a straight blank 160 as illustrated in FIGS. 119 and 120 and is pulled through the tissue. There is a live hinge barb 151 on the tip of the tack 150 that is pushed in as it is pulled through the tissue, but automatically moves out when it has exited the tissue. The proximal end of the tack 150 has a flange 152.

Referring to FIGS. 121 and 122 a tack being inserted into tissue is illustrated. The tack is pulled through tissue using a blunt needle. The rear flange 152 is then pushed to ensure that the head of the tack clears the tissue and mesh. This enables the live hinge barb 151 to open, preventing the barb from being pulled backwards through the tissue.

FIGS. 123 to 130 illustrate a device of the invention used to form a tack into shape as it is inserted into tissue. In this case the device comprises a rotatable curved needle 165 with a blunt tip 166. The needle 165 in this case is used as a curved pusher. The needle tip 166 passes through a slot 161 in the tack blank 160 and pulls it over a rod 167 carried by the needle 165 which causes the tack blank to deform into the curved shape as illustrated in FIGS. 123 to 130.

The tack 160 is pulled through then pushed to clear the tissue and mesh on the leading point.

Figures 131, 132:
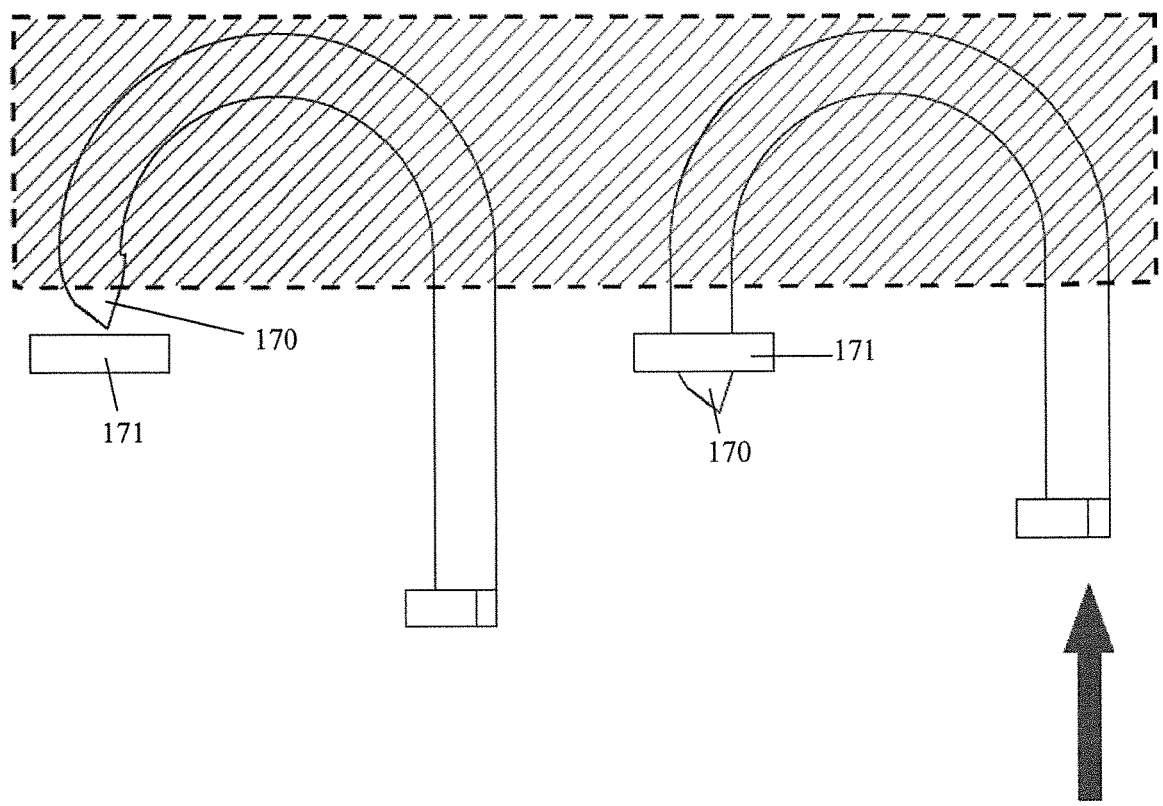
Figure 133:
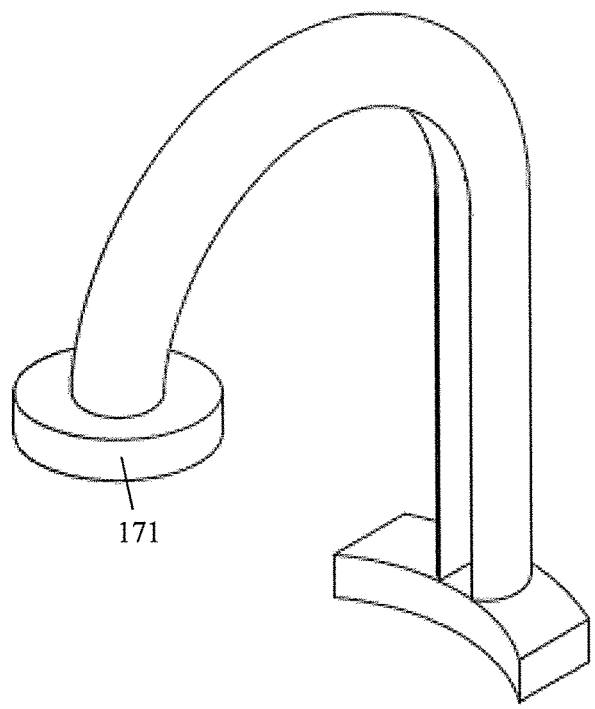
FIG. 133 is an illustration of an alternative tack.
Figure 134:
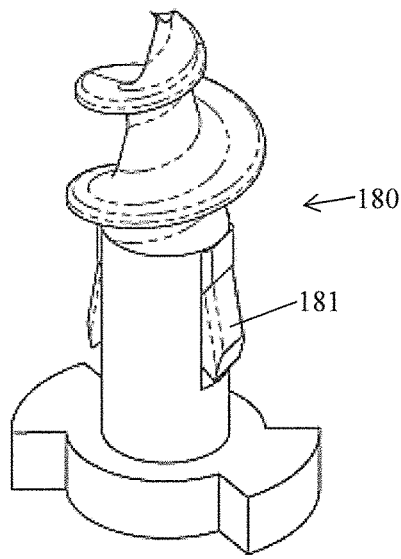
FIGS. 134 to 141 illustrate various further tacks.
Figure 136:
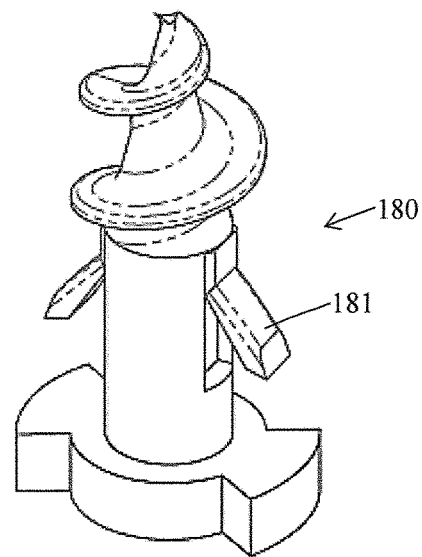
Figure 135:
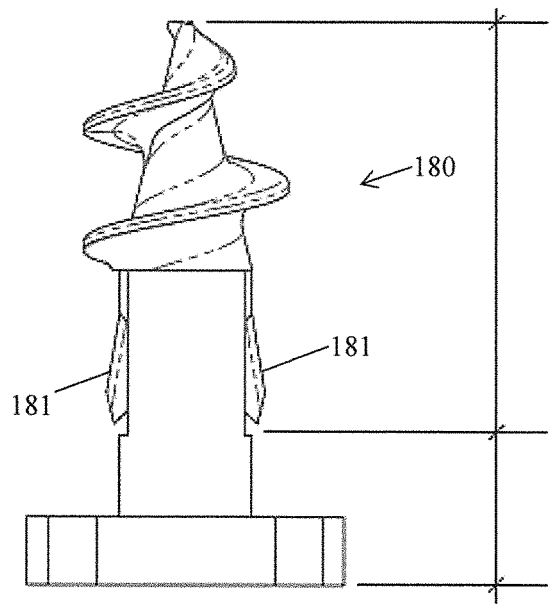

Another tack is illustrated in FIGS. 131 to 133. In this case a leading tip 170 engages with a receiver component 171 that acts as a flange on the leading side.

FIGS. 134 to 137 illustrate another tack 180 which is similar to a standard screw tack but with a longer end that has live hinge barbs 181 that automatically move out to stop it being pulled out.

Figure 137:
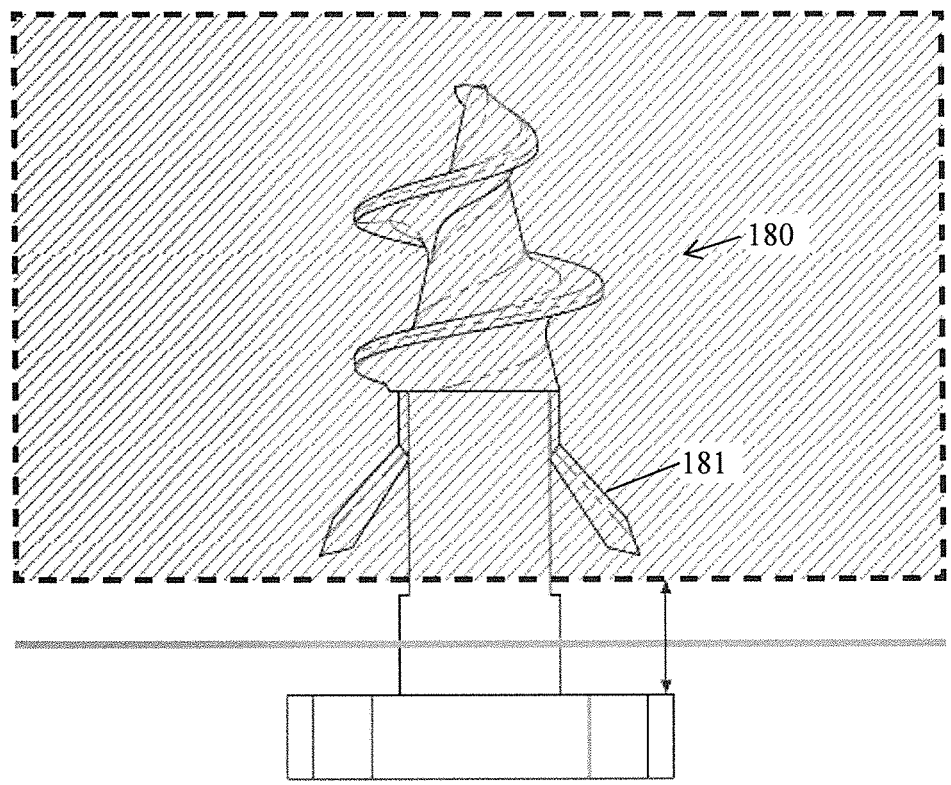
Figure 138:
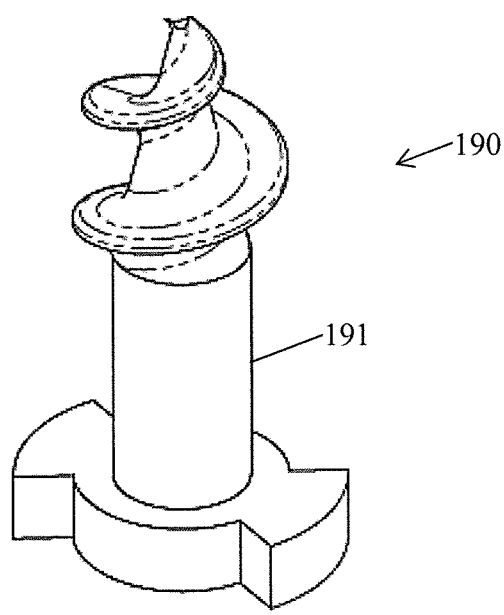
Figure 140:
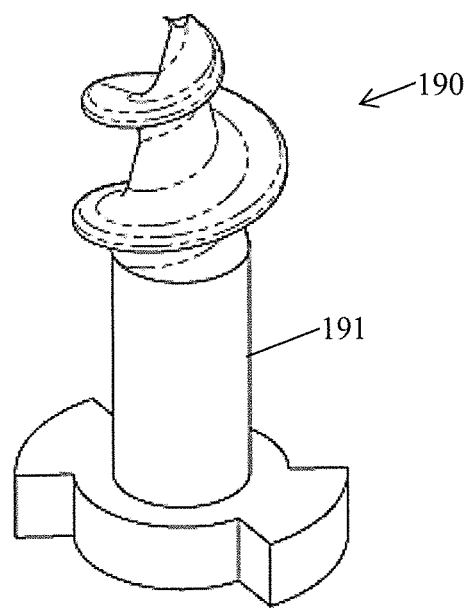
Figure 139:
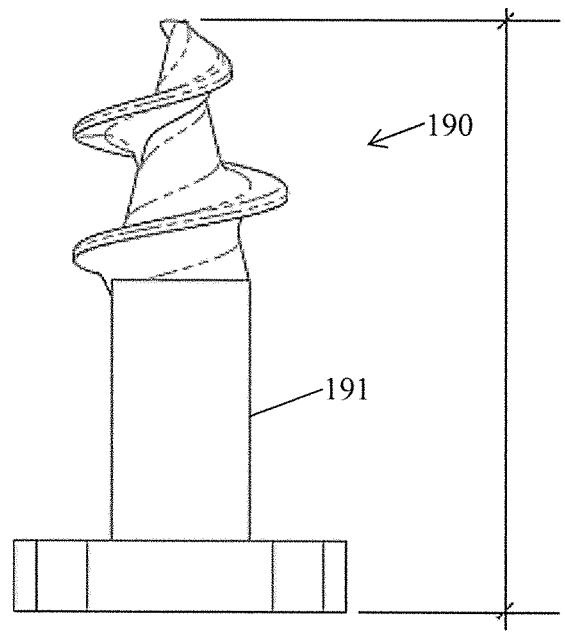
Figure 141:
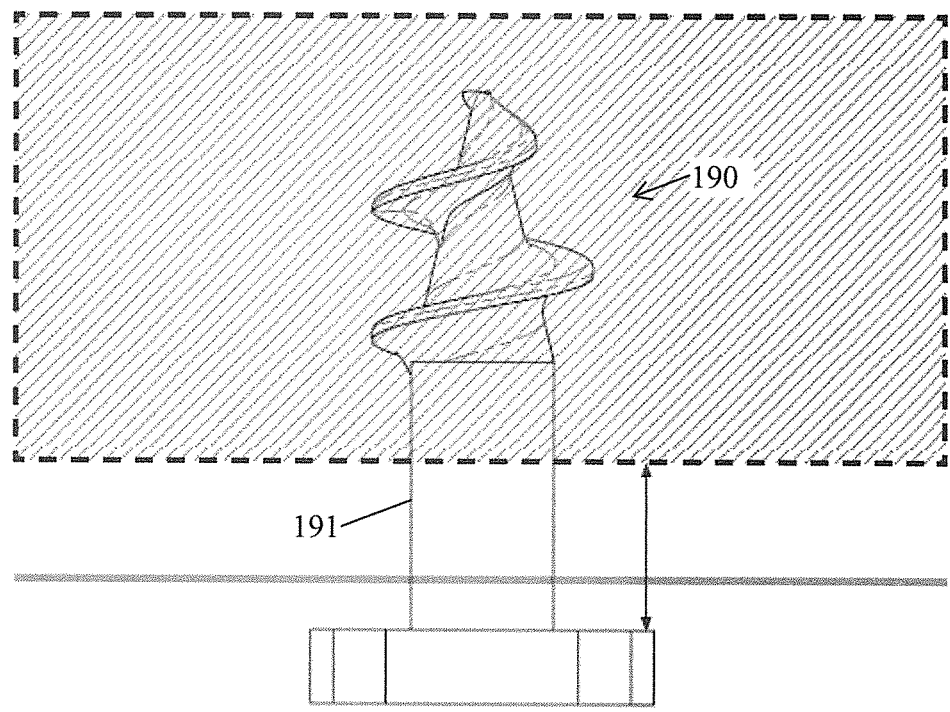

Referring to FIG. 137 the screw tack 180 is made longer and has a live hinge barb 181 that automatically move out to prevent the tack from being pulled out of tissue. The extra length of the shaft of the tack then allows the mesh to move up and down to create tacking that is tension free.

FIGS. 138 to 141 illustrate another tack 190 with a smooth shaft 191 that allows tissue to fill in behind the thread to prevent the tack working its way back out.

Figure 142:
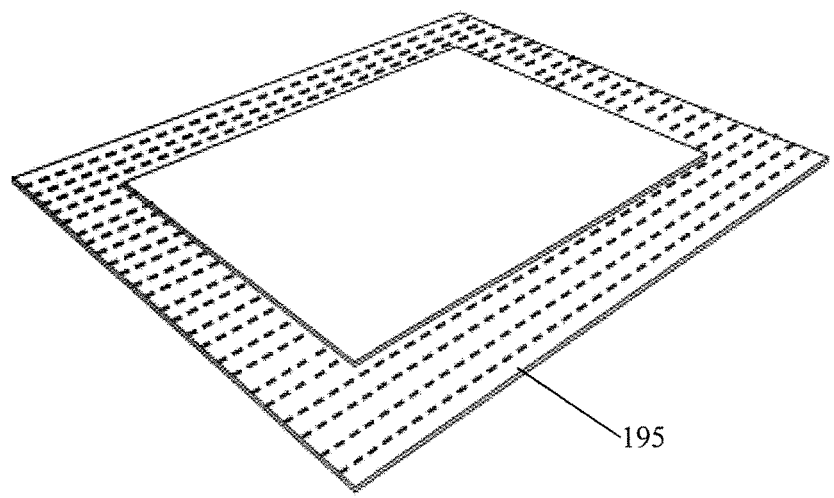
FIGS. 142 and 143 illustrate meshes for use with the devices of the invention.
Figure 143:
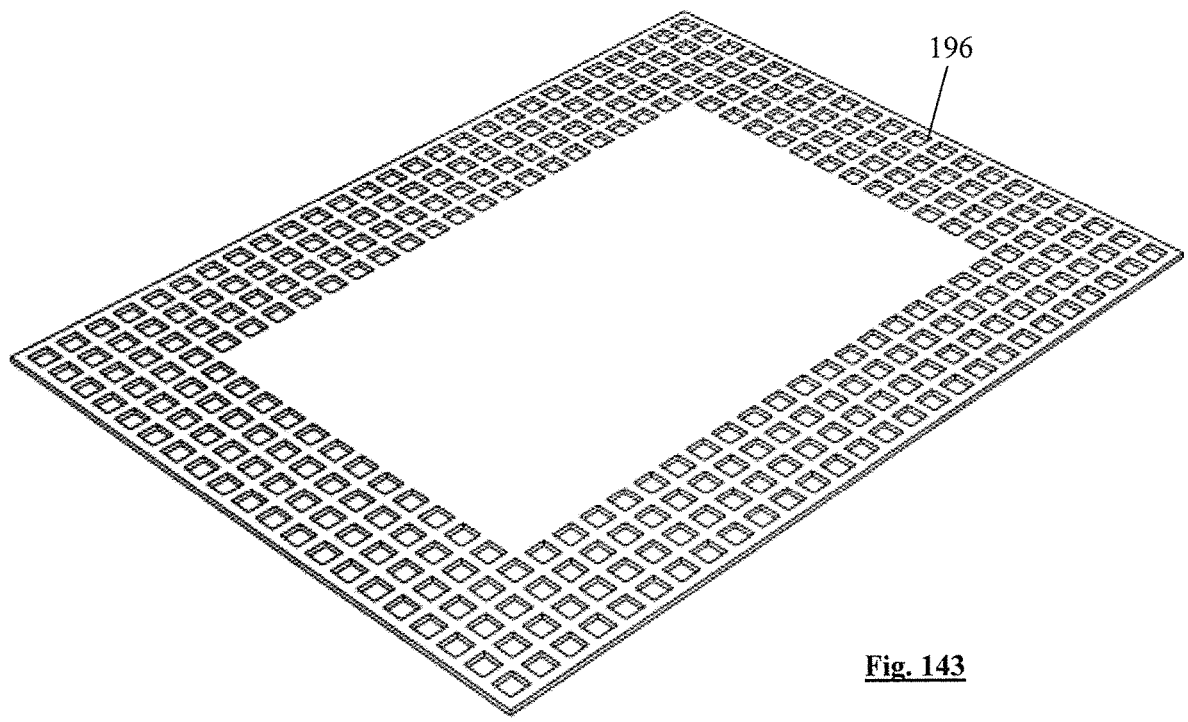

The sutures or tacks may be used to provide loose fixation of a mesh. The mesh may be provided with perforations which are particularly suitable for use with the sutures and/or tacks described. Some suitable pre-perforated meshes 195 and 196 are illustrated in FIGS. 142 and 143. Such meshes may be biocompatible.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiment hereinbefore described which may be varied in construction and detail.

The invention claimed is:

1. A suture device, comprising:
a suture forming device; and
a suture bonding mechanism,
wherein the suture forming device is moveable between a retracted configuration and an extended configuration to position a joint of the suture, and
wherein the suture bonding mechanism includes a heater for bonding portions of a suture together at the joint, the heater including heated clamp plates.

2. A device as claimed in claim 1 comprising a suture path.

3. A device as claimed in claim 2 wherein the suture path comprises a suture delivery section, an intermediate section leading from the suture delivery section to a needle section and a suture return section leading from the needle section.

4. A device as claimed in claim 3 wherein the suture return section is configured to direct a leading end of a suture towards the suture delivery section.

5. A device as claimed in claim 4 wherein the suture return section of the suture path is configured to direct the leading end of the suture across the intermediate section of the suture path to cross the suture and form a loop.

6. A device as claimed in claim 5 wherein the return section of the suture path is offset from the suture path intermediate section to cross the suture intermediate section of the suture path.

7. A device as claimed in claim 2 further comprising a suture advancer for advancing a suture through at least a portion of the suture path.

8. A suture device as claimed in claim 1, wherein the heated clamp plates are configured to have their respective temperatures adjusted depending on a type of suture being applied.

9. A suture device as claimed in claim 1, wherein the heated clamp plates include two flat plates parallel to one another.

10. A suture device as claimed in claim 1, wherein the heater is configured to heat sutures at a temperature of 150° C. for about 1.5 seconds.

11. A suture device as claimed in claim 1, wherein the heater includes a metal shim that is configured to act as a resistor and pass a current.

12. A suture device as claimed in claim 1, wherein the heated clamp plates are configured to pivot about a pivot pin and link arms are connected to heat clamp plates at pivot points.

13. A suture device as claimed in claim 12, wherein the link arms are connected to a rod by a second pin and movement of the rod is configured to open and close the heated clamp plates.

* * * * *